(12) United States Patent
Sherer et al.

(10) Patent No.: US 9,676,757 B2
(45) Date of Patent: Jun. 13, 2017

(54) HETEROCYCLIC COMPOUNDS AS NAV CHANNEL INHIBITORS AND USES THEREOF

(71) Applicant: Merck Patent GmbH, Darmstadt (DE)

(72) Inventors: Brian A. Sherer, Nashua, NH (US); Nadia Brugger, Cambridge, MA (US)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/632,287

(22) Filed: Feb. 26, 2015

(65) Prior Publication Data

US 2015/0266862 A1    Sep. 24, 2015

Related U.S. Application Data

(60) Provisional application No. 61/945,227, filed on Feb. 27, 2014.

(51) Int. Cl.

| | | |
|---|---|---|
| *C07D 405/12* | (2006.01) | |
| *C07D 405/14* | (2006.01) | |
| *C07D 403/12* | (2006.01) | |
| *C07D 401/14* | (2006.01) | |
| *C07D 413/14* | (2006.01) | |
| *C07D 401/12* | (2006.01) | |
| *C07D 403/06* | (2006.01) | |
| *C07D 409/12* | (2006.01) | |
| *C07D 413/04* | (2006.01) | |
| *C07D 413/06* | (2006.01) | |
| *C07D 413/12* | (2006.01) | |
| *C07D 417/12* | (2006.01) | |
| *C07D 417/14* | (2006.01) | |
| *C07D 471/04* | (2006.01) | |
| *C07D 265/30* | (2006.01) | |
| *C07D 207/16* | (2006.01) | |

(52) U.S. Cl.
CPC ......... *C07D 405/14* (2013.01); *C07D 207/16* (2013.01); *C07D 265/30* (2013.01); *C07D 401/12* (2013.01); *C07D 401/14* (2013.01); *C07D 403/06* (2013.01); *C07D 403/12* (2013.01); *C07D 405/12* (2013.01); *C07D 409/12* (2013.01); *C07D 413/04* (2013.01); *C07D 413/06* (2013.01); *C07D 413/12* (2013.01); *C07D 413/14* (2013.01); *C07D 417/12* (2013.01); *C07D 417/14* (2013.01); *C07D 471/04* (2013.01)

(58) Field of Classification Search
CPC .................................................. C07D 405/12
See application file for complete search history.

(56) References Cited

U.S. PATENT DOCUMENTS

| | | | |
|---|---|---|---|
| 5,304,121 A | 4/1994 | Sahatjian | |
| 5,886,026 A | 3/1999 | Hunter | |
| 6,099,562 A | 8/2000 | Ding | |
| 2005/0143372 A1* | 6/2005 | Ghosh | C04B 35/632 514/218 |
| 2010/0210633 A1* | 8/2010 | Lin | C07D 207/08 514/227.8 |
| 2015/0274657 A1* | 10/2015 | Montagne et al. | C07D 417/14 |

FOREIGN PATENT DOCUMENTS

| | | |
|---|---|---|
| EP | 1449841 A1 | 8/2004 |
| WO | 9210492 A1 | 6/1992 |
| WO | 9316077 A1 | 8/1993 |
| WO | 9410145 A1 | 5/1994 |
| WO | 2007042250 A1 | 4/2007 |
| WO | 2008045564 A2 | 4/2008 |
| WO | 2013149704 A1 | 10/2013 |
| WO | 2014053210 A1 | 4/2014 |

OTHER PUBLICATIONS

Nguyen et al. (Bioorg. Med. Chem. Lett. 22 (2012) 1055-1060).*
Shibata et al. (CAPLUS Abstract of: WO 9633992 (Oct. 31, 1996)).*
Yang et al. (Bioorg. Med. Chem. Lett. 23 (2013) 4388-4392).*
De Luca et al., Searching for novel anti-myotonic agents: Pharmacophore requirement for use-dependent block of skeletal muscle sodium channels by N-benzylated cyclic derivatives of tocainide, Neuromuscular Disorders, 2012, 22: 56-65.
Einsiedel et al., Phenyloxazoles and Phenylthiazoles as Benzamide Bioisosteres: Synthesis and Dopamine Receptor Binding Profiles, Bioorganic & Medicinal Chemistry Letters, 2000, 10: 2041-2044.
PCT International Search Report, dated May 11, 2015, pp. 1-7.
Berge, Pharmaceutical Salts, Journal of Pharmaceutical Sciences, 1977, 66(1): 1-19.
Foster, Deuterium Isotophe Effects in the Metabolism of Drugs and Xenobiotics: Implications for Drug Design, Advances in Drug Research, 1985, 14: 1-40.
Gillette, Theory for the Observed Isotope Effects on the Formation of Multiple Products by Different Kinetic Mechanisms of Cytochrome P450, Enzymes, Biochemistry,1994, 33(10): 2927-2937.
Hanzlik, Active Site Dynamics of Toluene Hydroxylation of Cytochrome P-450, J. Org. Chem., 1990, 55: 3992-3997.
Jarman, The deuterium isotope effect for the a-hydroxylation of tamoxifen by rat liver microsomes accounts for the reduced genotoxicity of D5-ethyl]taxoxifen, Carcinogenesis, 1995, 16(4): 683-688.
Reider, Synthesis of (R)-Serine-2-d and Its Conversion to the Broad Spectrum Antibiotic Fludalanine, J. Org. Chem., 1987, 52: 3326-3334.

* cited by examiner

*Primary Examiner* — Robert Havlin
(74) *Attorney, Agent, or Firm* — Dwight D. Kim; EMD Serono Research and Development Institute

(57) ABSTRACT

The present invention relates to heterocyclic compounds, and pharmaceutically acceptable compositions thereof, useful as Nav1.6 inhibitors.

5 Claims, 1 Drawing Sheet

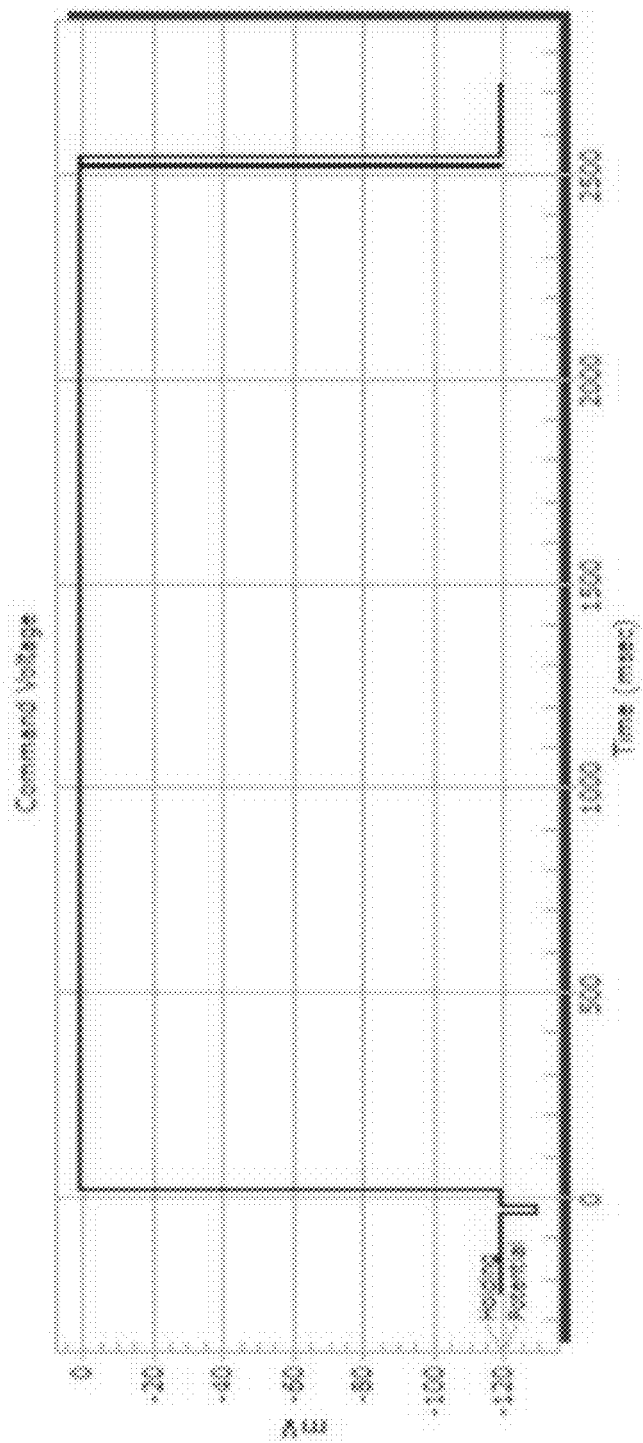

HETEROCYCLIC COMPOUNDS AS NAV CHANNEL INHIBITORS AND USES THEREOF

RELATED APPLICATIONS

This application claims the benefit of U.S. provisional application 61/945,227, filed on Feb. 27, 2014, the contents of which are herein incorporated in its entirety by reference.

TECHNICAL FIELD OF THE INVENTION

The present invention relates to heterocyclic compounds that are useful as inhibitors of NaV1.6. The invention also provides pharmaceutically acceptable compositions comprising compounds of the present invention and methods of using said compositions in the treatment of various disorders.

BACKGROUND OF THE INVENTION

Mechanistics studies on white matter damage have shown that exposure of axons to hypoxia leads to excessive sodium influx and a consequent inverse functioning of the sodium-calcium exchanger (NCX) that ultimately triggers activation of calcium-mediated cell death cascades. Experimentally, this idea is supported by a large body of experimental observations including that blocking of sodium channels with Tetrodotoxin (TTX) or saxitosin, blocking of the NCX (with bepridil, benzamil, dichlorobenzamil) or manipulation of the transmembrane sodium gradient by substituting $Na^+$ with $Li^+$ or choline can all protect axons against anoxic injury. Conversely, increasing sodium channel permeability during anoxia with veratridine resulted in greater injury. Under hypoxic conditions, the availability of adenosine triphosphate (ATP) within is axoplasm becomes limited not only due to decrease synthesis but also due to the increased demands from the sodium-potassium adenosine triphosphatase ($Na^+/K^+$-ATPase) for extruding exceeding sodium. It has also been shown that in an inflammatory milieu, where nitric oxide (NO) and reactive oxygen species (ROS) are produced by phagocytic cells such as macrophages and microglia, the availability of ATP is diminished by the damage that this mediators can directly cause on mitochondria, particularly on enzymes involved in the synthesis of ATP itself. Through this mechanism, NO donors can exacerbate the axonal damage induced by hypoxia. Indeed, in multiple sclerosis, where a persistent sodium current is hypothesized to overload demyelinated axons and where the synthesis of ATP is affected by NO and reactive oxygen species (ROS) due to the inflammatory nature of this disease, any initial $Na^+$ overload cannot be overcome and creates a vicious cycle, causing reverse functioning of the NCX which in turn activates $Ca^{+2}$-mediated cell cascades including the increased synthesis of NO, which besides impairing ATP synthesis itself, in addition to triggering axonal degeneration and apoptosis by multiple known mechanisms. This aspect of the pathology of multiple sclerosis is well documented in the literature and has been named virtual hypoxia.

In line with the hypothesis of the association of sodium overload and axonal degeneration in multiple sclerosis are the observations of increased total sodium content in the advanced stage of relapsing-remitting (RR) multiple sclerosis, especially in the normal-appearing brain tissues by using sodium 23 (23Na) magnetic resonance (MR) imaging. Sodium channel blockers such as Phenytoin, Carbamazepine, Flecainide and Lamotrigine are well established drugs and are indicated for different conditions such as epilepsy, neuropathic pain and arrhythmia. All these compound have one feature in common, i.e., they are all state-dependent sodium channel blockers, meaning that they do not affect the normal functioning of sodium channels, but do so particularly in pathological states where higher than normal neuronal firing increases the proportion of channels that are found at any time point in a conformational configuration called inactivated state. This is crucial for the safety of these drugs given that action potentials in the central and peripheral nervous systems (CNS and PNS) and axons are conducted by voltage-gated sodium channels.

All of the above mentioned examples of VGSC blockers have been tested in EAE and have in general been shown to improve clinical scores, ameliorate the axonal loss and demyelination associated with disease and revert the loss in axonal conductivity in the spinal cord of the test animals. Voltage-gated sodium channel blockers also exhibit a protective effect in other disease models including spinal cord injury which is a relevant CNS injury model. Collectively, the body of evidence discussed above was convincing enough to raise interest within the scientific community to test the efficacy of VGSC as neuroprotective agents and Lamotrigine was tested in a randomised, double-blind phase II clinical trial for neuroprotection in secondary progressive MS patients and Lamotrigine treatment reduced the deterioration of the timed 25-foot walk (p=0.02) over 2 years.

Two voltage-gated sodium channel (VGSC) isoforms namely Nav1.2 and Nav1.6 have been shown to be overexpressed in post-morten tissue from multiple sclerosis patients and in different animal models mimicking the disease and that are collectively known as experimental autoimmune encephalomyelitis (EAE). Amongst neurons overexpressing VGSC, those overexpressing Nav1.6 are more frequently co-localized with the degeneration marker β-amyloid precursor protein (APP) than those overexpressing Nav1.2. Indeed, it has long been known that axons selectively expressing Nav1.2 are extremely resistant to anoxic injury. This is likely related to the electrophysiological properties of this channel: Nav1.2 shows greater accumulation of inactivation at high frequencies of stimulation while producing smaller persistent currents in comparison with Nav1.6. On the other hand, Nav1.6 produces large persistent currents that may play a role in triggering reverse functioning of the NCX which can injure demyelinated axons where Nav1.6 and the NCX are co-localized. Collectively, this evidence indicates that the Nav1.6 isoform mediates axonal degeneration in multiple sclerosis.

SUMMARY OF THE INVENTION

In one aspect, the invention provides for compounds of formula I:

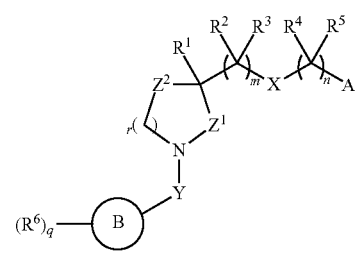

or a pharmaceutically acceptable salt, solvate, hydrate, or polymorph thereof, wherein each of $Z^1$, $Z^2$, X, A, Y, ring B, $R^1$, $R^2$, $R^3$, $R^4$, $R^5$, m, n, q, and r, is as defined and described in embodiments herein.

Compounds of the present invention, and pharmaceutically acceptable compositions thereof, are useful for treating a variety of diseases, disorders or conditions, associated with NaV1.6. Such diseases, disorders, or conditions include those described herein.

FIGURES

FIG. 1—Command Voltage

DETAILED DESCRIPTION OF CERTAIN EMBODIMENTS

1. General Description of Compounds of the Invention

In certain aspects, the present invention provides for inhibitors of NaV1.6. In some embodiments, such compounds include those of the formulae described herein, or a pharmaceutically acceptable salt, solvate, hydrate, or polymorph thereof, wherein each variable is as defined and described herein.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Exemplary aliphatic groups are linear or branched, substituted or unsubstituted $C_1$-$C_8$ alkyl, $C_2$-$C_8$ alkenyl, $C_2$-$C_8$ alkynyl groups and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, or phosphorus (including, any oxidized form of nitrogen, sulfur, or phosphorus; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl", "aralkoxy", or "aryloxyalkyl", refers to monocyclic and bicyclic ring systems having a total of five to fourteen ring members, wherein at least one ring in the system is aromatic and wherein each ring in the system contains three to seven ring members. The term "aryl" is used interchangeably with the term "aryl ring". In certain embodiments of the present invention, "aryl" refers to an aromatic ring system. Exemplary aryl groups are phenyl, biphenyl, naphthyl, anthracyl and the like, which optionally includes one or more substituents. Also included within the scope of the term "aryl", as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3- b]-1,4-oxazin-3(4H)-one. A heteroaryl group is optionally mono- or bicyclic. The term "heteroaryl" is used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen is N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group is optionally mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, certain compounds of the invention contain "optionally substituted" moieties. In general, the term "substituted", whether preceded by the term "optionally" or not, means that one or more hydrogens of the designated moiety are replaced with a suitable substituent. "Substituted" applies to one or more hydrogens that are either explicit or implicit from the structure

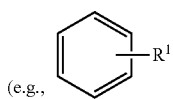

refers to at least

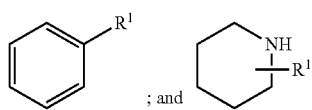

; and refers to at least

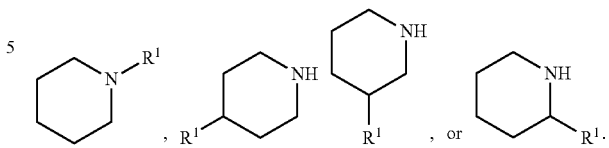

Unless otherwise indicated, an "optionally substituted" group has a suitable substituent at each substitutable position of the group, and when more than one position in any given structure is substituted with more than one substituent selected from a specified group, the substituent is either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently deuterium; halogen; —$(CH_2)_{0-4}R^\circ$; —$(CH_2)_{0-4}OR^\circ$; —$O(CH_2)_{0-4}R^\circ$, —$O—(CH_2)_{0-4}C(O)OR^\circ$; —$(CH_2)_{0-4}CH(OR^\circ)_2$; —$(CH_2)_{0-4}SR^\circ$; —$(CH_2)_{0-4}Ph$, which are optionally substituted with $R^\circ$; —$(CH_2)_{0-4}O(CH_2)_{0-1}Ph$ which is optionally substituted with $R^\circ$; —CH=CHPh, which is optionally substituted with $R^\circ$; —$(CH_2)_{0-4}O(CH_2)_{0-1}$-pyridyl which is optionally substituted with $R^\circ$; —$NO_2$; —CN; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-4}OC(O)R^\circ$; —$OC(O)(CH_2)_{0-4}SR^\circ$, —$SC(S)SR^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —$SC(S)SR^\circ$, —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —$C(NH)NR^\circ_2$; —$P(O)_2R^\circ$; —$P(O)R^\circ_2$; —$OP(O)R^\circ_2$; —$OP(O)(OR^\circ)_2$; $SiR^\circ_3$; —$(C_{1-4}$ straight or branched alkylene)O—$N(R^\circ)_2$; or —$(C_{1-4}$ straight or branched alkylene)C(O)O—$N(R^\circ)_2$, wherein each $R^\circ$ is optionally substituted as defined below and is independently hydrogen, $C_{1-6}$ aliphatic, —$CH_2Ph$, —$O(CH_2)_{0-1}$ Ph, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which is optionally substituted as defined below.

Suitable monovalent substituents on $R^\circ$ (or the ring formed by taking two independent occurrences of $R^\circ$ together with their intervening atoms), are independently deuterium, halogen, —$(CH_2)_{0-2}R^\bullet$, -(haloR$^\bullet$), —$(CH_2)_{0-2}OH$, —$(CH_2)_{0-2}OR^\bullet$, —$(CH_2)_{0-2}CH(OR^\bullet)_2$; —$O(haloR^\bullet)$, —CN, —$N_3$, —$(CH_2)_{0-2}C(O)R^\bullet$, —$(CH_2)_{0-2}C(O)OH$, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which is substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which is optionally substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which is optionally substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

In certain embodiments, the terms "optionally substituted", "optionally substituted alkyl," "optionally substituted "optionally substituted alkenyl," "optionally substituted alkynyl", "optionally substituted carbocyclic," "optionally substituted aryl", "optionally substituted heteroaryl," "optionally substituted heterocyclic," and any other optionally substituted group as used herein, refer to groups that are substituted or unsubstituted by independent replacement of one, two, or three or more of the hydrogen atoms thereon with typical substituents including, but not limited to:

—F, —Cl, —Br, —I, deuterium,

—OH, protected hydroxy, alkoxy, oxo, thiooxo,

—NO$_2$, —CN, CF$_3$, N$_3$,

—NH$_2$, protected amino, —NH alkyl, —NH alkenyl, —NH alkynyl, —NH cycloalkyl, —NH-aryl, —NH-heteroaryl, —NH-heterocyclic, -dialkylamino, -diarylamino, -diheteroarylamino, —O— alkyl, —O— alkenyl, —O— alkynyl, —O— cycloalkyl, —O-aryl, —O-heteroaryl, —O-heterocyclic, —C(O)— alkyl, —C(O)— alkenyl, —C(O)— alkynyl, —C(O)— carbocyclyl, —C(O)-aryl, —C(O)— heteroaryl, —C(O)-heterocyclyl, —CONH$_2$, —CONH— alkyl, —CONH— alkenyl, —CONH— alkynyl, —CONH-carbocyclyl, —CONH-aryl, —CONH-heteroaryl, —CONH-heterocyclyl, —OCO$_2$— alkyl, —OCO$_2$— alkenyl, —OCO$_2$— alkynyl, —OCO$_2$— carbocyclyl, —OCO$_2$-aryl, —OCO$_2$-heteroaryl, —OCO$_2$-heterocyclyl, —OCONH$_2$, —OCONH— alkyl, —OCONH— alkenyl, —OCONH— alkynyl, —OCONH— carbocyclyl, —OCONH— aryl, —OCONH— heteroaryl, —OCONH— heterocyclyl, —NHC(O)— alkyl, —NHC(O)— alkenyl, —NHC(O)— alkynyl, —NHC(O)— carbocyclyl, —NHC(O)-aryl, —NHC(O)-heteroaryl, —NHC(O)-heterocyclyl, —NHCO$_2$— alkyl, —NHCO$_2$— alkenyl, —NHCO$_2$— alkynyl, —NHCO$_2$— carbocyclyl, —NHCO$_2$— aryl, —NHCO$_2$— heteroaryl, —NHCO$_2$-heterocyclyl, —NHC(O)NH$_2$, —NHC(O)NH— alkyl, —NHC(O)NH— alkenyl, —NHC(O)NH— alkenyl, —NHC(O)NH— carbocyclyl, —NHC(O)NH-aryl, —NHC(O)NH-heteroaryl, —NHC(O)NH— heterocyclyl, NHC(S)NH$_2$, —NHC(S)NH— alkyl, —NHC(S)NH— alkenyl, —NHC(S)NH— alkynyl, —NHC(S)NH— carbocyclyl, —NHC(S)NH-aryl, —NHC(S)NH-heteroaryl, —NHC(S)NH-heterocyclyl, —NHC(NH)NH$_2$, —NHC(NH)NH— alkyl, —NHC(NH)NH— alkenyl, —NHC(NH)NH— alkenyl, —NHC(NH)NH— carbocyclyl, —NHC(NH)NH-aryl, —NHC(NH)NH-heteroaryl, —NHC(NH)NH— heterocyclyl, —NHC(NH)— alkyl, —NHC(NH)— alkenyl, —NHC(NH)— alkenyl, —NHC(NH)— carbocyclyl, —NHC(NH)-aryl, —NHC(NH)-heteroaryl, —NHC(NH)-heterocyclyl, —C(NH)NH— alkyl, —C(NH)NH— alkenyl, —C(NH)NH— alkynyl, —C(NH)NH— carbocyclyl, —C(NH)NH-aryl, —C(NH)NH-heteroaryl, —C(NH)NH-heterocyclyl, —S(O)— alkyl, —S(O)— alkenyl, —S(O)— alkynyl, —S(O)— carbocyclyl, —S(O)-aryl, —S(O)-heteroaryl, —S(O)-heterocyclyl —SO$_2$NH$_2$, —SO$_2$NH— alkyl, —SO$_2$NH— alkenyl, —SO$_2$NH— alkynyl, —SO$_2$NH— carbocyclyl, —SO$_2$NH— aryl, —SO$_2$NH— heteroaryl, —SO$_2$NH— heterocyclyl, —NHSO$_2$— alkyl, —NHSO$_2$— alkenyl, —NHSO$_2$— alkynyl, —NHSO$_2$— carbocyclyl, —NHSO$_2$-aryl, —NHSO$_2$-heteroaryl, —NHSO$_2$-heterocyclyl,

—CH$_2$NH$_2$, —CH$_2$SO$_2$CH$_3$,

-mono-, di-, or tri-alkyl silyl,

-alkyl, -alkenyl, -alkynyl, -aryl, -arylalkyl, -heteroaryl, -heteroarylalkyl, -heterocycloalkyl, -cycloalkyl, -carbocyclic, -heterocyclic, polyalkoxyalkyl, polyalkoxy, -methoxymethoxy, -methoxyethoxy, —SH, —S— alkyl, —S— alkenyl, —S— alkynyl, —S— carbocyclyl, —S-aryl, —S-heteroaryl, —S-heterocyclyl, or methylthiomethyl.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. In some embodiments, the group comprises one or more deuterium atoms.

There is furthermore intended that a compound of the formula I includes isotope-labeled forms thereof. An isotope-labeled form of a compound of the formula I is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula I by well-known methods include isotopes of hydrogen, carbon, nitrogen, oxygen, phos-phorus, fluo-rine and chlorine, for example $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. A compound of the formula I, a prodrug, thereof or a pharmaceutically acceptable salt of either which contains one or more of the above-mentioned isotopes and/or other isotopes of other atoms is intended to be part of the present invention. An isotope-labeled compound of the formula I can be used in a number of beneficial ways. For example, an isotope-labeled compound of the formula I into which, for example, a radioisotope, such as $^3H$ or $^{14}C$, has been incorporated, is suitable for medicament and/or substrate tissue distribution assays. These radioisotopes, i.e. tritium ($^3H$) and carbon-14 ($^{14}C$), are particularly preferred owing to simple preparation and excellent detectability. Incorporation of heavier isotopes, for example deuterium ($^2H$), into a compound of the formula I has therapeutic advantages owing to the higher metabolic stability of this isotope-labeled compound. Higher metabolic stability translates directly into an increased in vivo half-life or lower dosages, which under most circumstances would represent a preferred embodiment of the present invention. An isotope-labeled compound of the formula I can usually be prepared by carrying out the procedures disclosed in the synthesis schemes and the related description, in the example part and in the preparation part in the present text, replacing a non-isotope-labeled reactant by a readily available isotope-labeled reactant.

Deuterium ($^2H$) can also be incorporated into a compound of the formula I for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D=2-7$ are typical. If this rate difference is successfully applied to a com-pound of the formula I that is susceptible to oxidation, the profile of this compound in vivo can be drastically modified and result in improved pharmacokinetic properties.

When discovering and developing therapeutic agents, the person skilled in the art is able to optimize pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I with improved stability through resistance to such oxidative metabolism. Significant improvements in the pharmacokinetic profiles of compounds of the formula I are thereby obtained, and can be expressed quantitatively in terms of increases in the in vivo half-life (t/2), concentration at maximum therapeutic effect ($C_{max}$), area under the dose response curve (AUC), and F; and in terms of reduced clearance, dose and materials costs.

The following is intended to illustrate the above: a compound of the formula I which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favorable and accurate determination of the extent of the extent to which the improvement in resistance to oxidative metabolism has improved. In this way, it is determined that the half-life of the parent compound can be extended by up to 100% as the result of deuterium-hydrogen exchange of this type.

Deuterium-hydrogen exchange in a compound of the formula I can also be used to achieve a favorable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

As used herein, the term "modulator" is defined as a compound that binds to and/or inhibits the target with measurable affinity. In certain embodiments, a modulator has an $IC_{50}$ and/or binding constant of greater than about 20 µM, between about 10 µM and 20 µM, or less than about 10 µM. In certain embodiments, a modulator has an $IC_{50}$ and/or binding constant of greater than about 5 µM, between about 1 µM and 5 µM, or less than about 1 µM.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

3. Description of Exemplary Compounds

According to one aspect, the present invention provides a compound of formula I,

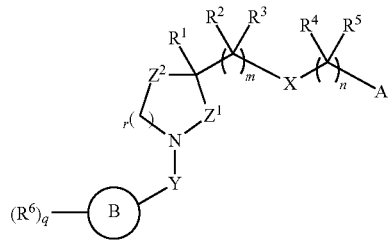

or a pharmaceutically acceptable salt, solvate, hydrate, or polymorph thereof, wherein:
$Z^1$ is C(R)(R), C(O), C(S), or C(NR);
$Z^2$ is C(R)(R), O, S, SO, $SO_2$, or NR;
X is —O—, —S—, —$SO_2$—, —SO—, —C(O)—, —$CO_2$—, —C(O)N(R)—, —NRC(O)—, —NRC(O)N(R)—, —$NRSO_2$—, or —N(R)—; or X is absent;
A is a $C_{1-6}$ aliphatic, $C_{5-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered heteroaryl ring having 1-4 heteroatoms independently selected from nitrogen, oxygen, or sulfur; each of which is optionally substituted;
$R^1$ is —R, halogen, -haloalkyl, —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —$NRSO_2R$, or —N(R)$_2$;
each of $R^2$, $R^3$, $R^4$, and $R^5$, is independently H or $C_{1-6}$ aliphatic;
Y is —$CH_2$—, —O—, —S—, —$SO_2$—, —SO—, —C(O)—, —$CO_2$—, —C(O)N(R)—, —NRC(O)—, —NRC(O)N(R)—, —$NRSO_2$—, or —N(R)—;
Ring B is $C_{5-10}$ aryl or a 5-6 membered heteroaryl ring having 1-4 heteroatoms independently selected from nitrogen, oxygen, or sulfur; each of which is optionally substituted;
each $R^6$ is independently —R, halogen, -haloalkyl, —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —$NRSO_2R$, or —N(R)$_2$;
m is 0, 1, 2, or 3;
n is 0, 1, 2, or 3;
q is 0, 1, 2, or 3;
r is 1 or 2; and
each R is independently hydrogen, $C_{1-6}$ aliphatic, $C_{5-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted; or
two R groups on the same atom are taken together with the atom to which they are attached to form a $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.
In certain embodiments, $Z^1$ is C(R)(R). In certain embodiments, $Z^1$ is $CH_2$. In certain embodiments, $Z^1$ is C(O). In certain embodiments, $Z^1$ is C(S). In certain embodiments, $Z^1$ is C(NR).

In certain embodiments, $Z^2$ is C(R)(R). In certain embodiments, $Z^2$ is $CH_2$. In certain embodiments, $Z^2$ is O. In certain embodiments, $Z^2$ is S. In certain embodiments, $Z^2$ is SO. In certain embodiments, $Z^2$ is $SO_2$. In certain embodiments, $Z^2$ is NR.

In certain embodiments, X is —O—, —S—, —$SO_2$—, —SO—, —C(O)—, —$CO_2$—, —C(O)N(R)—, —NRC(O)—, —NRC(O)N(R)—, —$NRSO_2$—, or —N(R)—.

In certain embodiments, X is —O—, —C(O)—, —$CO_2$—, or —C(O)N(R)—.

In certain embodiments, X is —O—, —C(O)—, —$CO_2$—, or —C(O)NH—. In certain embodiments, X is —O—. In certain embodiments, X is —C(O)—. In certain embodiments, X is —$CO_2$—. In certain embodiments, X is —C(O)NH—.

In certain embodiments, X is absent.

In certain embodiments, A is an optionally substituted $C_{1-6}$ aliphatic.

In certain embodiments, A is methyl, ethyl, n-propyl, i-propyl, n-butyl, s-butyl, t-butyl, straight chain or branched pentyl, or straight chain or branched hexyl; each of which is optionally substituted.

In certain embodiments, A is methyl. In certain embodiments, A is ethyl.

In certain embodiments, A is $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered heteroaryl ring having 1-4 heteroatoms independently selected from nitrogen, oxygen, or sulfur; each of which is optionally substituted.

In certain embodiments, A is phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is optionally substituted.

In certain embodiments, A is selected from the following, each of which is further optionally substituted:

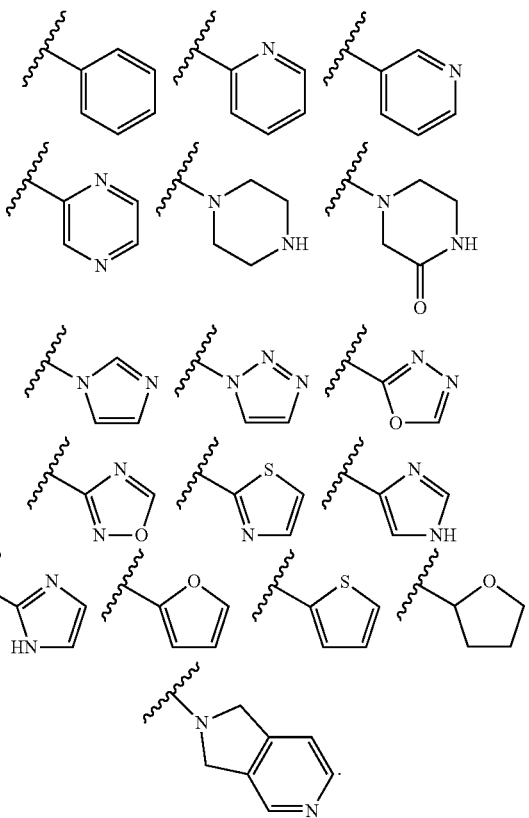

In certain embodiments, A is selected from the following:

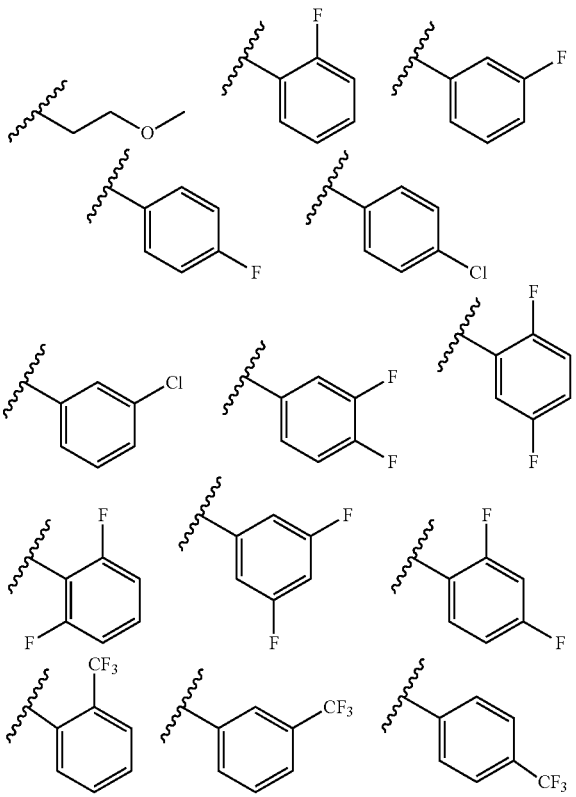

-continued
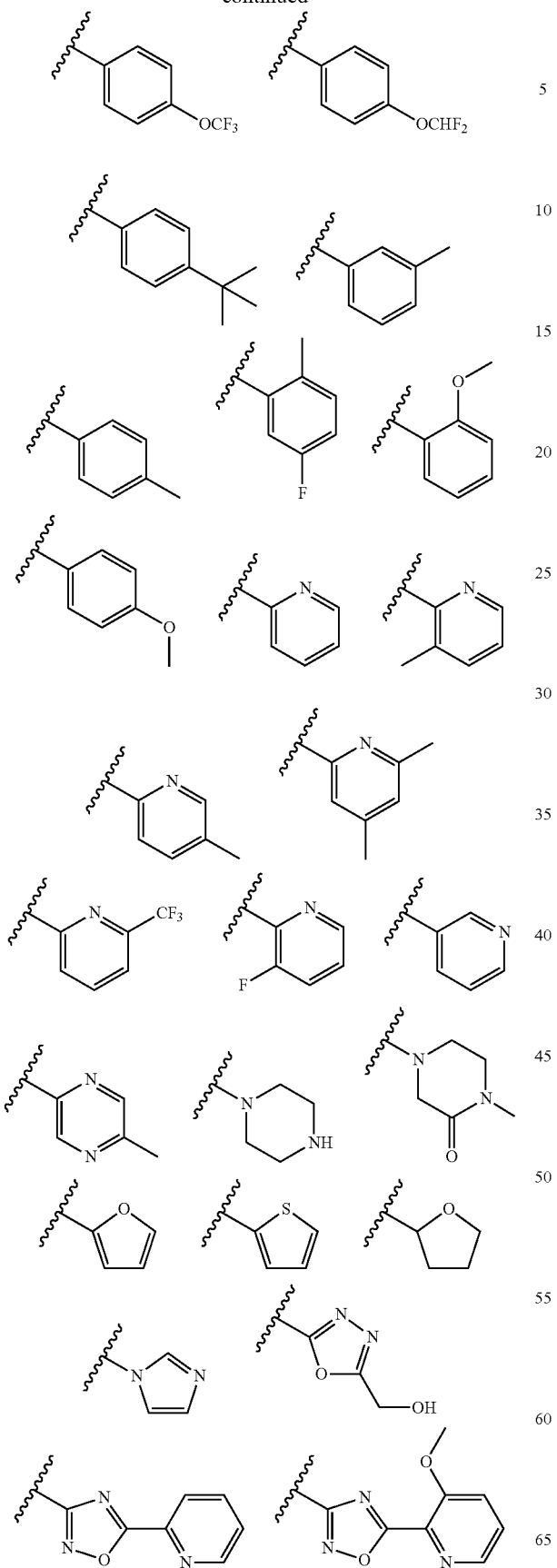
-continued
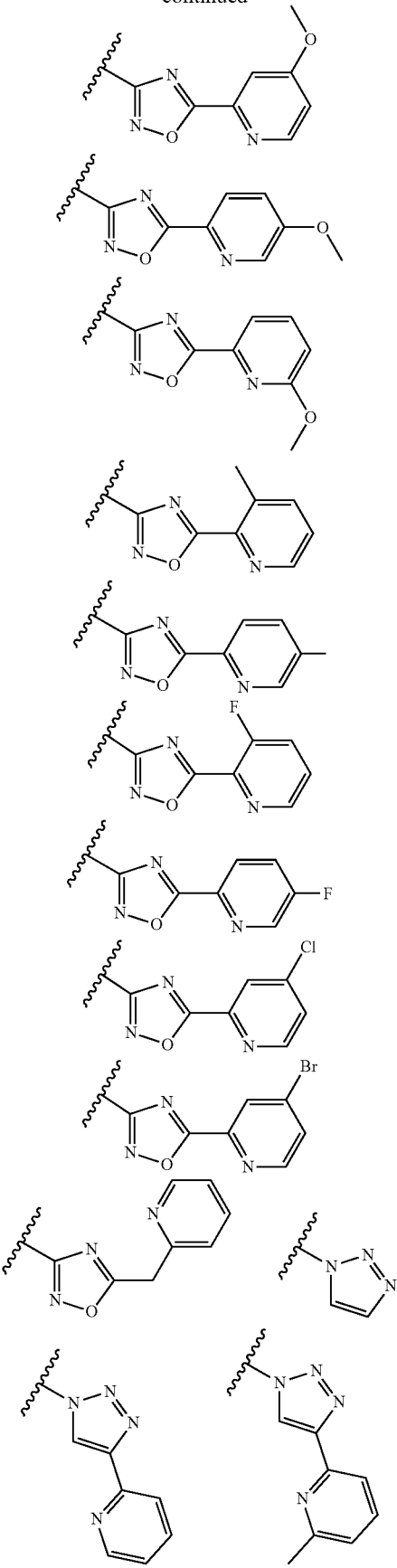

-continued

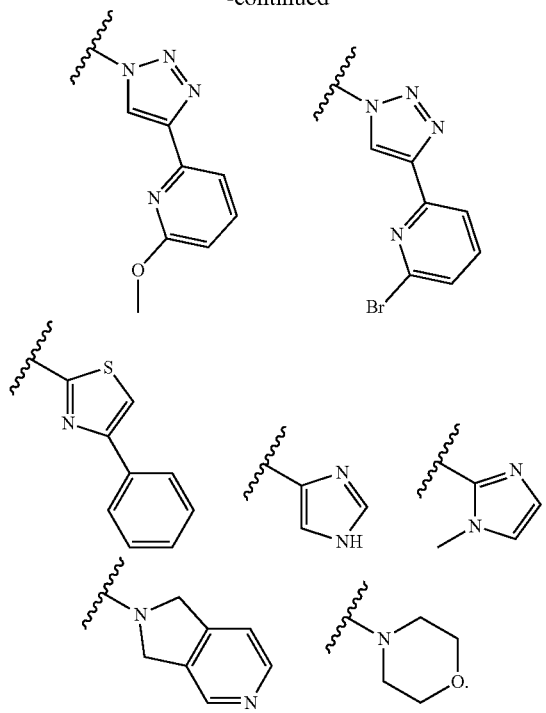

In various embodiments, Ring B is selected from:

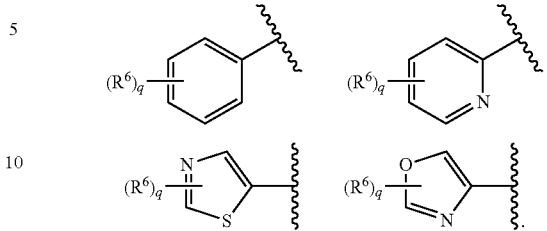

In various embodiments, each $R^6$ is independently —R, halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$.

In various embodiments, each $R^6$ is independently halogen, —OR, —SR, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$. In various embodiments, each $R^6$ is independently halogen, —OR, —SR, —SO$_2$R, —SOR, —NRC(O)R, —NRC(O)N(R)$_2$, —NRSO$_2$R, or —N(R)$_2$. In various embodiments, each $R^6$ is independently halogen, —OR, —SR, —SO$_2$R, or —SOR.

In various embodiments, each $R^6$ is independently halogen. In various embodiments, each $R^6$ is independently —OR. In various embodiments, each $R^6$ is independently —SR. In various embodiments, each $R^6$ is independently —SO$_2$R. In various embodiments, each $R^6$ is independently —SOR.

In various embodiments, each $R^6$ is independently selected from F, Cl, Br, I,

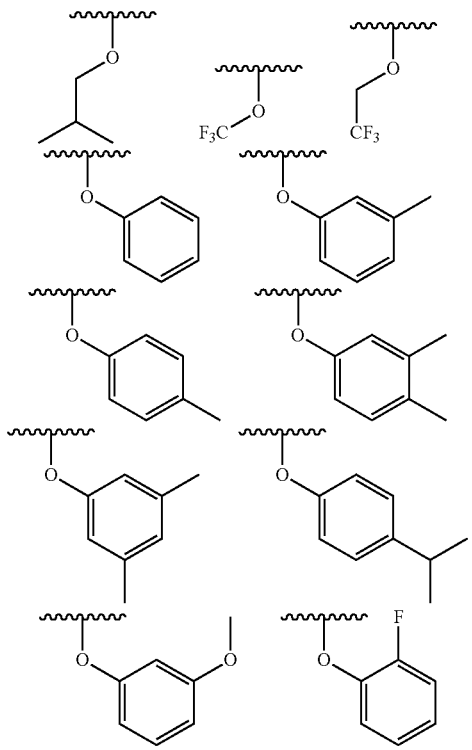

In certain embodiments, $R^1$ is H.

In certain embodiments, $R^1$ is —R, halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$.

In certain embodiments, $R^1$ is $C_{1-6}$ aliphatic, $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted. In certain embodiments, $R^1$ is $C_{1-6}$ aliphatic. In certain embodiments, $R^1$ is methyl, ethyl, n-propyl, i-propyl, n-butyl, s-butyl, t-butyl, straight chain or branched pentyl, or straight chain or branched hexyl; each of which is optionally substituted. In certain embodiments, $R^1$ is methyl.

In certain embodiments, $R^1$ is halogen. In certain embodiments, $R^1$ is F, Cl, Br, or I. In certain embodiments, $R^1$ is F or Cl. In certain embodiments, $R^1$ is F. In certain embodiments, $R^1$ is Cl.

In certain embodiments, $R^1$ is —OR, —SR, or —N(R)$_2$. In certain embodiments, $R^1$ is —OR. In certain embodiments, $R^1$ is —OH.

In various embodiments, each of $R^2$, $R^3$, $R^4$, and $R^5$, is independently H or $C_1$-aliphatic. In various embodiments, each of $R^2$, $R^3$, $R^4$, and $R^5$, is independently H or Me. In various embodiments, $R^2$ is H or $C_{1-6}$ aliphatic. In various embodiments, $R^2$ is H or Me. In various embodiments, $R^3$ is H or $C_{1-6}$ aliphatic. In various embodiments, $R^3$ is H or Me. In various embodiments, $R^4$ is H or $C_{1-6}$ aliphatic. In various embodiments, $R^4$ is H or Me. In various embodiments, $R^5$ is H or $C_{1-6}$ aliphatic. In various embodiments, $R^5$ is H or Me.

In various embodiments, Y is —CH$_2$—.

In various embodiments, Ring B is $C_{5-10}$ aryl.

In various embodiments, Ring B is a 5-6 membered heteroaryl ring having 1-4 heteroatoms independently selected from nitrogen, oxygen, or sulfur.

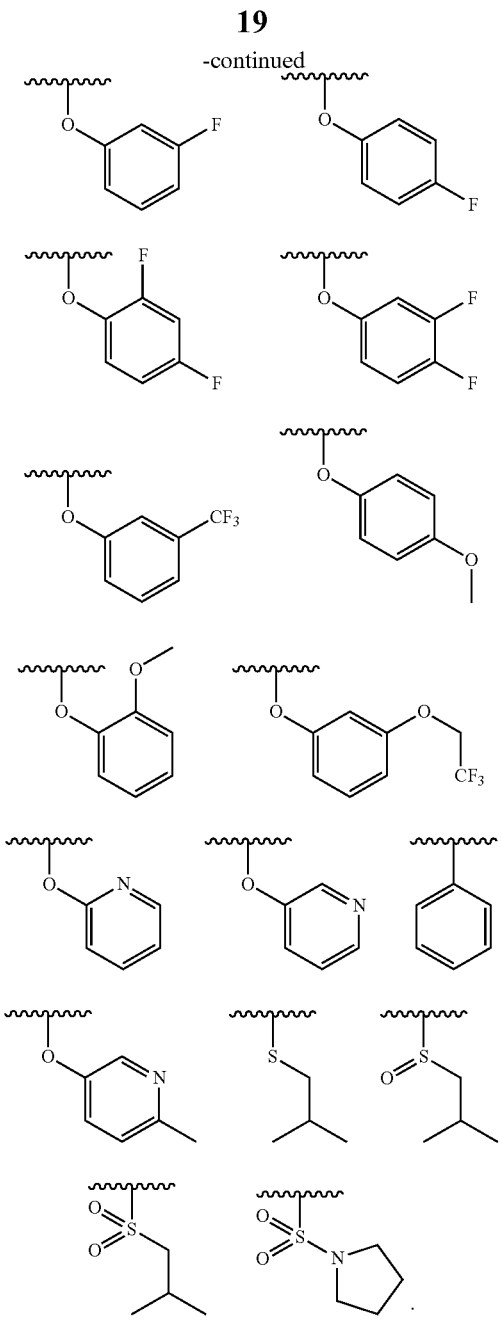

In certain embodiments, m is 0, 1, or 2. In certain embodiments, m is 0. In certain embodiments, m is 1. In certain embodiments, m is 2.

In certain embodiments, n is 0, 1, or 2. In certain embodiments, n is 0. In certain embodiments, n is 1. In certain embodiments, n is 2.

In certain embodiments, q is 0, 1, or 2. In certain embodiments, q is 0. In certain embodiments, q is 1. In certain embodiments, q is 2.

In certain embodiments, r is 1. In certain embodiments, r is 2.

In certain embodiments, each of $Z^1$, $Z^2$, X, A, Y, ring B, $R^1$, $R^2$, $R^3$, $R^4$, $R^5$, $R^6$, m, n, q, and r is as defined above and described in embodiments, classes and subclasses above and herein, singly or in combination.

In certain embodiments, the present invention provides a compound of formula II,

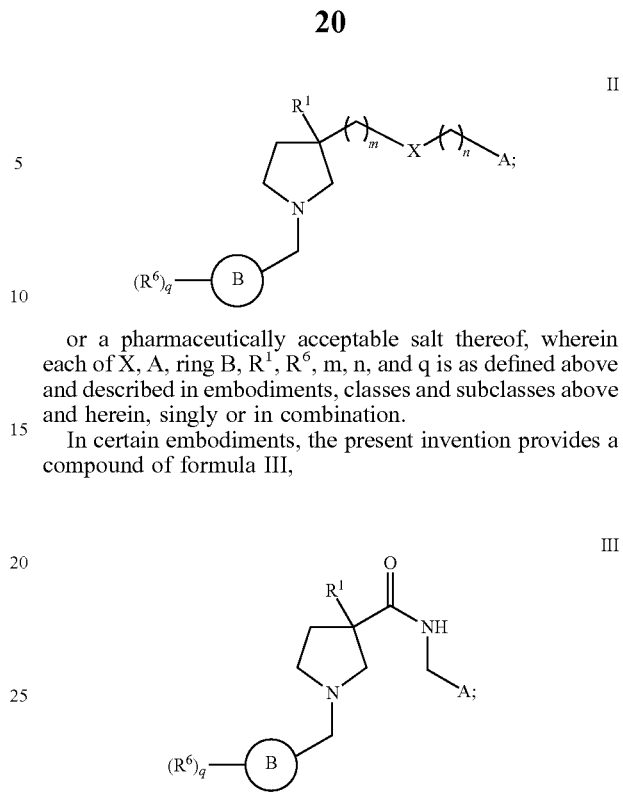

or a pharmaceutically acceptable salt thereof, wherein each of X, A, ring B, $R^1$, $R^6$, m, n, and q is as defined above and described in embodiments, classes and subclasses above and herein, singly or in combination.

In certain embodiments, the present invention provides a compound of formula III,

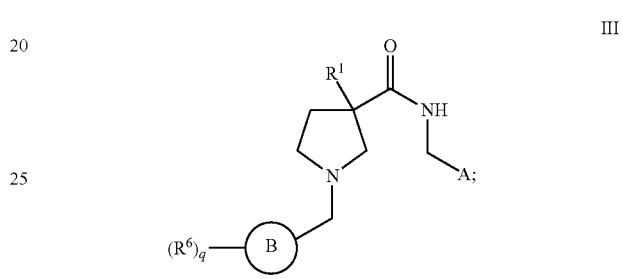

or a pharmaceutically acceptable salt thereof, wherein each of A, ring B, $R^1$, $R^6$, and q is as defined above and described in embodiments, classes and subclasses above and herein, singly or in combination.

In certain embodiments, the present invention provides a compound of formula IV,

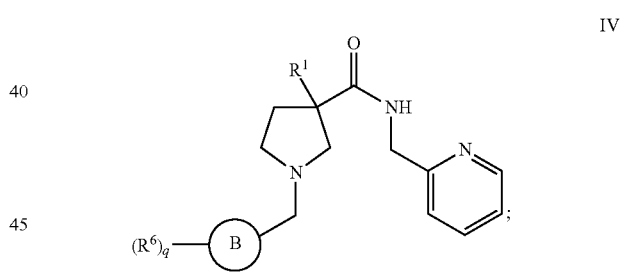

or a pharmaceutically acceptable salt thereof, wherein each of ring B, $R^1$, $R^6$, and q is as defined above and described in embodiments, classes and subclasses above and herein, singly or in combination.

In certain embodiments, the present invention provides a compound of formula V,

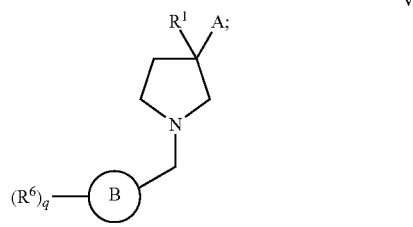

or a pharmaceutically acceptable salt thereof, wherein each of A, ring B, $R^1$, $R^6$, and q is as defined above and described in embodiments, classes and subclasses above and herein, singly or in combination.

In certain embodiments, the present invention provides a compound of formula VI,

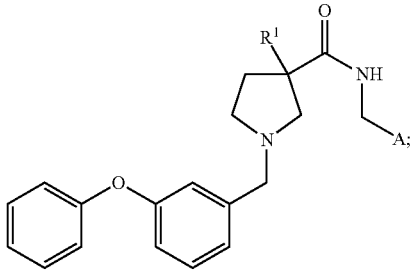

VI or a pharmaceutically acceptable salt thereof, wherein each of A and R¹ is as defined above and described in embodiments, classes and subclasses above and herein, singly or in combination.

In certain embodiments, the present invention provides a compound of formula VII,

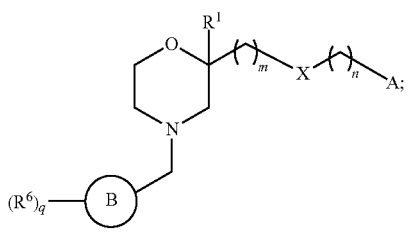

VII or a pharmaceutically acceptable salt thereof, wherein each of X, A, ring B, R¹, R⁶, m, n, and q is as defined above and described in embodiments, classes and subclasses above and herein, singly or in combination.

In certain embodiments, the present invention provides a compound of formula VIII,

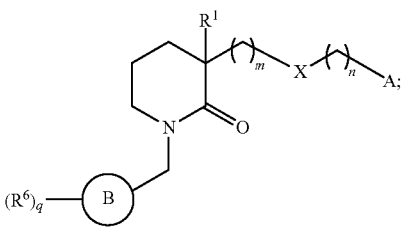

VIII or a pharmaceutically acceptable salt thereof, wherein each of X, A, ring B, R¹, R⁶, m, n, and q is as defined above and described in embodiments, classes and subclasses above and herein, singly or in combination.

In certain embodiments, the invention provides a compound selected from 1-111 from the Examples.

In some embodiments, the present invention provides a compound selected from those depicted above, or a pharmaceutically acceptable salt thereof.

Various structural depictions may show a heteroatom without an attached group, radical, charge, or counterion. Those of ordinary skill in the art are aware that such depictions are meant to indicate that the heteroatom is attached to hydrogen (e.g., 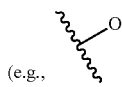)

is understood to be

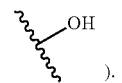

).

In certain embodiments, the compounds of the invention were synthesized in accordance with the schemes provided in the Examples below.

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit or antagonize NaV1.6 in a biological sample or in a patient. In certain embodiments, the amount of compound in compositions of this invention is such that is effective to measurably inhibit or antagonize NaV1.6 in a biological sample or in a patient. In certain embodiments, a composition of this invention is formulated for administration to a patient in need of such composition.

The term "patient" or "subject", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that are used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Compositions of the present invention are administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention include aqueous or oleaginous suspension. These suspensions are formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that are employed are water, Ringer's solution and isotonic sodium chloride solution. In addition, sterile, fixed oils are conventionally employed as a solvent or suspending medium.

For this purpose, any bland fixed oil employed includes synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms are also be used for the purposes of formulation.

Pharmaceutically acceptable compositions of this invention are orally administered in any orally acceptable dosage form. Exemplary oral dosage forms are capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents are optionally also added.

Alternatively, pharmaceutically acceptable compositions of this invention are administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention are also administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches are also used.

For topical applications, provided pharmaceutically acceptable compositions are formulated in a suitable ointment containing the active component suspended or dissolved in one or more carriers. Exemplary carriers for topical administration of compounds of this are mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Pharmaceutically acceptable compositions of this invention are optionally administered by nasal aerosol or inhalation. Such compositions are prepared according to techniques well-known in the art of pharmaceutical formulation and are prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that are optionally combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

In certain embodiments, the invention provides a method for inhibiting or antagonizing NaV1.6 in a patient or in a biological sample comprising the step of administering to said patient or contacting said biological sample with a compound according to the invention.

In certain embodiments, the invention is directed to the use of compounds of the invention and/or physiologically acceptable salts thereof, for modulating or inhibiting/antagonizing NaV1.6. The term "modulation" denotes any change in NaV1.6-mediated signal transduction, which is based on the action of the specific inventive compounds capable to interact with the NaV1.6 target in such a manner that makes recognition, binding and activating possible. The compounds are characterized by such a high affinity to NaV1.6. In certain embodiments, the substances are highly selective for NaV1.6 over most other channels in order to guarantee an exclusive and directed recognition with the single NaV1.6 target. In the context of the present invention, the term "recognition"—without being limited thereto—relates to any type of interaction between the specific compounds and the target, particularly covalent or non-covalent binding or association, such as a covalent bond, hydrophobic/hydrophilic interactions, van der Waals forces, ion pairs, hydrogen bonds, ligand-receptor (enzyme-inhibitor) interactions, and the like. Such association may also encompass the presence of other molecules such as peptides, proteins or nucleotide sequences. The present ion channel interaction is characterized by high affinity, high selectivity and minimal or even lacking cross-reactivity to other target molecules to exclude unhealthy and harmful impacts to the treated subject.

In certain embodiments, the present invention relates to a method for inhibiting or antagonizing NaV1.6, with at least one compound of formula (I) according to the invention and/or physiologically acceptable salts thereof, under conditions such that said NaV1.6 is inhibited/antagonized. In certain embodiments, the system is a cellular system. The cellular system is defined to be any subject provided that the subject comprises cells. Hence, the cellular system can be selected from the group of single cells, cell cultures, tissues, organs and animals. In certain embodiments, the method for modulating NaV1.6 is performed in-vitro. The prior teaching of the present specification concerning the compounds of formula (I), including any embodiments thereof, is valid and applicable without restrictions to the compounds according to formula (I) and their salts when used in the method for inhibiting/antagonizing NaV1.6. The prior teaching of the present specification concerning the compounds of formula (I), including any embodiments thereof, is valid and applicable without restrictions to the compounds according to formula (I) and their salts when used in the method for inhibiting/antagonizing NaV1.6.

Provided compounds are inhibitors/antagonists of NaV1.6 and are therefore useful for treating one or more disorders associated with activity of NaV1.6. Thus, in some embodiments, the present invention provides a method for treating a NaV1.6-mediated disorder comprising the step of administering to a patient in need thereof a compound of the present invention, or pharmaceutically acceptable composition thereof.

In yet another aspect, a method for the treatment or lessening the severity of acute, chronic, neuropathic, or inflammatory pain, arthritis, migrane, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain is provided comprising administering an effective amount of a compound, or a pharmaceutically acceptable composition comprising a compound to a subject in need thereof. In certain embodiments, a method for the treatment or lessening the severity of acute, chronic, neuropathic, or inflammatory pain is provided comprising administering an effective amount of a compound or a pharmaceutically acceptable composition to a subject in need thereof. In certain other embodiments, a method for the treatment or lessening the severity of radicular pain, sciatica, back pain, head pain, or neck pain is provided comprising administering an effective amount of a compound or a pharmaceutically acceptable composition to a subject in need thereof. In still other embodiments, a method for the treatment or lessening the severity of severe or intractable pain, acute pain, postsurgical pain, back pain, tinnitis or cancer pain is provided comprising administering an effective amount of a compound or a pharmaceutically acceptable composition to a subject in need thereof.

The compounds of the present invention are useful in the prophylaxis and treatment of autoimmune and/or inflammatory disorders, including neurodegenerative diseases, such as multiple sclerosis (MS), polyneuritis, multiple neuritis, amyotrophic lateral sclerosis (ALS), Alzheimer's disease or Parkinson's disease.

The present invention furthermore relates to a method of treating a subject suffering from an immunerogulatory abnomality, comprising administering to said subject a compound of formula I in an amount that is effective for treating said immunoregulatory abnormality. The present invention preferably relates to a method wherein the immunoregulatory abnormality is an autoimmune or chronic inflammatory disease selected from the group consisting of: amyotrophic lateral sclerosis (ALS), Alzheimer's disease, Parkinson's disease, systemic lupus erythematosus, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves' ophthalmopathy and asthma. The present invention furthermore relates to a method wherein the immunoregulatory abnormality is bone marrow or organ transplant rejection or graft-versus-host disease. The present invention furthermore relates to a method wherein the immunoregulatory abnormality is selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, 5 Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis *nodosa*, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia *senilis* by preventing epilation or providing hair germination and/or promoting hair generation and hair growth, muscular dystrophy, pyoderma and Sezary's syndrome, Addison's disease, ischemiareperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-C4 release, Behcet's disease, autoimmune hepatitis, primary biliary cirrhosis, sclerosing cholangitis, partial liver resection, 35 acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, and chronic bacterial infection.

In certain embodiments of the present invention an "effective amount" of the compound or pharmaceutically acceptable composition is that amount effective for treating or lessening the severity of a disease or disorder provide supra.

The compounds and compositions, according to the method of the present invention, may be administered using any amount and any route of administration effective for treating or lessening the severity of a disease or disorder provide supra.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form", as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

As described generally above, the compounds of the invention are useful as inhibitors of voltage-gated sodium ion channels. In one embodiment, the compounds and compositions of the invention are inhibitors of one or more of NaV1.1, NaV1.2, NaV1.3, NaV1.4, NaV1.5, NaV1.6, NaV1.7, NaV1.8, or NaV1.9, and thus, without wishing to be bound by any particular theory, the compounds and compositions are particularly useful for treating or lessening the severity of a disease, condition, or disorder where activation or hyperactivity of one or more of NaV1.1, NaV1.2, NaV1.3, NaV1.4, NaV1.5, NaV1.6, NaV1.7, NaV1.8, or NaV1.9 is implicated in the disease, condition, or disorder. When activation or hyperactivity of NaV1.1, NaV1.2, NaV1.3, NaV1.4, NaV1.5, NaV1.6, NaV1.7, NaV1.8, or NaV1.9, is implicated in a particular disease, condition, or disorder, the disease, condition, or disorder may also be referred to as a "NaV1.1, NaV1.2, NaV1.3, NaV1.4, NaV1.5, NaV1.6, NaV1.7, NaV1.8 or NaV1.9-mediated disease, condition or disorder". Accordingly, in another aspect, the present invention provides a method for treating or lessening the severity of a disease, condition, or disorder where activation or hyperactivity of one or more of NaV1.1, NaV1.2, NaV1.3, NaV1.4, NaV1.5, NaV1.6, NaV1.7, NaV1.8, or NaV1.9 is implicated in the disease state.

In certain embodiments, the compounds and compositions of the invention are inhibitors of NaV1.6.

The activity of a compound utilized in this invention as an inhibitor of NaV1.1, NaV1.2, NaV1.3, NaV1.4, NaV1.5, NaV1.6, NaV1.7, NaV1.8, or NaV1.9, may be assayed according to methods described generally in the examples herein, or according to methods available to one of ordinary skill in the art.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated". For example, exemplary additional therapeutic agents include, but are not limited to: nonopioid analgesics (indoles such as Etodolac, Indomethacin, Sulindac, Tolmetin; naphthylalkanones such sa Nabumetone; oxicams such as Piroxicam; para-aminophenol derivatives, such as Acetaminophen; propionic acids such as Fenoprofen, Flurbiprofen, Ibuprofen, Ketoprofen, Naproxen, Naproxen sodium, Oxaprozin; salicylates such as ASS (Aspirin), Choline magnesium trisalicylate, Diflunisal; fenamates such as meclofenamic acid, Mefenamic acid; and pyrazoles such as Phenylbutazone); or opioid (narcotic) agonists (such as Codeine, Fentanyl, Hydromorphone, Levorphanol, Meperidine, Methadone, Morphine, Oxycodone, Oxymorphone, Propoxyphene, Buprenorphine, Butorphanol, Dezocine, Nalbuphine, and Pentazocine). Additionally, nondrug analgesic approaches may be utilized in conjunction with administration of one or more compounds of the invention. For example, anesthesiologic (intraspinal infusion, neural blocade), neurosurgical (neurolysis of CNS pathways), neurostimulatory (transcutaneous electrical nerve stimulation, dorsal column stimulation), physiatric (physical therapy, orthotic devices, diathermy), or psychologic (cognitive methods-hypnosis, biofeedback, or behavioral methods) approaches may also be utilized. Additional appropriate therapeutic agents or approaches are described generally in The Merck Manual, Seventeenth Edition, Ed. Mark H. Beers and Robert Berkow, Merck Research Laboratories, 1999, and the Food and Drug Administration website, www.fda.gov, the entire contents of which are hereby incorporated by reference.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition.

Another aspect of the invention relates to inhibiting NaV1.6 activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of NaV1.6 activity in a biological sample is useful for a variety of purposes that are known to one of skill in the art. Examples of such purposes include, but are not limited to, the study of sodium ion channels in biological and pathological phenomena; and the comparative evaluation of new sodium ion channel inhibitors.

Compounds of formula (I) and/or a physiologically acceptable salt thereof can furthermore be employed as intermediate for the preparation of further medicament active ingredients. The medicament is preferably prepared in a non-chemical manner, e.g. by combining the active ingredient with at least one solid, fluid and/or semi-fluid carrier or excipient, and optionally in conjunction with a single or more other active substances in an appropriate dosage form.

The compounds of formula (I) according to the invention can be administered before or following an onset of disease once or several times acting as therapy. The aforementioned compounds and medical products of the inventive use are particularly used for the therapeutic treatment. A therapeutically relevant effect relieves to some extent one or more symptoms of a disorder, or returns to normality, either partially or completely, one or more physiological or biochemical parameters associated with or causative of a disease or pathological condition. Monitoring is considered as a kind of treatment provided that the compounds are administered in distinct intervals, e.g. in order to boost the response and eradicate the pathogens and/or symptoms of the disease completely. Either the identical compound or different compounds can be applied. The methods of the invention can also be used to reduce the likelihood of developing a disorder or even prevent the initiation of disorders associated with Nav1.6 activity in advance or to treat the arising and continuing symptoms.

In the meaning of the invention, prophylactic treatment is advisable if the subject possesses any preconditions for the aforementioned physiological or pathological conditions, such as a familial disposition, a genetic defect, or a previously incurred disease.

The invention furthermore relates to a medicament comprising at least one compound according to the invention and/or pharmaceutically usable derivatives, salts, solvates and stereoisomers thereof, including mixtures thereof in all ratios. In certain embodiments, the invention relates to a medicament comprising at least one compound according to the invention and/or physiologically acceptable salts thereof.

A "medicament" in the meaning of the invention is any agent in the field of medicine, which comprises one or more compounds of formula (I) or preparations thereof (e.g. a pharmaceutical composition or pharmaceutical formulation) and can be used in prophylaxis, therapy, follow-up or aftercare of patients who suffer from diseases, which are associated with Nav1.6 activity, in such a way that a pathogenic modification of their overall condition or of the condition of particular regions of the organism could establish at least temporarily.

In various embodiments, the active ingredient may be administered alone or in combination with other treatments. A synergistic effect may be achieved by using more than one compound in the pharmaceutical composition, i.e. the compound of formula (I) is combined with at least another agent as active ingredient, which is either another compound of formula (I) or a compound of different structural scaffold. The active ingredients can be used either simultaneously or sequentially.

Included herein are methods of treatment in which at least one chemical entity provided herein is administered in combination with an anti-inflammatory agent. Anti-inflammatory agents include but are not limited to NSAIDs, non-specific and COX-2 specific cyclooxygenase enzyme inhibitors, gold compounds, corticosteroids, methotrexate, tumor necrosis factor (TNF) antagonists, immunosuppressants and methotrexate.

Examples of NSAIDs include, but are not limited to, ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors such as celecoxib, valdecoxib, lumiracoxib and/or etoricoxib.

In some embodiments, the anti-inflammatory agent is a salicylate. Salicylates include by are not limited to acetylsalicylic acid or aspirin, sodium salicylate, and choline and magnesium salicylates.

The anti-inflammatory agent may also be a corticosteroid. For example, the corticosteroid may be cortisone, dexamethasone, methylprednisolone, prednisolone, prednisolone sodium phosphate, or prednisone.

In additional embodiments the anti-inflammatory agent is a gold compound such as gold sodium thiomalate or auranofin.

The invention also includes embodiments in which the anti-inflammatory agent is a metabolic inhibitor such as a dihydrofolate reductase inhibitor, such as methotrexate or a dihydroorotate dehydrogenase inhibitor, such as leflunomide.

Other embodiments of the invention pertain to combinations in which at least one anti-inflammatory compound is an anti-monoclonal antibody (such as eculizumab or pexelizumab), a TNF antagonist, such as entanercept, or infliximab, which is an anti-TNF alpha monoclonal antibody.

Still other embodiments of the invention pertain to combinations in which at least one active agent is an immunosuppressant compound such as an immunosuppressant compound chosen from methotrexate, leflunomide, cyclosporine, tacrolimus, azathioprine, and mycophenolate mofetil.

The disclosed compounds of the formula I can be administered in combination with other known therapeutic agents, including anticancer agents. As used here, the term "anti-cancer agent" relates to any agent which is administered to a patient with cancer for the purposes of treating the cancer.

The anti-cancer treatment defined above may be applied as a monotherapy or may involve, in addition to the herein disclosed compounds of formula I, conventional surgery or radiotherapy or medicinal therapy. Such medicinal therapy, e.g. a chemotherapy or a targeted therapy, may include one or more, but preferably one, of the following anti-tumor agents:

Alkylating agents: such as altretamine, bendamustine, busulfan, carmustine, chlorambucil, chlormethine, cyclophosphamide, dacarbazine, ifosfamide, improsulfan, tosilate, lomustine, melphalan, mitobronitol, mitolactol, nimustine, ranimustine, temozolomide, thiotepa, treosulfan, mechloretamine, carboquone; apaziquone, fotemustine, glufosfamide, palifosfamide, pipobroman, trofosfamide, uramustine, TH-302[4], VAL-083[4];

Platinum Compounds: such as carboplatin, cisplatin, eptaplatin, miriplatine hydrate, oxaliplatin, lobaplatin, nedaplatin, picoplatin, satraplatin; lobaplatin, nedaplatin, picoplatin, satraplatin;

DNA altering agents: such as amrubicin, bisantrene, decitabine, mitoxantrone, procarbazine, trabectedin, clofarabine; amsacrine, brostallicin, pixantrone, laromustine[1,3];

Topoisomerase Inhibitors: such as etoposide, irinotecan, razoxane, sobuzoxane, teniposide, topotecan; amonafide, belotecan, elliptinium acetate, voreloxin;

Microtubule modifiers: such as cabazitaxel, docetaxel, eribulin, ixabepilone, paclitaxel, vinblastine, vincristine, vinorelbine, vindesine, vinflunine; fosbretabulin, tesetaxel;

Antimetabolites: such as asparaginase[3], azacitidine, calcium levofolinate, capecitabine, cladribine, cytarabine, enocitabine, floxuridine, fludarabine, fluorouracil, gemcitabine, mercaptopurine, methotrexate, nelarabine, pemetrexed, pralatrexate, azathioprine, thioguanine, carmofur; doxifluridine, elacytarabine, raltitrexed, sapacitabine, tegafur[2,3], trimetrexate;

Anticancer antibiotics: such as bleomycin, dactinomycin, doxorubicin, epirubicin, idarubicin, levamisole, miltefosine, mitomycin C, romidepsin, streptozocin, valrubicin, zinostatin, zorubicin, daunorubicin, plicamycin; aclarubicin, peplomycin, pirarubicin;

Hormones/Antagonists: such as abarelix, abiraterone, bicalutamide, buserelin, calusterone, chlorotrianisene, degarelix, dexamethasone, estradiol, fluocortolone fluoxymesterone, flutamide, fulvestrant, goserelin, histrelin, leuprorelin, megestrol, mitotane, nafarelin, nandrolone, nilutamide, octreotide, prednisolone, raloxifene, tamoxifen, thyrotropin alfa, toremifene, trilostane, triptorelin, diethylstilbestrol; acolbifene, danazol, deslorelin, epitiostanol, orteronel, enzalutamide[1,3];

Aromatase inhibitors: such as aminoglutethimide, anastrozole, exemestane, fadrozole, letrozole, testolactone; formestane;

Small molecule kinase inhibitors: such as crizotinib, dasatinib, erlotinib, imatinib, lapatinib, nilotinib, pazopanib, regorafenib, ruxolitinib, sorafenib, sunitinib, vandetanib, vemurafenib, bosutinib, gefitinib, axitinib; afatinib, alisertib, dabrafenib, dacomitinib, dinaciclib, dovitinib, enzastaurin, nintedanib, lenvatinib, linifanib, linsitinib, masitinib, midostaurin, motesanib, neratinib, orantinib, perifosine, ponatinib, radotinib, rigosertib, tipifarnib, tivantinib, tivozanib, trametinib, pimasertib, brivanib alaninate, cediranib, apatinib[4], cabozantinib S-malate[1,3], ibrutinib[1,3], icotinib[4], buparlisib[2], cipatinib[4], cobimetinib[1,3], idelalisib[1,3], fedratinib[1], XL-647[4];

Photosensitizers: such as methoxsalen[3]; porfimer sodium, talaporfin, temoporfin;

Antibodies: such as alemtuzumab, besilesomab, brentuximab vedotin, cetuximab, denosumab, ipilimumab, ofatumumab, panitumumab, rituximab, tositumomab, trastuzumab, bevacizumab, pertuzumab[2,3]; catumaxomab, elotuzumab, epratuzumab, farletuzumab, mogamulizumab, necitumumab, nimotuzumab, obinutuzumab, ocaratuzumab, oregovomab, ramucirumab, rilotumumab, siltuximab, tocilizumab, zalutumumab, zanolimumab, matuzumab, dalotuzumab[1,2,3], onartuzumab[1,3], racotumomab[1], tabalumab[1,3], EMD-525797[4], nivolumab[1,3];

Cytokines: such as aldesleukin, interferon alfa[2], interferon alfa2a[3], interferon alfa2b[2,3]; celmoleukin, tasonermin, teceleukin, oprelvekin[1,3], recombinant interferon beta-1a[4];

Drug Conjugates: such as denileukin diftitox, ibritumomab tiuxetan, iobenguane I123, prednimustine, trastuzumab emtansine, estramustine, gemtuzumab, ozogamicin, aflibercept; cintredekin besudotox, edotreotide, inotuzumab ozogamicin, naptumomab estafenatox, oportuzumab monatox, technetium (99mTc) arcitumomab[1,3], vintafolide[1,3];

Vaccines: such as sipuleucel[3]; vitespen[3], emepepimut-S[3], oncoVAX[4], rindopepimut[3], troVax[4], MGN-1601[4], MGN-1703[4]; and Miscellaneous: alitretinoin, bexarotene, bortezomib, everolimus, ibandronic acid, imiquimod, lenalidomide, lentinan, metirosine, mifamurtide, pamidronic acid, pegaspargase, pentostatin, sipuleucel[3], sizofiran, tamibarotene, temsirolimus, thalidomide, tretinoin, vismodegib, zoledronic acid, vorinostat; celecoxib, cilengitide, entinostat, etanidazole, ganetespib, idronoxil, iniparib, ixazomib, lonidamine, nimorazole, panobinostat, peretinoin, plitidepsin, pomalidomide, procodazol, ridaforolimus, tasquinimod, telotristat, thymalfasin, tirapazamine, tosedostat, trabedersen, ubenimex, valspodar, gendicine[4], picibanil[4], reolysin[4], retaspimycin hydrochloride[1,3], trebananib[2,3], virulizin[4], carfilzomib[1,3], endostatin[4], immucothel[4], belinostat[3], MGN-1703[4].

(¹Prop. INN (Proposed International Nonproprietary Name); ²Rec. INN (Recommended International Nonproprietary Names); ³USAN (United States Adopted Name); ⁴no INN).

In another aspect, the invention provides for a kit consisting of separate packs of an effective amount of a compound according to the invention and/or pharmaceutically acceptable salts, derivatives, solvates and stereoisomers thereof, including mixtures thereof in all ratios, and optionally, an effective amount of a further active ingredient. The kit comprises suitable containers, such as boxes, individual bottles, bags or ampoules. The kit may, for example, comprise separate ampoules, each containing an effective amount of a compound according to the invention and/or pharmaceutically acceptable salts, derivatives, solvates and stereoisomers thereof, including mixtures thereof in all ratios, and an effective amount of a further active ingredient in dissolved or lyophilized form.

As used herein, the terms "treatment," "treat," and "treating" refer to reversing, alleviating, delaying the onset of, or inhibiting the progress of a disease or disorder, or one or more symptoms thereof, as described herein. In some embodiments, treatment is administered after one or more symptoms have developed. In other embodiments, treatment is administered in the absence of symptoms. For example, treatment is administered to a susceptible individual prior to the onset of symptoms (e.g., in light of a history of symptoms and/or in light of genetic or other susceptibility factors). Treatment is also continued after symptoms have resolved, for example to prevent or delay their recurrence.

The compounds and compositions, according to the method of the present invention, are administered using any amount and any route of administration effective for treating or lessening the severity of a disorder provided above. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention are administered orally or parenterally at dosage levels of about 0.01 mg/kg to about 100 mg/kg and preferably from about 1 mg/kg to about 50 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms optionally contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions are formulated according to the known art using suitable dispersing or wetting agents and suspending agents. The sterile injectable preparation are also a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This is accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and *acacia*, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form also optionally comprises buffering agents.

Solid compositions of a similar type are also employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type are also employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms also comprise, as is normal practice, additional substances other than inert diluents, e.g., tableting lubricants and other tableting aids such a magnesium stearate and microcrystalline cellulose. In the case of capsules, tablets and pills, the dosage forms optionally also comprise buffering agents. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting Nav1.6 activity in a biological sample comprising the step of contacting said biological sample with a compound of this invention, or a composition comprising said compound.

According to another embodiment, the invention relates to a method of inhibiting Nav1.6 activity in a biological sample in a positive manner, comprising the step of contacting said biological sample with a compound of this invention, or a composition comprising said compound.

The compounds of the invention can be applied either themselves and/or in combination with physical measurements for diagnostics of treatment effectiveness. Pharmaceutical compositions containing said compounds and the use of said compounds to treat Nav1.6-mediated conditions is a promising, novel approach for a broad spectrum of therapies causing a direct and immediate improvement in the state of health, whether in human or animal. The orally bioavailable and active new chemical entities of the invention improve convenience for patients and compliance for physicians.

The compounds of formula (I), their salts, isomers, tautomers, enantiomeric forms, diastereomers, racemates, derivatives, prodrugs and/or metabolites are characterized by a high specificity and stability, low manufacturing costs and convenient handling. These features form the basis for a reproducible action, wherein the lack of cross-reactivity is included, and for a reliable and safe interaction with the target structure.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

The symbols and conventions used in the following descriptions of processes, schemes, and examples are consistent with those used in the contemporary scientific literature, for example, the Journal of the American Chemical Society or the Journal of Biological Chemistry.

Unless otherwise indicated, all temperatures are expressed in ° C. (degrees Centigrade). All reactions were conducted at room temperature unless otherwise noted. All compounds of the present invention were synthesized by processes developed by the inventors.

$^1$H-NMR spectra were recorded on a Bruker Avance III 400 MHz. Chemical shifts are expressed in parts per million (ppm, δ units). Coupling constants are in units of Hertz (Hz). Splitting patterns describe apparent multiplicities and are designated as s (singlet), d (doublet), t (triplet), q (quartet), m (multiplet), or br (broad).

Mass spectra were obtained on Agilent 1200 Series mass spectrometers from Agilent technologies, using either Atmospheric Chemical Ionization (APCI) or Electrospray Ionization (ESI). Column: XBridge C8, 3.5 μm, 4.6×50 mm; Solvent A: water+0.1% TFA; Solvent B: CAN; Flow: 2 ml/min; Gradient: 0 min: 5% B, 8 min: 100% B, 8.1 min: 100% B, 8.5 min: 5% B, 10 min 5% B.

HPLC data were obtained using Agilent 1100 series HPLC from Agilent technologies using XBridge column (C8, 3.5 μm, 4.6×50 mm). Solvent A: water+0.1% TFA; Solvent B: ACN; Flow: 2 ml/min; Gradient: 0 min: 5% B, 8 min: 100% B, 8.1 min: 100% B, 8.5 min: 5% B, 10 min 5% B.

The microwave reactions were conducted using Biotage Initiator Microwave Synthesizer using standard protocols that are known in the art.

Some abbreviations that may appear in this application are as follows:

| | |
|---|---|
| δ | chemical shift |
| d | deuterium or doublet |
| dd | doublet of doublets |
| DCM | dichloromethane |
| DMF | dimethylformamide |
| DMSO | dimethylsulfoxide |
| THF | tetrhydrofuran |
| eq. | equivalent |
| h | hour |
| $^1$H | proton |
| HPLC | high pressure liquid chromatography |
| J | coupling constant |
| LC | liquid chromatography |
| m | multiplet |
| M | molecular ion |
| MHz | Megahertz |
| min | minute |
| mL | milliliter |
| MS | mass spectrometry |
| m/z | mass-to-charge ratio |
| NMR | nuclear magnetic resonance |
| RBF | Round Bottom Flask |
| RT | room temperature |
| s | singlet |
| TLC | thin layer chromatography |
| UV | ultraviolet |

Compound numbers utilized in the Examples below correspond to compound numbers set forth supra.

EXAMPLES

Synthetic Intermediates

Intermediate 1: 3-[(Pyridin-2-ylmethyl)-carbamoyl]-pyrrolidine-1-carboxylic acid tert-butyl ester

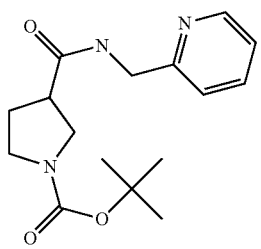 [SMILES: CC(C)(C)OC(=O)N1CCC(C(=O)NCc2ccccn2)C1]

Pyrrolidine-1,3-dicarboxylic acid 1-tert-butyl ester (2.50 g; 11.61 mmol; 1.00 eq.) was dissolved in DCM (25.00 ml; 10.00 V), and 3-Pyridin-2-yl-methylamine (1.26 g; 11.61 mmol; 1.00 eq.) and triethylamine (4.52 ml; 34.84 mmol; 3.00 eq.) were added. The reaction mixture was cooled to 0° C. and to it was added 2,4,6-Tripropyl-[1,3,5,2,4,6]trioxatriphosphinane 2,4,6-trioxide (5.54 g; 17.42 mmol; 1.50 eq.). The reaction mixture was stirred for 12 h at room temperature and then quenched with ice-water. The organic layer was concentrated under reduced pressure to provide the crude product. The product was purified by silica gel column chromatography to provide 3-[(Pyridin-2-ylmethyl)-carbamoyl]-pyrrolidine-1-carboxylic acid tert-butyl ester (3.40 g; 10.91 mmol; 93.9%; brown gum). $^1$H NMR (CDCl$_3$) δ 8.55 (d, J=4.56 Hz, 1H), 7.71 (t, J=7.60 Hz, 1H), 7.30-7.23 (m, 2H), 7.03-7.01 (m, 1H), 4.59 (d, J=4.76 Hz, 2H), 3.64-3.50 (m, 3H), 3.37-3.33 (m, 1H), 3.00-2.98 (m, 1H), 2.17-2.12 (m, 2H), 1.46 (s, 9H).

Intermediate 2: Pyrrolidine-3-carboxylic acid (pyridin-2-ylmethyl)-amide hydrochloride

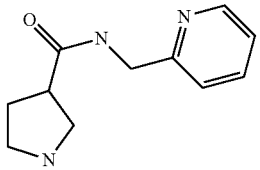 [SMILES: O=C(NCc1ccccn1)C1CCNC1]

The N-protected amide 3-[(Pyridin-2-ylmethyl)-carbamoyl]-pyrrolidine-1-carboxylic acid tert-butyl ester (Intermediate 1, 3.40 g; 10.91 mmol; 1.00 eq.) was stirred with 4M HCl dioxane (10.00 ml; 40.00 mmol; 3.67 eq.) at 0° C. for 3 h. The reaction mixture was concentrated under reduced pressure and purified by recrystallization using dichloromethane-diethylether to afford Pyrrolidine-3-carboxylic acid (pyridin-2-ylmethyl)-amide hydrochloride (2.60 g; 10.54 mmol; 96.6%; off-white solid). $^1$H NMR (DMSO-d$_6$) δ 9.29 (br s, 1H), 9.07-9.04 (m, 2H), 8.69 (d, J=4.32 Hz, 1H), 8.21 (t, J=7.88 Hz, 1H), 7.67 (d, J=7.32 Hz, 2H), 4.55 (d, J=5.68 Hz, 2H), 3.37-3.34 (m, 1H), 3.28-3.14 (m, 4H), 2.23-2.14 (m, 1H), 2.02-1.94 (m, 1H).

Intermediate 3: 3-Fluoro-3-[(pyridin-2-ylmethyl)-carbamoyl]-pyrrolidine-1-carboxylic acid tert-butyl ester

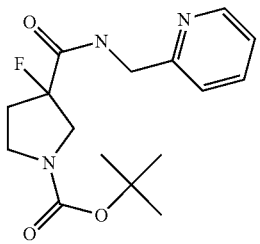 [SMILES: CC(C)(C)OC(=O)N1CCC(F)(C(=O)NCc2ccccn2)C1]

3-Fluoro-pyrrolidine-1,3-dicarboxylic acid 1-tert-butyl ester (Enamine, 0.10 g; 0.41 mmol; 1.00 eq.) was dissolved in DCM (2.00 ml; 20.00 V), and to it was added 3-Pyridin-2-yl-methylamine (0.04 g; 0.41 mmol; 1.00 eq.) and triethylamine (0.16 ml; 1.22 mmol; 3.00 eq.). The reaction mixture was cooled to 0° C. and 2,4,6-Tripropyl-[1,3,5,2,4,6]trioxatriphosphinane 2,4,6-trioxide (0.39 g; 0.61 mmol; 1.50 eq.) was added. The reaction mixture was stirred for 12 h at room temperature and quenched with ice-water. The organic layer was concentrated under reduced pressure to provide crude product, which was purified by Silica gel column chromatography to provide 3-Fluoro-3-[(pyridin-2-ylmethyl)-carbamoyl]-pyrrolidine-1-carboxylic acid tert-butyl ester (0.13 g; 0.40 mmol; 97.6%; off-white gum). ¹H NMR (CDCl₃) δ 8.59 (d, J=4.72 Hz, 1H), 7.92 (br s, 1H), 7.79-7.75 (m, 1H), 7.35-7.29 (m, 2H), 4.65 (d, J=4.68 Hz, 2H), 4.14-3.66 (m, 3H), 3.58-3.51 (m, 1H), 2.60-2.47 (m, 1H), 2.29-2.18 (m, 1H), 1.48 (s, 9H).

Intermediate 4: 3-Fluoro-pyrrolidine-3-carboxylic acid (pyridin-2-ylmethyl)-amide dihydrochloride

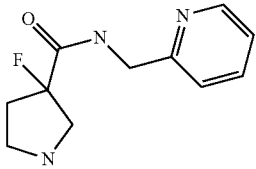 [SMILES: O=C(NCc1ccccn1)C1(F)CCNC1]

3-Fluoro-3-[(pyridin-2-ylmethyl)-carbamoyl]-pyrrolidine-1-carboxylic acid tert-butyl ester (Intermediate 3, 130.00 mg; 0.39 mmol; 1.00 eq.) was stirred with 4M HCl n dioxane (1.00 ml; 4.00 mmol; 10.15 eq.) at 0° C. for 3 h. The reaction mixture was concentrated under reduced pressure and purified by recrystallization using dichloromethane-diethylether to afford 3-Fluoro-pyrrolidine-3-carboxylic acid (pyridin-2-ylmethyl)-amide dihydrochloride (90.00 mg; 0.30 mmol; 76.4%; off-white solid). ¹H NMR (DMSO-d₆) δ 10.02 (br s, 2H), 9.37 (br s, 1H), 8.74-8.73 (m, 1H), 8.30 (t, J=7.72 Hz, 1H), 7.74 (d, J=7.68 Hz, 2H), 4.73-4.62 (m, 2H), 3.75-3.56 (m, 2H), 3.54-3.29 (m, 3H), 2.50-2.36 (m, 2H).

Intermediate 5: 3-Methyl-3-[(pyridin-2-ylmethyl)-carbamoyl]-pyrrolidine-1-carboxylic acid tert-butyl ester

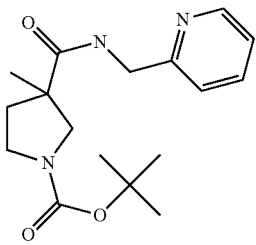 [SMILES: CC(C)(C)OC(=O)N1CCC(C)(C(=O)NCc2ccccn2)C1]

3-Methyl-pyrrolidine-1,3-dicarboxylic acid 1-tert-butyl ester (Enamine, 2.50 g; 10.58 mmol; 1.00 eq.) was dissolved in DCM (25.00 ml; 10.00 V), and 3-Pyridin-2-yl-methyl-amine (1.17 g; 10.58 mmol; 1.00 eq.) and triethylamine (4.12 ml; 31.73 mmol; 3.00 eq.) were added. The reaction mixture was cooled to 0° C. and 2,4,6-Tripropyl-[1,3,5,2,4,6]trioxatriphosphinane 2,4,6-trioxide (10.10 g; 15.87 mmol; 1.50 eq.) was added. The reaction mixture was stirred for 12 h at room temperature and then quenched with ice-water. The organic layer was concentrated under reduced pressure to give crude product, which was purified by silica gel column chromatography to provide 3-Methyl-3-[(pyridin-2-ylmethyl)-carbamoyl]-pyrrolidine-1-carboxylic acid tert-butyl ester (3.30 g; 10.27 mmol; 97.1%; Off white gum) ¹H NMR (CDCl₃) δ 8.53 (d, J=4.56 Hz, 1H), 7.70-7.60 (m, 1H), 7.26-7.22 (m, 2H), 4.56 (d, J=4.64 Hz, 2H), 3.73 (d, J=10.96 Hz, 1H), 3.53-3.43 (m, 2H), 3.36-3.24 (m, 1H), 2.36-2.29 (m, 1H), 1.83-1.80 (m, 1H), 1.46 (s, 9H), 1.39 (s, 3H).

Intermediate 6: Methyl-pyrrolidine-3-carboxylic acid (pyridin-2-ylmethyl)-amide dihydrochloride

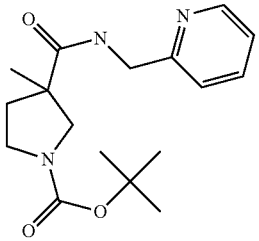 [SMILES: CC(C)(C)OC(=O)N1CCC(C)(C(=O)NCc2ccccn2)C1]

The N-protected amide 3-Methyl-3-[(pyridin-2-ylmethyl)-carbamoyl]-pyrrolidine-1-carboxylic acid tert-butyl ester (Intermediate 5, 3.40 g; 10.54 mmol; 1.00 eq.) was stirred with 4M HCl in dioxane (15.00 ml; 60.00 mmol; 5.69 eq.) at 0° C. for 3 h. The reaction mixture was concentrated under reduced pressure and purified by recrystallization using dichloromethane-diethylether to afford 3-Methyl-pyrrolidine-3-carboxylic acid (pyridin-2-ylmethyl)-amide dihydrochloride (3.00 g; 10.49 mmol; 99.6%). ¹H NMR (DMSO-d₆) δ 9.60 (br s, 1H), 9.29 (br s, 1H), 9.03 (t, J=5.48 Hz, 1H), 8.75 (d, J=4.96 Hz, 1H), 8.36 (t, J=7.52 Hz, 1H), 7.80-7.76 (m, 2H), 4.61 (d, J=5.60 Hz, 2H), 3.60-3.56 (m, 1H), 3.28-3.23 (m, 1H), 3.15-3.09 (m, 1H), 2.99-2.93 (m, 1H), 2.37-2.30 (m, 1H), 1.90-1.83 (m, 1H), 1.40 (s, 3H).

Intermediate 7: 3-Hydroxymethyl-pyrrolidine-1-carboxylic acid tert-butyl ester

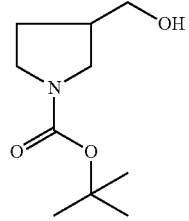

3-Formyl-pyrrolidine-1-carboxylic acid tert-butyl ester (3 g, 15.0 mmol) was taken in methanol (50 mL) and sodium borohydride (0.8 g, 22.5 mmol) was added in portions at room temperature and stirred for 1 h. The reaction mixture was concentrated under reduced pressure and the resulting residue was purified by column chromatography (pet ether/ethyl acetate 20%) to provide the titled compound (66%, 2 g, colorless liquid). ¹H NMR (DMSO-d₆): δ 4.63-4.64 (m, 1H), 3.20-3.37 (m, 4H), 2.92-3.18 (m, 2H), 2.19-2.50 (m, 1H), 1.50-1.98 (m, 2H), 1.38 (s, 9H).

Intermediate 8: 3-Methanesulfonyloxymethyl-pyrrolidine-1-carboxylic acid tert-butyl ester

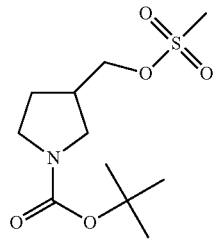 [SMILES: CC(C)(C)OC(=O)N1CCC(COS(C)(=O)=O)C1]

3-Hydroxymethyl-pyrrolidine-1-carboxylic acid tert-butyl ester (Intermediate 7, 1.5 g, 7.95 mmol) was taken in dry DCM (20 mL) along with DIPEA (3.9 mL, 22.3 mmol) and mesyl chloride (0.63 mL, 0.82 mmol) was added to it dropwise and stirred for 2 h at room temperature. The organic layer was washed with 10% aqueous solution of sodium bicarbonate, followed by water, and brine. The organic layer was dried over anhydrous sodium sulphate and concentrated under reduced pressure to provide the title compound (72%, 1.6 g, brown oil). $^1$H NMR (DMSO-$d_6$): δ 4.15-4.17 (m, 1H), 3.00-3.25 (m, 5H), 2.49-2.50 (m, 1H), 1.59-1.90 (m, 2H), 1.38 (s, 9H), 0.97 (s, 3H).

Intermediate 9: 1-Pyrrolidin-3-ylmethyl-1H-imidazole hydrochloride

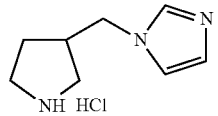 [SMILES: c1cn(CC2CCNC2)cn1 ; Cl]

Imidazole (0.58 g, 8.60 mmol) was taken in dry DMF (5 mL) and to this was added 60% sodium hydride (0.2 g, 8.58 mmol) at 0° C. and stirred at the same temperature for 1 h. 3-Methanesulfonyloxymethyl-pyrrolidine-1-carboxylic acid tert-butyl ester (Intermediate 8, 0.8 g, 2.86 mmol) was added and the reaction was heated to 60° C. for 2 h. The reaction mixture was cooled to room temperature and concentrated under reduced pressure. Ice was added to the resulting solid, extracted with DCM, and the organic layer was concentrated under reduced pressure to provide the crude product which was purified by column chromatography (pet ether/ethyl acetate 55%). The colorless oil was treated with 4M HCl in dioxane and stirred for 1 h. The reaction mixture was concentrated under reduced pressure to obtain the title compound. LCMS: 152.0 (M+1), Rt. 1.32 min, 97.6% (max), 96.5% (220 nm).

Intermediate 10: 3-Isobutylsulfanyl-benzoic acid methyl ester

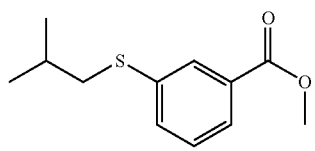

3-Mercapto-benzoic acid methyl ester (0.35 g, 2.08 mmol) was taken in dry DMF along with dry potassium carbonate (0.57 g, 4.16 mmol) and isobutyl iodide (0.38 g, 2.08 mmol), and the mixture was heated at 130° C. under microwave for 3 h. The reaction mixture was filtered and concentrated under reduced pressure to provide the title compound (64%, 0.3 g, colorless liquid). $^1$H NMR (DMSO-$d_6$): δ 7.80-7.80 (m, 1H), 7.71-7.74 (m, 1H), 7.58-7.60 (m, 1H), 7.43-7.47 (m, 1H), 3.84 (s, 3H), 2.90 (d, J=6.76 Hz, 2H), 1.77-1.80 (m, 1H), 0.98 (d, J=6.64 Hz, 6H).

Intermediate 11: (3-Isobutylsulfanyl-phenyl)-methanol

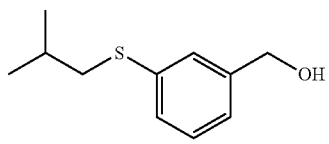

3-Isobutylsulfanyl-benzoic acid methyl ester (Intermediate, 10, 1 g, 4.46 mmol) was dissolved in dry THF (15 mL) and to this was added 2M solution of lithium borohydride (3.3 mL, 6.69 mmol) in THF. The reaction mixture was stirred for 15 h at room temperature and then ice and ethyl acetate was added. The organic layer was dried with sodium sulfate, filtered, and concentrated under reduced pressure to provide the crude product. Purification by column chromatography (pet ether/ethyl acetate 10%) provided the desired product (80%, 0.7 g, colorless liquid). $^1$H NMR (DMSO-$d_6$): δ 7.07-7.26 (m, 4H), 5.20 (t, J=5.80 Hz, 1H), 4.45 (d, J=5.80 Hz, 2H), 2.83 (d, J=6.80 Hz, 2H), 1.74-1.81 (m, 1H), 0.97 (d, J=6.64 Hz, 6H).

Intermediate 12: 1-Chloromethyl-3-isobutylsulfanyl-benzene

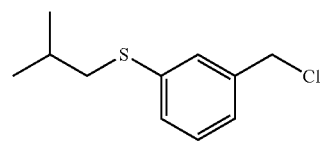

(3-Isobutylsulfanyl-phenyl)-methanol (Intermediate 11, 0.7 g, 3.57 mmol) was taken in dry DCM (10 mL) and excess of thionyl chloride (6 mL) was added to it drop wise at room temperature. The reaction mixture was heated to reflux for 5 h, cooled to room temperature and treated with ice and ethyl acetate. The organic layer was washed with 10% aqueous sodium bicarbonate, water, and brine. The organic layer was dried over sodium sulfate, filtered, and concentrated under reduced pressure to provide the desired product (30%, 0.23 g, colorless liquid). $^1$H NMR: (DMSO-$d_6$): δ 7.20-7.37 (m, 4H), 4.72 (s, 2H), 2.85-2.87 (m, 2H), 1.75-1.82 (m, 1H), 0.97 (d, J=6.64 Hz, 6H).

Intermediate 13:
3-(2-Methyl-propane-1-sulfonyl)-benzoic acid methyl ester

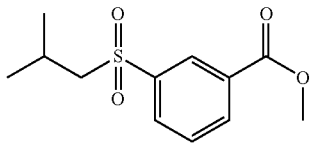 [SMILES: COC(=O)c1cccc(S(=O)(=O)CC(C)C)c1]

3-Isobutylsulfanyl-benzoic acid methyl ester (0.3 g, 1.33 mmol) was taken in dry DCM (10 mL) and cooled to 0° C. To this was added m-CPBA (0.46 g, 2.67 mmol) in portions and the reaction was stirred for 12 h at room temperature. The reaction mixture was washed with saturated sodium bicarbonate, water, brine, dried over sodium sulfate, filtered, and concentrated under reduced pressure to provide the crude product. Purification by column chromatography (pet ether/ethyl acetate 30%) provided the desired product (90%, 0.3 g, colorless liquid). $^1$H NMR: (DMSO-$d_6$): δ 8.37-8.38 (m, 1H), 8.26-8.29 (m, 1H), 8.17-8.20 (m, 1H), 7.80-7.84 (m, 1H), 3.90 (s, 3H), 3.29 (d, J=6.48 Hz, 2H), 1.98-2.05 (m, 1H), 0.96 (d, J=6.72 Hz, 6H).

Intermediate 14:
[3-(2-Methyl-propane-1-sulfonyl)-phenyl]-methanol

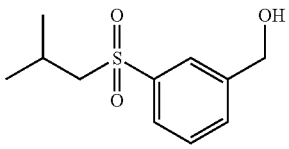

Intermediate 14 was synthesized as described for Intermediate 11 from Intermediate 13. $^1$H NMR (DMSO-$d_6$): δ 7.85 (s, 1H), 7.58-7.77 (m, 3H), 5.45 (t, J=5.72 Hz, 1H), 4.60 (d, J=7.76 Hz, 2H), 3.18 (d, J=6.44 Hz, 2H), 1.98-2.01 (m, 1H), 0.96 (d, J=6.72 Hz, 6H).

Intermediate 15: 1-Chloromethyl-3-(2-methyl-propane-1-sulfonyl)-benzene

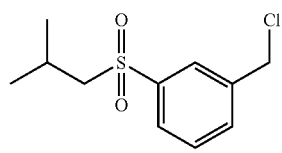

Intermediate 15 was synthesized according to the procedure described for Intermediate 12 using Intermediate 14 as the starting material. $^1$H NMR (DMSO-$d_6$): δ 7.98 (s, 1H), 7.86-7.88 (m, 1H), 7.65-7.81 (m, 2H), 4.89 (s, 2H), 3.22 (d, J=6.44 Hz, 2H), 1.99-2.02 (m, 1H), 0.96 (d, J=6.72 Hz, 6H).

Intermediate 16:
1-Pyrrolidin-3-ylmethyl-1H-[1,2,3]triazole hydrochloride

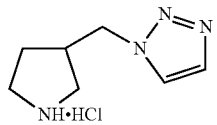

Intermediate 16 was synthesized as described for Intermediate 9 using Intermediate 8 and triazole as starting materials. LCMS: 153.2 (M+1), Rt. 0.45 min, 86.6% (max), 65% (220 nm).

Intermediate 20:
2-(Pyrrolidin-3-ylmethoxymethyl)-pyridine hydrochloride

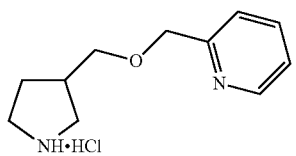

Intermediate 20 was synthesized according to the procedure described for Intermediate 9 from Intermediate 8 and 3-Hydroxymethyl-pyrrolidine-1-carboxylic acid tert-butyl ester. LCMS 193.3 (M+1), Rt. 2.19 min, 93.5% (max).

Intermediate 21: Pyridine-2-carboxylic acid (pyrrolidin-3-ylmethyl)-amide hydrochloride

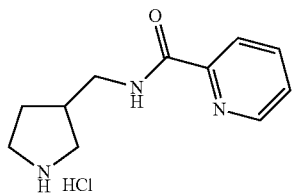 [SMILES: O=C(NCC1CCNC1)c1ccccn1 ; Cl]

T3P (50 wt. % solution in ethyl acetate; 5.15 mL; 16.2 mmol) was added to a solution of 3-Aminomethyl-pyrrolidine-1-carboxylic acid tert-butyl ester (1.8 g, 8.94 mmol), pyridine-2-carboxylic acid (1 g; 8.13 mmol) and Et$_3$N (3.4 mL, 24.3 mmol). The reaction mixture was stirred 2 h at room temperature followed by the addition of water. The organic layer was dried over sodium sulfate, filtered, and concentrated under reduced pressure to give crude product. Purification by column chromatography (pet ether/ethyl acetate 15%) provided the protected product. The product was treated with 4M HCl in dioxane and stirred at room temperature for 3 h. The reaction mixture was concentrated under reduced pressure to provide the desired product as a white solid. LCMS: 206.2 (M+1), Rt. 1.05 min, 94.1% (max), 97.6% (254 nm).

Intermediate 22: 3-Isobutoxy-benzaldehyde

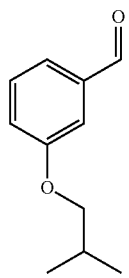

3-hydroxy benzaldehyde (25 g, 0.20 mol) was taken in dry DMF (200 mL) along with dry potassium carbonate (84.8 g, 0.60 mol) and to this was added isobutyl iodide (55.3 g, 0.30 mol) and heated at 100° C. for 12 h. The reaction mixture was filtered through Celite, and the resulting filtrate was concentrated under reduced pressure to give a crude oil. Purification by column chromatography resulted in the desired product (53%, 19 g, colorless oil). $^1$H NMR: (DMSO-$d_6$): δ 9.96 (s, 1H), 7.47-7.52 (m, 2H), 7.40 (d, J=1.48 Hz, 1H), 7.25-7.28 (m, 1H), 3.80 (d, J=6.52 Hz, 2H), 1.99-2.05 (m, 1H), 0.98 (d, J=6.68 Hz, 6H).

Intermediate 23: 1-(3-Isobutoxy-benzyl)-pyrrolidin-3-ol

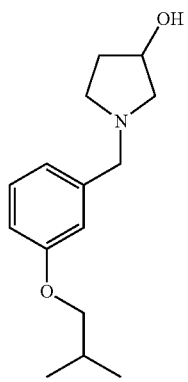

Intermediate 23 was synthesized using the procedure as described for Example 1 by using Intermediate 22 (5.1 g, 28.7 mmol) and 3-hydroxy pyrrolidine (2.5 g, 29.0 mmol) to give the titled compound as a colorless liquid (69%, 5 g, colorless liquid) LCMS: 250.2 (M+1), Rt. 3.03 min, 76.1% (max).

Intermediate 24: Methanesulfonic acid 1-(3-isobutoxy-benzyl)-pyrrolidin-3-yl ester

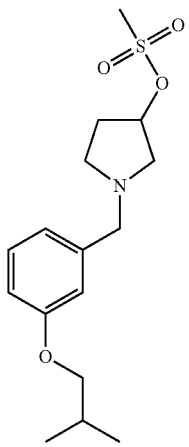

Intermediate 24 was synthesized using the procedure as described for Intermediate 8 by using Intermediate 23 (5.0 g, 20.0 mmol) and mesyl chloride (2.5 mL, 31.0 mmol) to give the titled compound as a colourless liquid (60%, 4.2 g). LCMS: 3.47 (M+1), Rt. 3.47 min, 82.2% (max).

Intermediate 25: 1-(3-Isobutoxy-benzyl)-pyrrolidine-3-carbonitrile

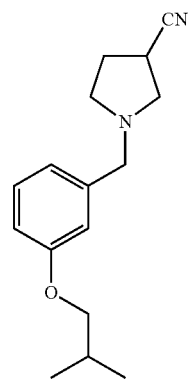 [SMILES: CC(C)COc1cccc(CN2CCC(O)C2)c1]

Methanesulfonic acid 1-(3-isobutoxy-benzyl)-pyrrolidin-3-yl ester (Intermediate 24, 4.2 g, 12.84 mmol) was dissolved in dry DMSO (10 mL), KCN (1.7 g, 25.68) was added, and the reaction mixture heated at 80° C. for 4 h. The resulting yellow mixture was cooled and brine (4 mL) and water (4.5 mL) were added. The mixture was extracted with diethyl ether (50 mL X 3), dried over magnesium sulfate, filtered and concentrated under reduced pressure. The resulting residue was purified by flash chromatography (diethylether/isohexane) (50/50) to give the titled compound as a colorless oil (82%, 2.7 g). LCMS: 259.0 (M+1), Rt. 3.41 min, 90.6% (max), 89.4 (220 nm).

Intermediate 26: N-Hydroxy-1-(3-isobutoxy-benzyl)-pyrrolidine-3-carboxamidine

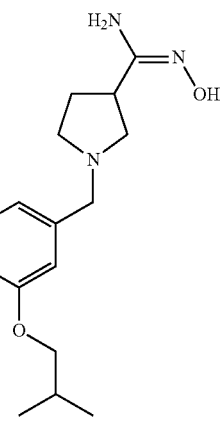

A solution of 1-(3-Isobutoxy-benzyl)-pyrrolidine-3-carbonitrile (Intermediate 25, 2.7 g, 10.42 mmol) and hydroxylamine (2.1 mL of a 50 percent w/v aq. solution, 31.27 mmol) in EtOH (25 mL) was heated to reflux. After 2 h, the reaction mixture was cooled to room temperature and concentrated in vacuum to afford the title compound as a colorless liquid (79%. 2.4 g). LCMS: 292.3 (M+1), Rt. 2.82 min, 92.8% (max), 91.1 (220 nm).

Intermediate 27:
3-Azido-1-(3-isobutoxy-benzyl)-pyrrolidine

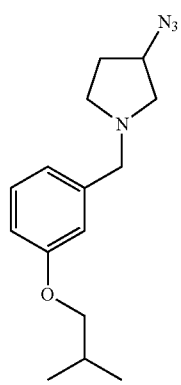 [SMILES: CC(C)COc1cccc(CN2CCC(N=[N+]=[N-])C2)c1]

Sodium azide (1.98 g, 30.58 mmol) was added to a solution of Methanesulfonic acid 1-(3-isobutoxy-benzyl)-pyrrolidin-3-yl ester (Intermediate 24, 5 g, 15.3 mmol) in dry dimethylformamide (25 mL) and the resultant suspension heated at 65° C. for 8 h. After cooling to room temperature, the reaction mixture was diluted with water and extracted into diethyl ether. The organic phase was washed two further times with water, then brine. The organic extracts were dried (MgSO₄), filtered and evaporated in vacuo to give an oil. This was purified by flash chromatography on silica, eluting with diethyl ether/cyclohexane (20:80 to 40:60), to give the title compound as an oil (73%, 3.1 g, colorless liquid) LCMS: 275.1 (M+1), Rt. 3.58 min, 91.7% (max).

Intermediate 28:
1-(3-Isobutoxy-benzyl)-pyrrolidine-3-carboxylic acid methyl ester

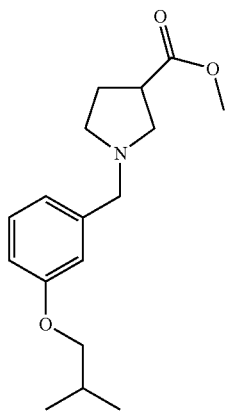 [SMILES: COC(=O)C1CCN(Cc2cccc(OCC(C)C)c2)C1]

Intermediate 28 was synthesized using the procedure as described for Intermediate 23 by using 3-Isobutoxy-benzaldehyde (Intermediate 22, 3 g, 16.9 mmol) and Pyrrolidine-3-carboxylic acid methyl ester (2 g, 15.3 mmol) to give the titled compound as a colorless liquid (42%, 1.8 g). LCMS: 292.2 (M+1), Rt. 3.58 min, 95.9% (max).

Intermediate 29:
1-(3-Isobutoxy-benzyl)-pyrrolidine-3-carboxylic acid hydrazide

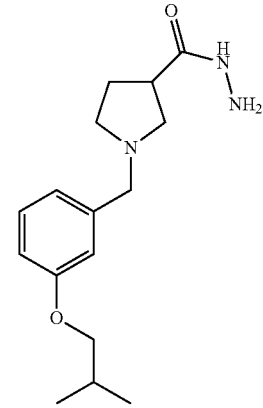 [SMILES: CC(C)COc1cccc(CN2CCC(C(=O)NN)C2)c1]

1-(3-Isobutoxy-benzyl)-pyrrolidine-3-carboxylic acid methyl ester (Intermediate 28, 0.8 g, 2.74 mmol) was taken in ethanol (20 mL) and hydrazine hydrate (5 mL) was added to it. The reaction mixture was heated to reflux for 3 h. The reaction mixture was cooled to room temperature and concentrated under reduced pressure to give a crude oil. Purification by column chromatography (pet ether/ethyl acetate 25%) provided the titled compound as a colorless oil (75%, 0.6 g). LCMS: 292.3 (M+1), Rt. 2.77 min, 88.0% (max), 87.8 (220 nm).

Intermediate 30: Acetic acid 2-{N-[1-(3-isobutoxy-benzyl)-pyrrolidine-3-carbonyl]-hydrazino}-2-oxo-ethyl ester

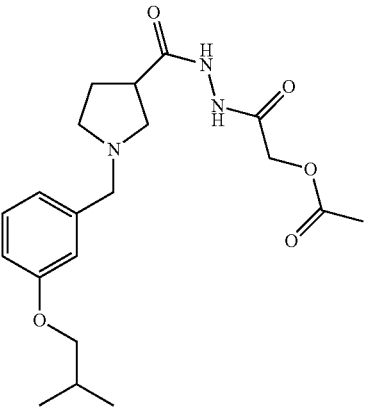 [SMILES: CC(=O)OCC(=O)NNC(=O)C1CCN(Cc2cccc(OCC(C)C)c2)C1]

1-(3-Isobutoxy-benzyl)-pyrrolidine-3-carboxylic acid hydrazide (Intermediate 29, 2 g, 6.87 mmol) was taken in dry DCM (25 mL) along with N-methyl morpholine (1.14 mL, 7.56) to which acetoxy acetyl chloride (1.4 mL, 10.3 mmol) was added at 0° C. and the reaction mixture was stirred for 2 h at room temperature. The reaction mixture was washed with water, then brine and the organic phase was dried over dry sodium sulphate and purified by column chromatography (pet ether/ethyl acetate 15%) to get the titled compound as a colorless oil (53$, 1.4 g). LCMS: 392.3 (M+1), Rt. 2.99 min, 71.7% (max).

Intermediate 31: Acetic acid 5-[1-(3-isobutoxy-benzyl)-pyrrolidin-3-yl]-[1,3,4]oxadiazol-2-ylmethyl ester

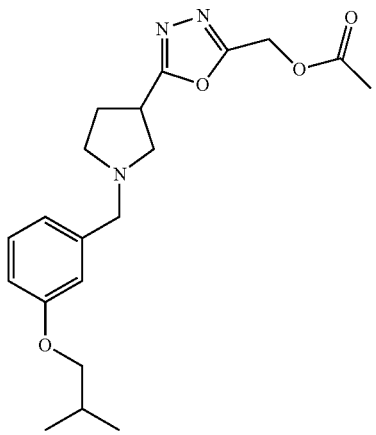 [SMILES: CC(=O)OCc1nnc(C2CCN(Cc3cccc(OCC(C)C)c3)C2)o1]

Acetic acid 2-{N'-[1-(3-isobutoxy-benzyl)-pyrrolidine-3-carbonyl]-hydrazino}-2-oxo-ethyl ester (Intermediate 30, 0.5 g, 1.27 mmol) was taken in dry DCM (10 mL) and triethylamine (0.53 mL, 3.8 mmol) was added to it. The reaction mixture was cooled to 0° C. and 2-chloro-1,3-dimethyl imidazolinium chloride (0.32 g, 1.91 mmol) was added to it and stirred for 12 h. The reaction mixture was washed with water, organic phase was dried over anhydrous sodium sulfate, and concentrated under reduced pressure to provide the crude product, which was purified by column chromatography (pet ether ethyl acetate 35%) to get the titled compound as a colorless oil (63%, 0.3 g). LCMS: 374.2 (M+1), Rt. 3.26 min, 46.6% (max).

Intermediate 32: methyl 1-(3-phenoxybenzyl)pyrrolidine-3-carboxylate

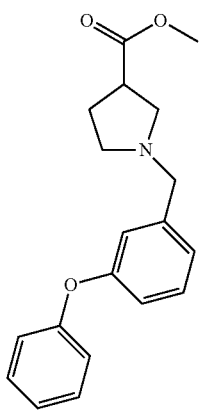 [SMILES: COC(=O)C1CCN(Cc2cccc(Oc3ccccc3)c2)C1]

To a solution of Ethyl pyrrolidine-3-carboxylate (1 equiv), 3-Phenoxy-benzaldehyde (1 equiv) and sodiumtriacetoxyborohydride was mixed in dichloroethane (50 ml) and the mixture was heated at 65° C. for 3 h. The reaction mixture was cooled to room temperature, concentrated under reduced pressure and extracted with ethyl acetate. The combined organic layer was washed with water (20 ml) and brine solution, then dried over anhydrous sodium sulfate and evaporated under reduced pressure. The crude residue was purified by column chromatography using petroleum ether-ethyl acetate as eluents to provide the pure ester (75%, pale brown gum). $^1$H NMR (400 MHz, CD$_3$OD): δ 7.48 (t, J=7.96 Hz, 1H), 7.42-7.38 (m, 2H), 7.29 (d, J=7.64 Hz, 1H), 7.21-7.15 (m, 2H), 7.11-7.08 (m, 1H), 7.06-7.06 (m, 2H), 4.40 (d, J=1.72 Hz, 2H), 3.75 (s, 3H), 3.60 (br s, 2H), 3.43 (br s, 3H), 2.44 (br s, 1H), 2.33-2.31 (m, 1H).

Intermediate 33: methyl 1-(3-(2,2,2-trifluoroethoxy)benzyl)pyrrolidine-3-carboxylate

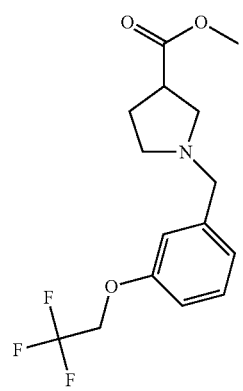 [SMILES: COC(=O)C1CCN(Cc2cccc(OCC(F)(F)F)c2)C1]

Intermediate 33 was synthesized as described for Intermediate 32 from Ethyl pyrrolidine-3-carboxylate and 3-trifluoromethoxybenzaldehyde. $^1$H NMR (400 MHz, CD$_3$OD): δ 7.33-7.29 (m, 1H), 7.05-7.03 (m, 2H), 6.96-6.94 (m, 1H), 4.60-4.51 (m, 2H), 3.76-3.66 (m, 5H), 3.14-3.10 (m, 1H), 2.94-2.89 (m, 1H), 2.85-2.81 (m, 1H), 2.75-2.67 (m, 2H), 2.16-2.10 (m, 2H).

Intermediate 34: 1-(3-phenoxybenzyl)pyrrolidine-3-carboxylic acid

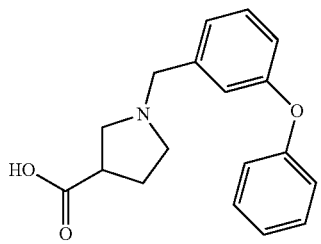 [SMILES: O=C(O)C1CCN(Cc2cccc(Oc3ccccc3)c2)C1]

To a solution of methyl 1-(3-phenoxybenzyl)pyrrolidine-3-carboxylate (Intermediate 32) in THF (16 mL) and water (4 mL), lithium hydroxide (0.43 g, 0.010 mol) was added and stirred for 12 h at RT. Upon completion of reaction, the reaction mixture was concentrated; water was added and acidified with 1.5 N HCl to get Pale Brown Gum (80%). $^1$H NMR (400 MHz, DMSO-d$_6$): δ 7.42-7.38 (m, 3H), 7.21-7.19 (m, 1H), 7.17-7.15 (m, 1H), 7.13-7.11 (m, 1H), 7.03-7.01 (m, 2H), 6.98-6.96 (m, 1H), 3.97 (s, 2H), 3.37-3.03 (m, 4H), 2.89 (s, 2H), 2.11-2.01 (m, 2H).

Intermediate 35: 1-(3-(2,2,2-trifluoroethoxy)benzyl)pyrrolidine-3-carboxylic acid

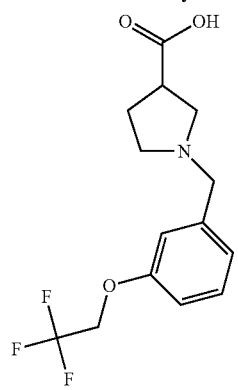

Intermediate 35 was synthesized as described for Intermediate 34 from Intermediate 33. ¹H NMR (400 MHz, DMSO-d$_6$): δ 7.26-7.22 (m, 1H), 6.96-6.94 (m, 2H), 6.92-6.89 (m, 1H), 4.75-4.69 (m, 2H), 3.58 (s, 2H), 2.72-2.62 (m, 2H), 2.55-2.46 (m, 1H), 2.39-2.37 (m, 1H), 1.95-1.91 (m, 1H), 1.87-1.84 (m, 1H), 1.77 (s, 2H).

Intermediate 36: 3-Methyl-pyrrolidine-3-carboxylic acid methyl ester

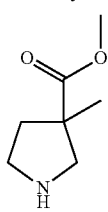

To a solution of 3-methyl-3-pyrrolidine carboxylic acid (1 g, 7.75 mmol) in methanol (15 mL) was added trimethylsilylchloride (4 mL) and the reaction mixture stirred at room temperature under nitrogen for 12 h. The reaction mixture was concentrated under reduced pressure and the resulting residue was purified from column chromatography pet ether/Ethyl acetate 35%) to afford the titled compound as off white solid (88%, 1 g). ¹H NMR: 400 MHz, DMSO-d$_6$: δ 9.56 (s, 1H), 3.66 (s, 3H), 3.45 (d, J=41.52 Hz, 1H), 3.23-3.30 (m, 1H), 3.12-3.19 (m, 1H), 3.00 (d, J=11.88 Hz, 1H), 2.23-2.30 (m, 1H), 1.80-1.87 (m, 1H), 1.32 (s, 3H). LCMS: 144.0 (M+H), Rt. 1.3 min, 96.7% (max).

Intermediate 37: 3-Methyl-1-(3-phenoxy-benzyl)-pyrrolidine-3-carboxylic acid methyl ester

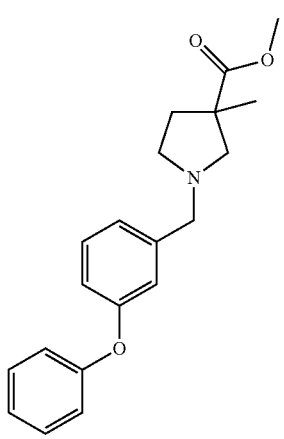 [SMILES: COC(=O)C1(C)CCN(Cc2cccc(Oc3ccccc3)c2)C1]

To a solution of 3-Methyl-pyrrolidine-3-carboxylic acid methyl ester (Intermediate 36, 0.7 g, 4.89 mmol) in dry methanol (10 mL) was added 3-phenoxy benzaldehyde (0.96 g, 4.89 mmol) and catalytic amount of acetic acid (0.5 mL). Then the reaction mixture was stirred for 30 min, cooled to 0° C., sodium cyanoborohydride (0.62 g, 9.79 mmol) was added and stirred at room temperature under nitrogen for 12 h. The methanol was completely evaporated under reduced pressure and purified by column chromatography (pet ether/Ethyl acetate 15%) to offer the titled compound as colorless liquid (51%, 0.8 g). LCMS: 326.3 (M+H), Rt. 3.6 min, 92.3% (max).

Intermediate 38: 3-Methyl-1-(3-phenoxy-benzyl)-pyrrolidine-3-carboxylic acid

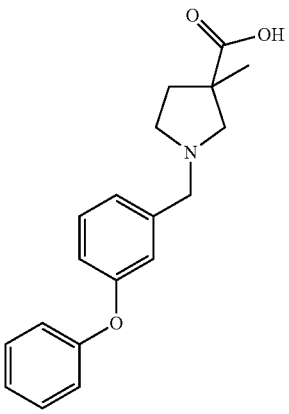 [SMILES: CC1(C(=O)O)CCN(Cc2cccc(Oc3ccccc3)c2)C1]

To a solution of 3-Methyl-1-(3-phenoxy-benzyl)-pyrrolidine-3-carboxylic acid methyl ester (Intermediate 37, 0.8 g, 2.46 mmol) in methanol (4 mL)/THF (4 mL) and water (2 mL) was added lithium hydroxide (0.32 g, 7.38 mmol) at 0° C. The reaction mixture was stirred for 3 h at room temperature and the methanol/THF was completely evaporated under reduced pressure. The resulting solution was acidified from dilute hydrochloric acid, to offer the titled compound as an off-white solid which was collected by filtration (65%, 0.5 g). LCMS: 312.3. (M+H), Rt. 3.3 min, 86.1% (max).

Intermediate 39: 3-Methyl-1-(3-phenoxy-benzoyl)-pyrrolidine-3-carboxylic acid methyl ester

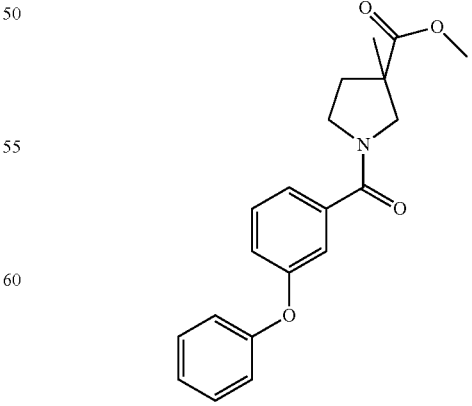

To a solution of 3-phenoxybenzoic acid (0.15 g, 0.70 mmol) and 3-Methyl-pyrrolidine-3-carboxylic acid methyl ester (0.1 g, 0.70 mmol) in dry dichloromethane (10 mL) was added triethylamine (0.29 mL, 2.1 mmol). The reaction cooled to 0° C. and T₃P (0.66 mL, 2.1 mmol) was added dropwise. The reaction was stirred for 5 h. After the completion of reaction (as evidenced by TLC), the organic layer was washed with water and purified by column chromatography to offer the titled compound as colorless liquid (87%, 0.2 g). LCMS: 340.0 (M+H), Rt. 4.6 min, 99.5% (max), 99.5% (254 nm).

Intermediate 40: 3-Methyl-1-(3-phenoxy-benzoyl)-pyrrolidine-3-carboxylic acid

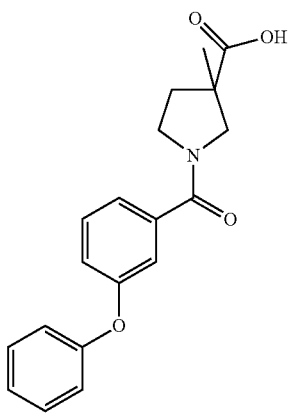 [SMILES: CC1(C(=O)O)CCN(C(=O)c2cccc(Oc3ccccc3)c2)C1]

To a solution of 3-Methyl-1-(3-phenoxy-benzoyl)-pyrrolidine-3-carboxylic acid methyl ester (Intermediate 39, 0.2 g, 0.58 mmol) in Methanol (4 mL)/THF (4 mL) and water (2 mL) was added lithium hydroxide (0.077 g, 1.76 mmol) at 0° C. Then the reaction was stirred for 3 h. After the completion of reaction (as evidenced by TLC), the methanol/THF was completely evaporated and acidified from dilute hydrochloric acid, to offer the titled compound as an off-white solid (73%, 0.14 g). ¹H NMR: 400 MHz, DMSO-d₆: δ 12.56 (s, 1H), 7.41-7.47 (m, 3H), 7.26-7.39 (m, 1H), 7.18-7.24 (m, 1H), 7.04-7.15 (m, 4H), 3.18-3.84 (m, 1H), 3.48-3.52 (m, 2H), 3.21 (d, J=10.56 Hz, 1H), 1.90 (s, 1H), 1.79 (t, J=20.76 Hz, 1H), 1.19 (s, 3H). LCMS: 326.3 (M+H), Rt. 3.9 min, 98.9% (max), 99.4% (254 nm).

Intermediate 41: 3-Methyl-1-(3-trifluoromethoxy-benzyl)-pyrrolidine-3-carboxylic acid methylester

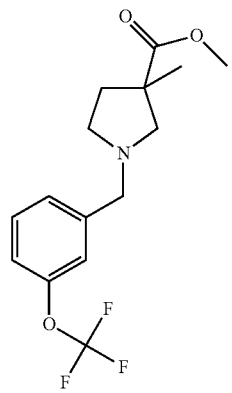 [SMILES: COC(=O)C1(C)CCN(Cc2cccc(OC(F)(F)F)c2)C1]

To a solution of 3-triflurophenoxy benzaldehyde (015 g, 0.78 mmol) in dry methanol (10 mL) was added 3-Methyl-pyrrolidine-3-carboxylic acid methyl ester (0.11 g, 0.78 mmol) and catalytic amount of acetic acid (0.5 mL). The reaction mixture was stirred for 30 min, cooled to 0° C., sodium cyanoborohydride (0.097 g, 1.7 mmol) was added and stirred at RT under nitrogen over night. After the completion of reaction (as evidenced by TLC), the methanol was completely evaporated and purified by column chromatography to offer the titled compound as colorless liquid (48%, 0.12 g). LCMS: 318.2 (M+H), Rt. 3.4 min, 33.3% (max).

Intermediate 42: 3-Methyl-1-(3-trifluoromethoxy-benzyl)-pyrrolidine-3-carboxylic acid

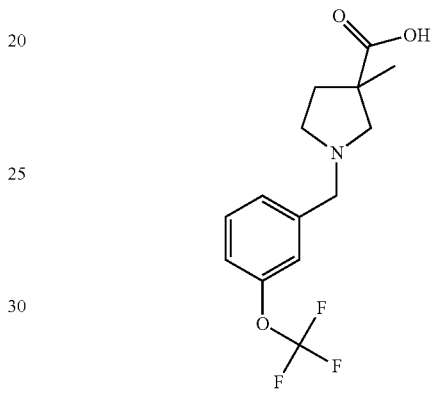

To a solution of 3-Methyl-1-(3-trifluoromethoxy-benzyl)-pyrrolidine-3 carboxylicacidmethylester (Intermediate 41, 0.12 g, 0.37 mmol) in methanol (4 mL)/THF (4 mL) and water (2 mL) was added lithium hydroxide (0.048 g, 1.13 mmol) at 0° C. The reaction was stirred for 3 h. After the completion of reaction (as evidenced by TLC), the methanol/THF was completely evaporated and acidified from dilute hydrochloric acid, to offer the titled compound as a light brown solid (90%, 0.1 g). LCMS: 304.3 (M+H), Rt. 2.9 min, 97.3% (max), ¹H NMR: 400 MHz, DMSO-d6: δ 7.61 (m, J=6.80, 3H), 7.42 (s, 1H), 4.26 (s, 2H), 3.33 (s, 2H), 3.11 (s, 2H), 1.90 (s, 2H), 1.34 (s, 3H).

Intermediate 43:
3-Cyano-3-hydroxy-pyrrolidine-1-carboxylic acid tert-butyl ester

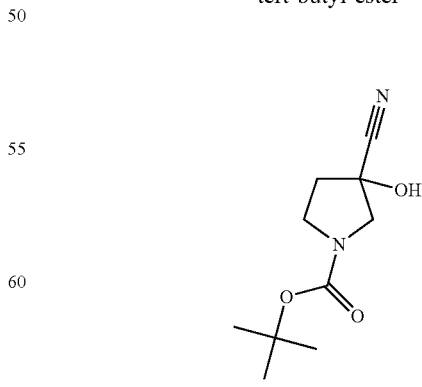

To a solution of 3-Oxo-pyrrolidine-1-carboxylic acid tert-butyl ester (6 g, 32.4 mmol) in H₂O/ether (85 mL/60 mL) was added sodium bisulphate (5.06 g, 48.6 mmol) at 0° C., stirred for 15 min and potassium cyanide (3.16 g, 48.6 mmol) was added and stirred at room temperature overnight. The reaction mixture was diluted with EtOAc and washed with water 4 times. The organic layer was dried over anhydrous sodium sulphate and concentrated under vacuum. The residue was purified by flash column chromatography (DCM/MeOH::0-3%) to provide the titled compound (52%, 3.6 g). LCMS: 13.0 (M+H), Rt. 3.2 min, 99.2% (max).

Intermediate 44:
3-Hydroxy-pyrrolidine-3-carboxylic acid methyl ester

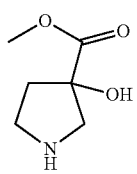

3-Cyano-3-hydroxy-pyrrolidine-1-carboxylic acid tert-butyl ester (Intermediate 43, 1 g, 4.72 mmol) was dissolved in 10 mL MeOH and aqueous solution of HCl (1.5 N, 5 mL). The mixture was heated to reflux for 5 h. The mixture was concentrated under reduced pressure to remove water. The resulting semi-solids were concentrated from 3×20 mL methanol:toluene (1:1) to remove the residual water. The mixture was dissolved in 12 mL methanol and 0.4 mL acetyl chloride and stirred for 18 h. The solution was concentrated from 2×10 mL methanol and 10 mL methanol:ethylacetate (1:1) to provide 1.2 g of amber oil. The material was used without further purification. LCMS: 146.0 (M+H), Rt. 0.5 min, 79.7% (max).

Intermediate 45: 3-Hydroxy-1-(3-phenoxy-benzyl)-pyrrolidine-3-carboxylic acid methyl ester

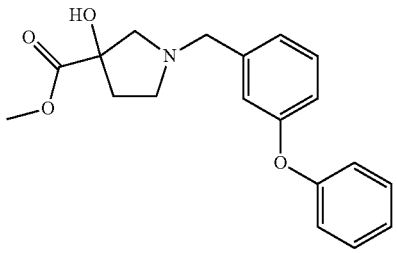 [SMILES: COC(=O)C1(O)CCN(Cc2cccc(Oc3ccccc3)c2)C1]

1-Chloromethyl-3-phenoxy-benzene (Intermediate 47, 1.4 g, 6.42 mmol) was dissolved in DMF (15 mL). To the reaction mixture added anhydrous potassium carbonate (6.12 g, 19.26 mmol) and 3-Hydroxy-pyrrolidine-3-carboxylic acid methyl ester (Intermediate 44, 1.1 g, 7.7 mmol). The reaction mixture was stirred at room temperature overnight, filtered through celite and, the filtrate was concentrated under reduced pressure. To the resulting residue was added water and extracted with ethyl acetate. The organic layer was washed with brine, dried over anhydrous sodium sulphate and concentrated under reduced pressure. Purification by flash column chromatography (DCM/MeOH:0-5%) provided the desired product (69% yield). LCMS: 328.3 (M+H), Rt. 3.2 min, 70.2% (max).

Intermediate 46: (3-Phenoxy-phenyl)-methanol

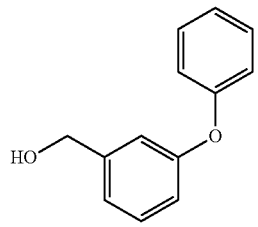

3-phenoxy-benzaldehyde (5 g, 25.22 mmol) was dissolved in dry methanol (60 mL), cooled to 0° C., and sodium borohydride (1.14 g, 30.26 mmol) was added portionwise. The reaction mixture was stirred at room temperature for 1.5 h and then concentrated under reduced pressure. The resulting residue was treated with saturated ammonium chloride solution, extracted with ethyl acetate, dried over anhydrous sodium sulphate, and concentrated under reduced pressure to provide the desired product (99%, 5 g). LCMS: 183.0 (M+H), Rt. 5.4 min, 93.1% (max).

Intermediate 47:
1-Chloromethyl-3-phenoxy-benzene

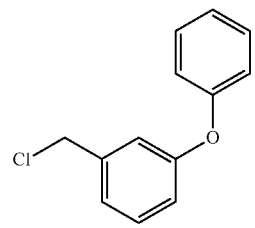 [SMILES: ClCc1cccc(Oc2ccccc2)c1]

(3-Phenoxy-phenyl)-methanol (Intermediate 46, 5 g, 25 mmol) was dissolved in DCM (50 mL), cooled to 0° C., and thionyl chloride (4 ml, 50 mmol) was added dropwise followed by a drop of DMF. The reaction mixture was stirred at room temperature for 12 h and concentrated under reduced pressure to remove solvent. To the resulting residue was added ice and extracted with ethyl acetate. The organic layer was dried over anhydrous sodium sulphate, concentrated under reduced pressure and purified by column chromatography (95%, 5.2 g). NMR: 400 MHz, DMSO-$d_6$: δ 7.36-7.43 (m, 3H), 7.13-7.20 (m, 2H), 6.95-7.07 (m, 4H), 4.73 (s, 2H).

Intermediate 48:
1-(3-Phenoxy-benzyl)-piperidin-2-one

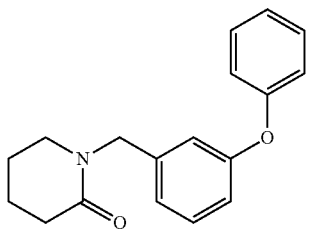 [SMILES: O=C1CCCCN1Cc1cccc(Oc2ccccc2)c1]

Sodium hydride (0.97 g, 24.2 mmol) was taken in 100 mL single necked round bottom flask under nitrogen, cooled to 0° C., and DMF (15 mL) was added. Δ-Velerolactum (1.6 g, 16.1 mmol) and 1-Chloromethyl-3-phenoxy-benzene (Intermediate 47, 4.58 g, 21 mmol) were added dropwise. The reaction mixture was stirred at room temperature for 2 h, ice was added, and then concentrated under reduced pressure. The resulting residue was treated with water and extracted with ethyl acetate. The organic layer was dried over anhydrous sodium sulphate, concentrated under reduced pressure and purified by flash column chromatography (DCM/MeOH: 0-5%) to provide the desired product (62%, 2.85 g). LCMS: 282.3 (M+H), Rt. 4.5 min, 92.3% (max).

Intermediate 49:
2-Oxo-1-(3-phenoxy-benzyl)-piperidine-3-carboxylic acid ethyl ester

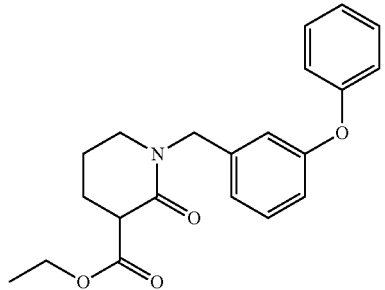 [SMILES: CCOC(=O)C1CCCN(Cc2cccc(Oc3ccccc3)c2)C1=O]

1-(3-Phenoxy-benzyl)-piperidin-2-one (Intermediate 48, 2.83 g, 10.07 mmol) was taken in THF (30 mL), cooled to −78° C., and 1M THF solution of lithium bis(trimethyl silyl)amide solution (20 mL, 20.14 mmol) was added drop wise. The reaction mixture was stirred for 1 h followed by dropwise addition of ethylchloroformate (0.96 ml, 10.07 mmol) at −78° C. The reaction mixture was stirred at room temperature for 1 h followed by addition of ice and ethyl acetate. The organic layer was washed with brine, dried over sodium sulfate, filtered, and concentrated under reduced pressure. Purification by flash column chromatography (0-3% DCM/MeOH) provided the desired product (80%, 2.86 g). LCMS: 354.3 (M+H), Rt. 4.9 min, 89.2% (max).

Intermediate 50: 3-Methyl-2-oxo-1-(3-phenoxy-benzyl)-piperidine-3-carboxylic acid ethyl ester

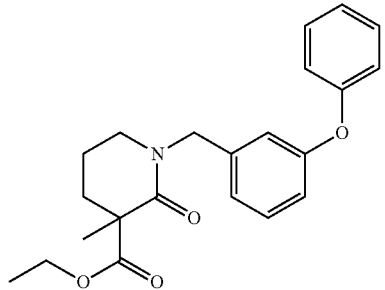 [SMILES: CCOC(=O)C1(C)CCCN(Cc2cccc(Oc3ccccc3)c2)C1=O]

2-Oxo-1-(3-phenoxy-benzyl)-piperidine-3-carboxylic acid ethyl ester (Intermediate 49, 1.4 g, 3.96 mmol) was taken in THF (15 mL), cooled to −78° C. and then lithium bis(trimethyl silyl)amide solution (1M in THF) (4.75 mL, 4.75 mmol) was added dropwise, followed by methyl iodide (0.8 ml, 11.89 mmol). The reaction mixture was stirred at room temperature for 12 h and then treated with ice followed by extraction with ethyl acetate. The organic layer was dried over anhydrous sodium sulfate, concentrated under reduced pressure and purified by flash column chromatography (0-3% DCM/MeOH) to give the product (97%, 1.4 g). LCMS: 368.3 (M+H), Rt. 5.2 min, 90.9% (max).

Intermediate 51: 3-Methyl-2-oxo-1-(3-phenoxy-benzyl)-piperidine-3-carboxylic acid

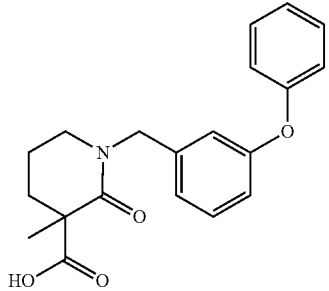 [SMILES: CC1(C(=O)O)CCCN(Cc2cccc(Oc3ccccc3)c2)C1=O]

3-Methyl-2-oxo-1-(3-phenoxy-benzyl)-piperidine-3-carboxylic acid ethyl ester (Intermediate 50, 1.4 g, 3.81 mmol) was taken in a mixture of tetrahydrofuran (14 mL), methanol (6 mL) and water (2 mL). To this was added lithium hydroxide monohydrate (0.489 g, 11.44 mmol) and stirred at room temperature for 3 h. The reaction mixture was concentrated under reduced pressure and water (20 mL) was added. The aqueous phase was acidified with aqueous solution of HCl (1.5N) until pH 6 and extracted with DCM. The organic layer was dried over anhydrous sodium sulfate and concentrated under reduced pressure to give a solid (93%, 1.2 g). LCMS: 296.2 (M+H), Rt. 4.5 min, 94.3% (max).

Intermediate 52: 1-(3-Phenoxy-cyclohexa-2,4-dienylmethyl)-pyrrolidin-2-one

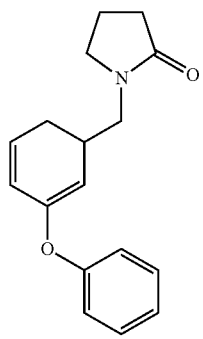 [SMILES: O=C1CCCN1CC1C=C(Oc2ccccc2)C=CC1]

To a solution of sodium hydride (0.4 g, 17.5 mmol) in 2 mL of anhydrous DMF was added 2-pyrrolidinone (1 g, 11.7 mmol) in DMF (1 mL) dropwise at 0° C. and stirred for 10 min at the same temperature. Then 1-bromomethyl-3-phenoxy benzene (2.8 g, 16.6 mmol) was added slowly and stirred for 12 h. The reaction mixture was quenched with ice and the solid obtained was collected by filtration to provide the titled compound as a colorless oil (51%, 1.6 g). LCMS: 268.0 (M+H), Rt. 4.3 min, 94.1% (max), 94.9 (254 nm).

Intermediate 53: 2-Oxo-1-(3-phenoxy-benzyl)-pyrrolidine-3-carboxylic acid ethyl ester

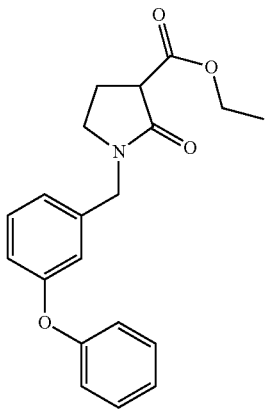 [SMILES: CCOC(=O)C1CCN(Cc2cccc(Oc3ccccc3)c2)C1=O]

1-(3-Phenoxy-cyclohexa-2,4-dienylmethyl)-pyrrolidin-2-one (Intermediate 52, 4 g, 14.9 mmol) was taken in anhydrous tetrahydrofuran (30 ml) and cooled to −78° C. Lithium bis(trimethylsilyl)amide (16 ml, 16.39 mmol) (1M in THF) was added dropwise to the above solution and stirred for 1 h at the same temperature. Ethylchloroacetate (1.6 g, 14.9 mmol) was added dropwise and stirred for 2 h. The reaction mixture was quenched with ice and extracted with ethyl acetate. The organic layer was washed with water then brine, dried over anhydrous sodium sulfate, and concentrated under reduced pressure to provide the crude product, which was purified by column chromatography (pet ether/ethyl acetate 20%) to get the titled compound as a colorless oil (62%, 3.1 g). LCMS: 340.0 (M+H), Rt. 4.8 min, 90.7% (max).

Intermediate 54 and 55: 3-Hydroxy-2-oxo-1-(3-phenoxy-benzyl)-pyrrolidine-3-carboxylic acid ethyl ester and 3-Chloro-2-oxo-1-(3-phenoxy-benzyl)-pyrrolidine-3-carboxylic acid ethyl ester

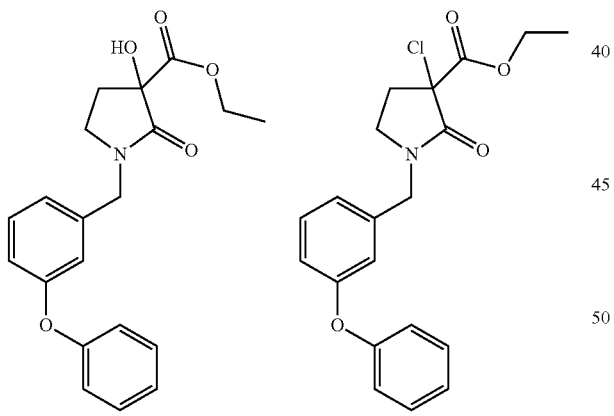

2-Oxo-1-(3-phenoxy-benzyl)-pyrrolidine-3-carboxylic acid ethyl ester (Intermediate 53, 1.5 g, 4.4 mmol) was taken in 2-propanol (10 mL) and cerium chloride heptahydrate (0.6 g, 1.7 mmol) at room temperature. Oxygen gas was bubbled through the solution for 1 h and then the reaction mixture was stirred under oxygen atmosphere for 12 h. The reaction mixture was concentrated under reduced pressure and purified by column chromatography (pet ether/ethyl acetate 30%) to obtain the two titled compounds (Intermediate 54, 78%, 610 mg and Intermediate 55, 51%, 520 mg). LCMS: (Intermediate 55) 374.0 (M+H), Rt. 5.17 min, 94.5% (max). LCMS: (Intermediate 54) 356.3 (M+H), Rt. 4.32 min, 77.35% (max).

Intermediate 56: 3-Hydroxy-2-oxo-1-(3-phenoxy-benzyl)-pyrrolidine-3-carboxylic acid

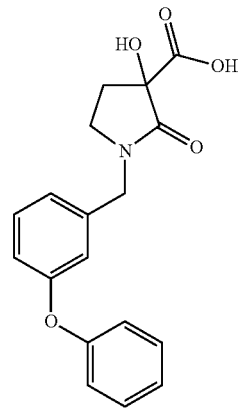 [SMILES: O=C(O)C1(O)CCN(Cc2cccc(Oc3ccccc3)c2)C1=O]

3-Hydroxy-2-oxo-1-(3-phenoxy-benzyl)-pyrrolidine-3-carboxylic acid ethyl ester (Intermediate 54, 0.3 g, 0.84 mmol) was taken in 10 ml of tetrahydrofuran and 10% aqueous solution of sodium hydroxide (5 ml) was added to it and stirred for 1 h at room temperature. The reaction mixture was concentrated under reduced pressure and the resulting residue was acidified with aqueous solution of HCl (1.5N) to pH 3. The solid that formed was collected by filtration to give the desired product as a gummy solid (55%, 150 mg). LCMS: 328.2 (M+H), Rt. 3.8 min, 82.8% (max).

Intermediate 57: 3-Chloro-2-oxo-1-(3-phenoxy-benzyl)-pyrrolidine-3-carboxylic acid

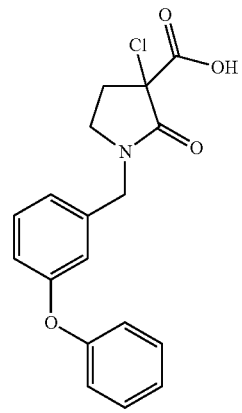 [SMILES: O=C(O)C1(Cl)CCN(Cc2cccc(Oc3ccccc3)c2)C1=O]

3-Chloro-2-oxo-1-(3-phenoxy-benzyl)-pyrrolidine-3-carboxylic acid ethyl ester (Intermediate 55, 0.5 g, 1.34 mmol) was taken in 10 mL of tetrahydrofuran and 10% aqueous solution of sodium hydroxide (5 mL) was added to it and stirred for 1 h at room temperature. The reaction mixture was concentrated under reduced pressure and acidified with aqueous solution of HCl (1.5N) to pH 3. The solid that formed was collected by filtration to provide the titled compound as a gummy solid (28%, 130 mg). NMR: 400 MHz, DMSO-$d_6$: δ 13.91 (s, 1H), 6.87-7.40 (m, 9H), 4.38-4.51 (m, 2H), 3.30-3.38 (m, 2H), 2.48-2.50 (m, 1H), 2.31-2.41 (m, 1H).

Intermediate 58: 3-(2-Methyl-propane-1-sulfinyl)-benzoic acid methyl ester

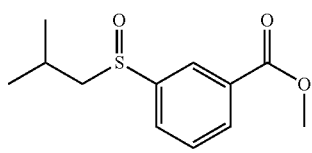 [SMILES: COC(=O)c1cccc(S(=O)CC(C)C)c1]

3-Isobutylsulfanyl-benzoic acid methyl ester (0.8 g, 3.57 mmol) was taken in dry DCM (10 mL) and to this was added chromium (IV) oxide (0.53 g, 5.35 mmol) and stirred at room temperature for 12 h. The reaction mixture was concentrated under reduced pressure and the resulting residue was purified by column chromatography (pet ether/ethyl acetate 15%) (58%, 0.5 g, colorless liquid). $^1$H NMR: 400 MHz, DMSO-$d_6$: δ 7.92-8.23 (m, 3H), 7.70-7.74 (m, 1H), 3.89 (s, 3H), 2.68-2.80 (m, 2H), 2.06-2.09 (m, 1H), 0.97-1.10 (m, 6H).

Intermediate 59:
[3-(2-Methyl-propane-1-sulfinyl)-phenyl]-methanol

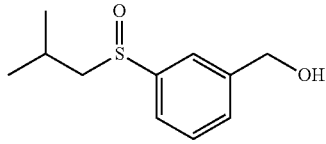

Intermediate 59 was synthesized using the procedure as described for Intermediate 11 from Intermediate 58 (48%, 0.2 g, colorless liquid). LCMS: 213.0 (M+1), Rt. 2.48 min, 88.9% (max), 87.5% (220 nm).

Intermediate 60:
3-(2-Methyl-propane-1-sulfinyl)-benzaldehyde

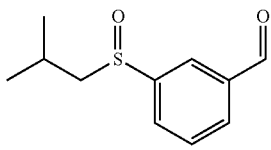

[3-(2-Methyl-propane-1-sulfinyl)-phenyl]-methanol (Intermediate 59, 0.2 g, 0.70 mmol) was taken in dry DCM (10 mL) and to this was added Dess-Martin periodinane (0.45 g, 1.06 mmol) and stirred at room temperature for 12 h. The reaction mixture was washed with 10% aqueous solution of sodium bicarbonate followed by water and brine, the organic layer was dried over dry sodium sulfate, concentrated under reduced pressure and purified by column chromatography (pet ether/ethyl acetate 15%) to provide the titled product as an oil (68%, 0.1 g). LCMS: 211.0 (M+1), Rt. 2.85 min, 80.4% (max), 95.1% (254 nm).

Intermediate 61: 3-Methyl-1-(2-phenyl-oxazol-4-ylmethyl)-pyrrolidine-3-carboxylic acid

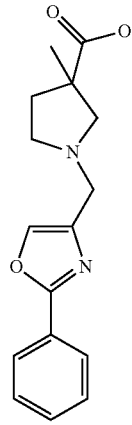

Intermediate 61 was synthesized according to the procedure for Intermediate 37 from Intermediate 36 and 2-Phenyl-oxazole-4-carbaldehyde (Enamine). $^1$H NMR (DMSO-$d_6$) δ: 7.56-7.25 (m, 3H), 7.21-6.73 (m, 5H), 3.83-3.49 (m, 2H), 3.15-2.93 (m, 1H), 2.81-2.29 (m, 5H), 2.19-1.94 (m, 1H).

Intermediate 62:
4-(3-Phenoxy-benzyl)-morpholine-2-carboxylic acid ethyl ester

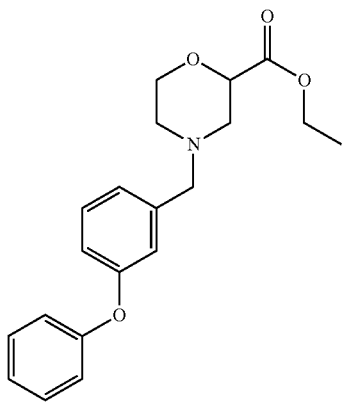 [SMILES: CCOC(=O)C1CN(Cc2cccc(Oc3ccccc3)c2)CCO1]

To a solution of Morpholine-2-carboxylic acid ethyl ester (300.00 mg; 1.88 mmol; 1.00 eq.) and 3-Phenoxy-benzaldehyde (0.37 g; 1.88 mmol; 1.00 eq.) in DCM (5.00 ml; 78.30 mmol; 41.55 eq.) was added sodium triacetoxyborohydride (0.48 g; 2.26 mmol; 1.20 eq.). The reaction mixture was heated to 40° C. for 2 h and then treated with saturated sodium bicarbonate. The organic layer was dried over sodium sulfate, filtered, and concentrated under reduced pressure to provide a colorless oil. $^1$H NMR (CDCl$_3$) δ: 7.40-7.26 (m, 3H), 7.16-7.00 (m, 5H), 6.96-6.88 (m, 1H), 4.30-4.19 (m, 3H), 4.04 (dt, J=11.1, 3.6 Hz, 1H), 3.76-3.65 (m, 1H), 3.53 (q, J=9.0 Hz, 2H), 3.04-2.88 (m, 1H), 2.66-2.55 (m, 1H), 2.43-2.26 (m, 2H), 1.30 (t, J=7.5 Hz, 3H).

Intermediate 63:
4-(3-Phenoxy-benzyl)-morpholine-2-carboxylic acid

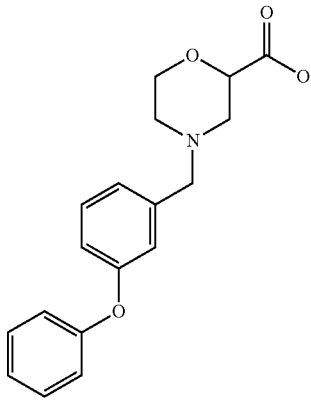 [SMILES: O=C(O)C1CN(Cc2cccc(Oc3ccccc3)c2)CCO1]

4-(3-Phenoxy-benzyl)-morpholine-2-carboxylic acid ethyl ester (Intermediate 63, 230.00 mg; 0.61 mmol; 1.00 eq.) was stirred at room temperature for 2 h in a solution of KOH (68.03 mg; 1.21 mmol; 2.00 eq.) in MeOH (10.00 ml; 246.57 mmol; 406.66 eq.). The reaction was quenched by diluting the mixture in DCM and adding 5 mL of HCl (5N). The organic layer was separated and the aqueous layer was extracted twice by DCM. The combined organic layers were dried over sodium sulfate, filtered, and concentrated under reduced pressure to provide the desired product. $^1$H NMR (CDCl$_3$) δ: 7.40-7.26 (m, 3H), 7.16-7.00 (m, 5H), 6.96-6.88 (m, 1H), 4.30-4.19 (m, 3H), 4.04 (dt, J=11.1, 3.6 Hz, 1H), 3.76-3.65 (m, 1H), 3.04-2.88 (m, 1H), 2.66-2.55 (m, 1H), 2.43-2.26 (m, 2H).

Intermediate 64: 3-Methyl-1-(2-phenyl-thiazol-5-ylmethyl)-pyrrolidine-3-carboxylic acid

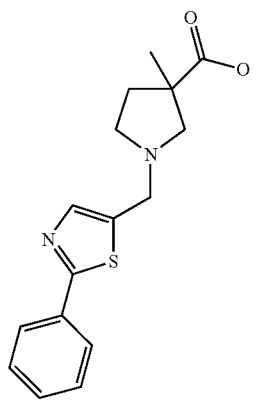 [SMILES: CC1(C(=O)O)CCN(Cc2cnc(-c3ccccc3)s2)C1]

Intermediate 64 was synthesized as described for Intermediate 61 from Intermediate 36 and 2-Phenyl-thiazole-5-carbaldehyde. $^1$H NMR (300 MHz, DMSO-d$_6$) δ: 12.25 (br s, 1H), 7.99-7.84 (m, 2H), 7.74 (s, 1H), 7.56-7.40 (m, 3H), 3.85 (s, 2H), 2.94 (d, J=9.1 Hz, 1H), 2.63 (dt, J=13.9, 7.3 Hz, 2H), 2.39 (d, J=9.1 Hz, 1H), 2.28 (ddd, J=13.3, 7.9, 5.8 Hz, 1H), 1.56 (ddd, J=13.5, 8.0, 6.3 Hz, 1H), 1.25 (s, 3H).

Intermediate 65: 3-(Pyrrolidine-1-sulfonyl)-benzoic acid methyl ester

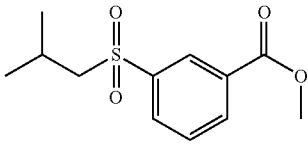 [SMILES: COC(=O)c1cccc(S(=O)(=O)CC(C)C)c1]

To a solution of 3-(1-pyrrolidinylsulfonyl)benzenecarboxylic acid (500 mg; 1.96 mmol; 1.00 eq.) in anhydrous dichloromethane (9 ml) and methanol (3 ml) was added dropwise a solution of (trimethylsilyl)diazomethane (1.47 ml; 2.94 mmol; 1.50 eq.; 2M in hexanes) and the yellow solution was stirred 4 h at room temperature. The reaction mixture was concentrated under reduced pressure and purified by column chromatography (hexanes/ethyl acetate 10-40%) to give the desired product as a white solid (510 mg, 94%). $^1$H NMR: (DMSO-d$_6$): δ 8.25 (ddt, J=5.2, 3.3, 1.6 Hz, 2H), 8.09 (ddd, J=7.8, 1.7, 1.3 Hz, 1H), 7.81 (t, J=8.0 Hz, 1H), 3.91 (s, 3H), 3.16 (ddd, J=6.8, 4.4, 2.7 Hz, 4H), 1.72-1.61 (m, 4H). LCMS: 270 (M+1), Rt. 4.60 min. HPLC: 97.3% (254 nm), Rt. 3.82 min.

Intermediate 66: [3-(Pyrrolidine-1-sulfonyl)-phenyl]-methanol

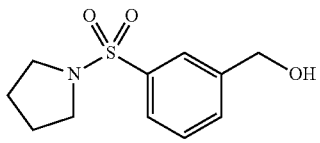 [SMILES: O=S(=O)(c1cccc(CO)c1)N1CCCC1]

A solution of 3-(pyrrolidine-1-sulfonyl)-benzoic acid methyl ester (intermediate 65; 500 mg; 1.86 mmol; 1.00 eq.) in anhydrous THF (25 ml) was cooled to ° C. A solution of lithium aluminum hydride (1.02 ml; 2.04 mmol; 1.10 eq.; 2M in THF) was added dropwise and the colorless solution was stirred at 0° C. for 2 h. The colorless solution was poured on 50 mL of ice and neutralized with solid ammonium chloride. The cloudy white emulsion was extracted with ethyl acetate, the combined organic phase washed with brine, dried over anhydrous sodium sulfate and concentrated under reduced pressure. The residue was purified by column chromatography (hexanes/ethyl acetate 20-80%) to give the desired product as a white solid (385 mg, 86%). $^1$H NMR (DMSO-d$_6$): δ 7.75 (s, 1H), 7.66 (dt, J=7.3, 1.7 Hz, 1H), 7.62 (d, J=7.6 Hz, 1H), 7.32 (t, J=7.5 Hz, 2H), 5.41 (t, J=5.8 Hz, 1H), 4.60 (d, J=5.8 Hz, 2H), 3.13 (ddd, J=6.8, 4.4, 2.7 Hz, 4H), 1.70-1.59 (m, 4H). LCMS: 242 (M+1), Rt. 2.86 min. HPLC: 100% (254 nm), Rt. 2.71 min.

Intermediate 67: 3-(Pyrrolidine-1-sulfonyl)-benzaldehyde

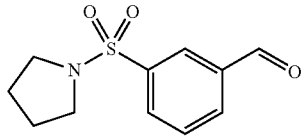 [SMILES: O=Cc1cccc(S(=O)(=O)N2CCCC2)c1]

A solution of [3-(Pyrrolidine-1-sulfonyl)-phenyl]-methanol (intermediate 66; 380 mg; 1.57 mmol; 1.00 eq.) and manganese (iv) oxide (2.74 g; 31.50 mmol; 20.00 eq.) in anhydrous DCM (15 ml) was stirred at room temperature for 4 h. The black suspension was filtered on celite and rinsed with DCM. The filtrate was concentrated under reduced pressure. The residue was purified by column chromatography (hexanes/ethyl acetate 10-60%) to give the desired product as a white solid (349 mg, 93%). $^1$H NMR (DMSO-d$_6$): δ 10.13 (s, 1H), 8.29 (t, J=1.6 Hz, 1H), 8.20 (dt, J=7.6, 1.3 Hz, 1H), 8.15-8.09 (m, 1H), 7.86 (t, J=7.7 Hz, 1H), 3.24-3.13 (m, 4H), 1.73-1.59 (m, 4H). LCMS: 240 (M+1), Rt. 3.38 min. HPLC: 100% (254 nm), Rt. 3.29 min.

Intermediate 68: 1-[3-(Pyrrolidine-1-sulfonyl)-benzyl]-pyrrolidine-3-carboxylic acid methyl ester

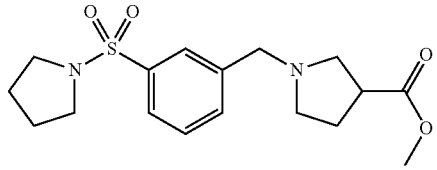 [SMILES: COC(=O)C1CCN(Cc2cccc(S(=O)(=O)N3CCCC3)c2)C1]

A solution of pyrrolidine-3-carboxylic acid methyl ester hydrochloride (215 mg; 1.30 mmol; 1.00 eq.), 3-(pyrrolidine-1-sulfonyl)-benzaldehyde (intermediate 67; 342 mg; 1.43 mmol; 1.10 eq.) and sodium triacetoxyborohydride (386 mg; 1.82 mmol; 1.40 eq.) in anhydrous 1,2-dichloroethane (5 ml) was heated at 65° C. for 3 h. The tan cloudy solution was diluted with ethyl acetate, washed with saturated aqueous sodium carbonate and the organic phase was concentrated under reduced pressure. The residue was purified by column chromatography (hexanes/ethyl acetate 20-100%) to give the desired product as a colorless oil (202 mg, 44%). $^1$H NMR (DMSO-d$_6$): δ 7.72 (s, 1H), 7.68 (d, J=7.3 Hz, 1H), 7.61 (d, J=7.5 Hz, 1H), 7.59-7.53 (m, 1H), 3.69 (dd, J=35.5, 13.5 Hz, 2H), 3.60 (s, 3H), 3.13 (t, J=6.7 Hz, 4H), 3.04 (ddd, J=14.3, 9.7, 6.5 Hz, 1H), 2.71-2.60 (m, 2H), 2.57-2.51 (m, 2H), 2.07-1.89 (m, 2H), 1.70-1.55 (m, 4H). LCMS: 353 (M+1), Rt. 2.31 min. HPLC: 99.3% (254 nm), Rt. 2.44 min.

Example 1

1-(3-p-Tolyloxy-benzyl)-pyrrolidine-3-carboxylic acid (pyridin-2-ylmethyl)-amide (1)

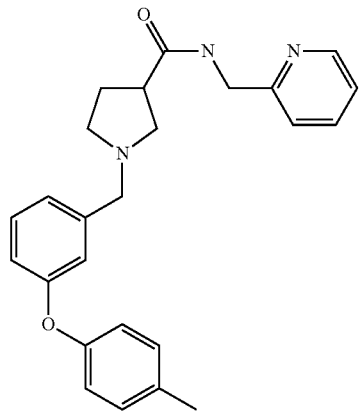

Pyrrolidine-3-carboxylic acid (pyridin-2-ylmethyl)-amide hydrochloride (Intermediate 2, 75.00 mg; 0.30 mmol; 1.00 eq.), MeOH (1.13 ml; 15.00 V) and triethylamine (0.04 ml; 0.33 mmol; 1.10 eq.) were dissolved in acetic acid (0.04 g; 0.61 mmol; 2.00 eq.), and THF (1.13 ml; 15.00 V) and 3-p-Tolyloxy-benzaldehyde (81.52 mg; 0.36 mmol; 1.20 eq.) were added. The reaction mixture was stirred for 2 h at room temperature. The reaction mixture was cooled to 0° C., sodiumcyanoborohydride (30.17 mg; 0.46 mmol; 1.50 eq.) was added and the reaction mixture was stirred for 12 h at room temperature. The solvent was removed under reduced pressure, the resulting residue was dissolved in dichloromethane, and washed with water (2×3 mL), then saturated brine solution. The combined organic layer was dried over anhydrous sodium sulphate and evaporated under reduced pressure to provide the crude product. Purification first by silica gel column chromatography to remove the starting materials and then by DSC-SCX column provided the final compound 1-(3-p-Tolyloxy-benzyl)-pyrrolidine-3-carboxylic acid (pyridin-2-ylmethyl)-amide (38.00 mg; 0.09 mmol; 29.6%; off white solid). $^1$H NMR (DMSO-$d_6$) δ 8.47 (d, J=4.28 Hz, 1H), 8.39 (t, J=5.84 Hz, 1H), 7.75-7.71 (m, 1H), 7.30-7.17 (m, 4H), 7.04 (d, J=7.72 Hz, 1H), 6.91-6.89 (m, 3H), 6.83-6.80 (m, 1H), 4.32 (d, J=5.96 Hz, 2H), 3.53 (s, 2H), 2.95-2.85 (m, 1H), 2.80-2.70 (m, 1H), 2.65-2.55 (m, 3H), 2.48-2.41 (m, 3H), 2.28 (s, 3H).

The following compounds were synthesized as described for Example 1 from the starting materials indicated in the Table.

| Cmpd | Structure | Data | Starting Materials |
|---|---|---|---|
| 2 | 1-[3-(3-Methoxy-phenoxy)-benzyl]-pyrrolidine-3-carboxylic acid (pyridin-2-ylmethyl)-amide | $^1$H NMR (DMSO-$d_6$) δ 8.47 (d, J = 4.72 Hz, 1H), 8.40 (t, J = 5.88 Hz, 1H), 7.74-7.70 (m, 1H), 7.62-7.58 (m, 1H), 7.47 (d, J = 8.00 Hz, 1H), 7.37 (t, J = 7.80 Hz, 1H), 7.27-7.15 (m, 5H), 7.05 (s, 1H), 6.97-6.95 (m, 1H), 4.32 (d, J = 5.88 Hz, 2H), 3.58 (s, 2H), 2.94-2.90 (m, 1H), 2.78 (t, J = 8.60 Hz, 1H), 2.65-2.55 (m, 2H), 2.49-2.45 (m, 1H), 1.95-1.91 (m, 2H). | Intermediate 2 and 3-(3-Methoxy-phenoxy)-benzaldehyde |
| 3 | 1-[3-(3,4-Difluoro-phenoxy)-benzyl]-pyrrolidine-3-carboxylic acid (pyridin-2-ylmethyl)-amide | $^1$H NMR (CD$_3$OD) δ: 8.48-8.46 (m, 1H), 7.82-7.77 (m, 1H), 7.36-7.20 (m, 4H), 7.16 (d, J = 7.64 Hz, 1H), 7.06-7.05 (m, 1H), 6.95-6.89 (m, 2H), 6.79-6.76 (m, 1H), 4.47 (s, 2H), 3.70-3.63 (m, 2H), 3.06-3.01 (m, 1H), 2.94-2.89 (m, 1H), 2.77-2.58 (m, 3H), 2.14-2.13 (m, 2H). | Intermediate 2 and 3-(3,4-Difluoro-phenoxy)-benzaldehyde |

| Cmpd | Structure | Data | Starting Materials |
|---|---|---|---|
| 4 | 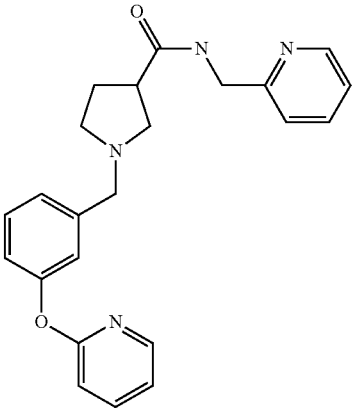 [SMILES: O=C(NCc1ccccn1)C1CCN(Cc2cccc(Oc3ccccn3)c2)C1]<br>1-[3-(Pyridin-2-yloxy)-benzyl]-pyrrolidine-3-carboxylic acid (pyridin-2-ylmethyl)-amide | $^1$H NMR (CD$_3$OD) δ: 8.49 (d, J = 4.32 Hz, 1H), 8.14-8.13 (m, 1H), 7.88-7.79 (m, 2H), 7.50 (t, J = 7.88 Hz, 1H), 7.38-7.28 (m, 4H), 7.19-7.13 (m, 2H), 7.01 (d, J = 8.32 Hz, 1H), 4.54-4.46 (m, 2H), 4.22-4.21 (m, 2H), 3.35-3.27 (m, 5H), 2.38-2.33 (m, 1H), 2.23-2.19 (m, 1H). | Intermediate 2 and 3-(Pyridin-2-yloxy)-benzaldehyde |
| 5 | 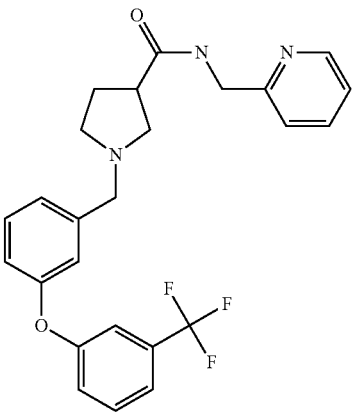 [SMILES: O=C(NCc1ccccn1)C1CCN(Cc2cccc(Oc3cccc(C(F)(F)F)c3)c2)C1]<br>1-[3-(3-Trifluoromethyl-phenoxy)-benzyl]-pyrrolidine-3-carboxylic acid (pyridin-2-ylmethyl)-amide | $^1$H NMR (DMSO-d$_6$) δ 8.47 (d, J = 4.72 Hz, 1H), 8.40 (t, J = 5.88 Hz, 1H), 7.74-7.70 (m, 1H), 7.62-7.58 (m, 1H), 7.47 (d, J = 8.00 Hz, 1H), 7.37 (t, J = 7.80 Hz, 1H), 7.27-7.15 (m, 5H), 7.05 (s, 1H), 6.97-6.95 (m, 1H), 4.32 (d, J = 5.88 Hz, 2H), 3.58 (s, 2H), 2.94-2.90 (m, 1H), 2.78 (t, J = 8.60 Hz, 1H), 2.65-2.55 (m, 2H), 2.49-2.45 (m, 1H), 1.95-1.91 (m, 2H). | Intermediate 2 and 3-(3-Trifluoromethyl-phenoxy)-benzaldehyde |
| 6 | 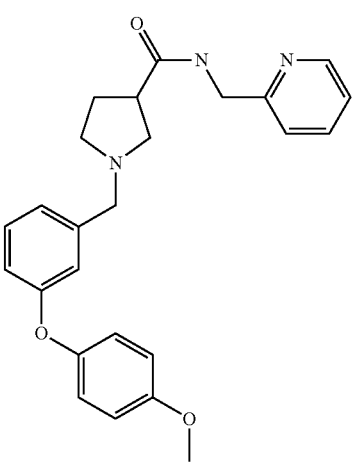 [SMILES: COc1ccc(Oc2cccc(CN3CCC(C(=O)NCc4ccccn4)C3)c2)cc1]<br>1-[3-(4-Methoxy-phenoxy)-benzyl]-pyrrolidine-3-carboxylic acid (pyridin-2-ylmethyl)-amide | $^1$H NMR (CD$_3$OD) δ: 8.48-8.47 (m, 1H), 7.82-7.78 (m, 1H), 7.34-7.24 (m, 3H), 7.03 (d, J = 7.56 Hz, 1H), 6.96-6.90 (m, 5H), 6.83-6.81 (m, 1H), 4.47 (s, 2H), 3.79 (s, 3H), 3.66-3.59 (m, 2H), 3.06-3.00 (m, 1H), 2.91 (t, J = 9.32 Hz, 1H), 2.77-2.56 (m, 3H), 2.13-2.11 (m, 2H). | Intermediate 2 and 3-(4-Methoxy-phenoxy)-benzaldehyde |

-continued

| Cmpd | Structure | Data | Starting Materials |
|---|---|---|---|
| 7 | 1-[3-(2-Methoxy-phenoxy)-benzyl]-pyrrolidine-3-carboxylic acid (pyridin-2-ylmethyl)-amide | $^1$H NMR (CD$_3$OD) δ: 8.48 (d, J = 4.68 Hz, 1H), 7.82-7.78 (m, 1H), 7.34-7.16 (m, 5H), 7.02-6.93 (m, 3H), 6.89-6.88 (m, 1H), 6.77-6.74 (m, 1H), 4.47 (s, 2H), 3.76 (s, 3H), 3.64 (s, 2H), 3.06-3.02 (m, 1H), 2.93 (t, J = 9.36 Hz, 1H), 2.77-2.73 (m, 1H), 2.69-2.60 (m, 2H), 2.14-2.11 (m, 2H). | Intermediate 2 and 3-(2-Methoxy-phenoxy)-benzaldehyde |
| 8 | 1-[3-(2,4-Difluoro-phenoxy)-benzyl]-pyrrolidine-3-carboxylic acid (pyridin-2-ylmethyl)-amide | $^1$H NMR (CD$_3$OD) δ: 8.49-8.47 (m, 1H), 7.82-7.78 (m, 1H), 7.34-7.27 (m, 3H), 7.18-7.07 (m, 3H), 7.00-6.96 (m, 2H), 6.85-6.82 (m, 1H), 4.47 (s, 2H), 3.68-3.61 (m, 2H), 3.06-3.00 (m, 1H), 2.91 (t, J = 9.36 Hz, 1H), 2.76-2.56 (m, 3H), 2.13-2.05 (m, 2H). | Intermediate 2 and 3-(2,4-Difluoro-phenoxy)-benzaldehyde |
| 9 | 1-[3-(3,5-Dimethyl-phenoxy)-benzyl]-pyrrolidine-3-carboxylic acid (pyridin-2-ylmethyl)-amide | $^1$H NMR (CD$_3$OD) δ: 8.47 (d, J = 4.64 Hz, 1H), 7.81-7.77 (m, 1H), 7.34-7.27 (m, 3H), 7.08 (d, J = 7.56 Hz, 1H), 7.00 (s, 1H), 6.88-6.86 (m, 1H), 6.76 (s, 1H), 6.58 (s, 2H), 4.47 (s, 2H), 3.66-3.65 (m, 2H), 3.04-3.02 (m, 1H), 2.92 (t, J = 9.24 Hz, 1H), 2.75-2.60 (m, 3H), 2.26 (s, 6H), 2.12-2.05 (m, 2H). | Intermediate 2 and 3-(3,5-Dimethyl-phenoxy)-benzaldehyde |

| Cmpd | Structure | Data | Starting Materials |
|---|---|---|---|
| 10 | 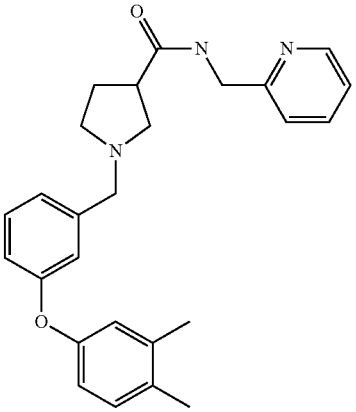 [SMILES: Cc1ccc(Oc2cccc(CN3CCC(C(=O)NCc4ccccn4)C3)c2)cc1C]<br>1-[3-(3,4-Dimethyl-phenoxy)-benzyl]-pyrrolidine-3-carboxylic acid (pyridin-2-ylmethyl)-amide | $^1$H NMR (CD$_3$OD) δ: 8.48-8.46 (m, 1H), 7.81-7.77 (m, 1H), 7.34-7.25 (m, 3H), 7.10-7.05 (m, 2H), 6.98-6.97 (m, 1H), 6.86-6.83 (m, 1H), 6.78-6.78 (m, 1H), 6.71-6.69 (m, 1H), 4.47 (s, 2H), 3.67-3.60 (m, 2H), 3.06-3.02 (m, 1H), 3.00-2.89 (m, 1H), 2.77-2.57 (m, 3H), 2.23 (s, 6H), 2.15-2.04 (m, 2H). | Intermediate 2 and 3-(3,4-Dimethyl-phenoxy)-benzaldehyde |
| 11 | 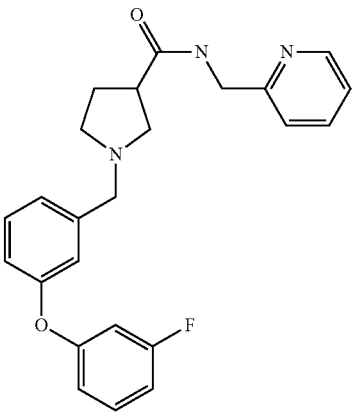 [SMILES: O=C(NCc1ccccn1)C1CCN(Cc2cccc(Oc3cccc(F)c3)c2)C1]<br>1-[3-(3-Fluoro-phenoxy)-benzyl]-pyrrolidine-3-carboxylic acid (pyridin-2-ylmethyl)-amide | $^1$H NMR (DMSO-d$_6$) δ: 8.47 (d, J = 4.64 Hz, 1H), 8.40-8.39 (m, 1H), 7.75-7.70 (m, 1H), 7.42-7.33 (m, 2H), 7.25-7.19 (m, 2H), 7.14 (d, J = 7.32 Hz, 1H), 7.02 (s, 1H), 6.98-6.93 (m, 2H), 6.86-6.83 (m, 2H), 4.32 (d, J = 5.88 Hz, 2H), 3.58 (s, 2H), 2.95-2.91 (m, 1H), 2.79 (t, J = 8.68 Hz, 1H), 2.59-2.43 (m, 3H), 1.95-1.90 (m, 2H). | Intermediate 2 and 3-(3-Fluoro-phenoxy)-benzaldehyde |
| 12 | 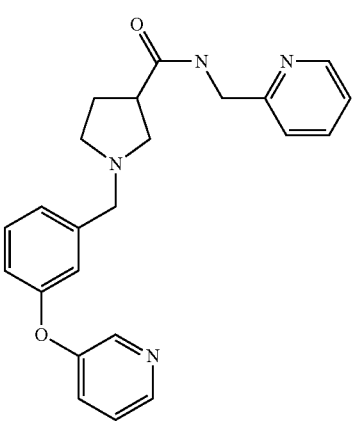 [SMILES: O=C(NCc1ccccn1)C1CCN(Cc2cccc(Oc3cccnc3)c2)C1]<br>1-[3-(Pyridin-3-yloxy)-benzyl]-pyrrolidine-3-carboxylic acid (pyridin-2-ylmethyl)-amide | $^1$H NMR (CD$_3$OD) δ: 8.80-8.79 (m, 1H), 8.63-8.58 (m, 2H), 8.22-8.20 (m, 1H), 8.05 (d, J = 8.00 Hz, 1H), 8.02-7.99 (m, 1H), 7.92 (d, J = 8.96 Hz, 1H), 7.63-7.59 (m, 1H), 7.52-7.49 (m, 2H), 7.34 (dd, J = 8.20, 1.24 Hz, 1H), 4.80-4.71 (m, 2H), 4.54-4.43 (m, 2H), 3.78-3.45 (m, 4H), 2.78 (s, 3H), 2.62-2.22 (m, 3H). | Intermediate 2 and 3-(Pyridin-3-yloxy)-benzaldehyde |

-continued

| Cmpd | Structure | Data | Starting Materials |
|---|---|---|---|
| 13 | 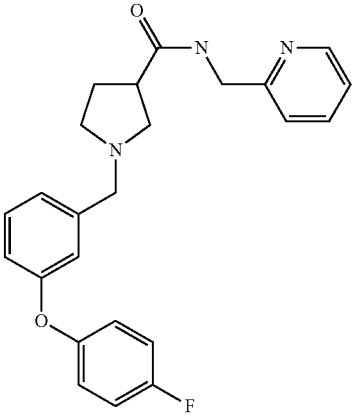 [SMILES: O=C(NCc1ccccn1)C1CCN(Cc2cccc(Oc3ccc(F)cc3)c2)C1]<br>1-[3-(4-Fluoro-phenoxy)-benzyl]-pyrrolidine-3-carboxylic acid (pyridin-2-ylmethyl)-amide | ¹H NMR (DMSO-d₆) δ: 11.02 (br s, 1H), 9.00-8.90 (m, 1H), 8.63 (b rs, 1H), 8.08 (s, 1H), 7.55-7.45 (m, 3H), 7.33-7.24 (m, 4H), 7.11-7.05 (m, 3H), 4.50-4.37 (m, 4H), 3.25-3.14 (m, 4H), 2.40-1.90 (m, 3H). | Intermediate 2 and 3-(4-Fluorophenoxy) benzylbromide |
| 14 | 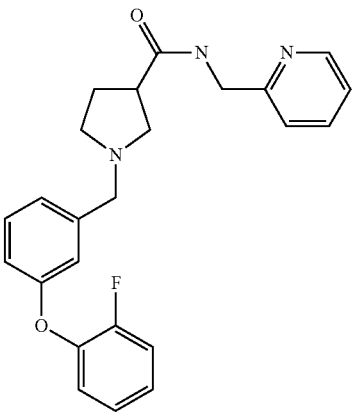 [SMILES: O=C(NCc1ccccn1)C1CCN(Cc2cccc(Oc3ccccc3F)c2)C1]<br>1-[3-(2-Fluoro-phenoxy)-benzyl]-pyrrolidine-3-carboxylic acid (pyridin-2-ylmethyl)-amide | ¹H NMR (DMSO-d₆) δ: 8.48-8.47 (m, 1H), 8.40-8.38 (m, 1H), 7.75-7.71 (m, 1H), 7.41-7.13 (m, 7H), 7.06 (d, J = 7.48 Hz, 1H), 6.93 (s, 1H), 6.83-6.80 (m, 1H), 4.32 (d, J = 5.92 Hz, 2H), 3.55 (s, 2H), 2.94-2.88 (m, 1H), 2.77 (t, J = 8.16 Hz, 1H), 2.65-2.55 (m, 1H), 2.35-2.25 (m, 2H), 1.93-1.90 (m, 2H). | Intermediate 2 and 3-(2-Fluoro-phenoxy)-benzaldehyde |
| 15 | 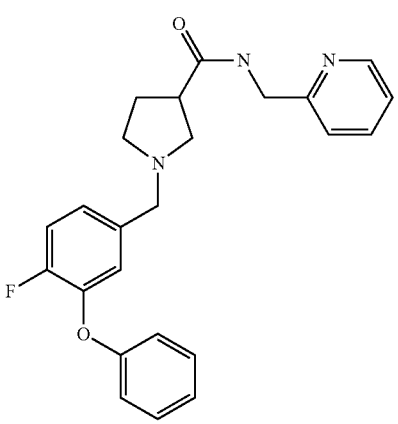 [SMILES: O=C(NCc1ccccn1)C1CCN(Cc2ccc(F)c(Oc3ccccc3)c2)C1]<br>1-(4-Fluoro-3-phenoxy-benzyl)-pyrrolidine-3-carboxylic acid (pyridin-2-ylmethyl)-amide | ¹H NMR (CD₃OD) δ: 8.80-8.79 (m, 1H), 8.63-8.58 (m, 2H), 8.22-8.20 (m, 1H), 8.05 (d, J = 8.00 Hz, 1H), 8.02-7.99 (m, 1H), 7.92 (d, J = 8.96 Hz, 1H), 7.63-7.59 (m, 1H), 7.52-7.49 (m, 2H), 7.34 (dd, J = 8.20, 1.24 Hz, 1H), 4.80-4.71 (m, 2H), 4.54-4.43 (m, 2H), 3.78-3.45 (m, 4H), 2.78 (s, 3H), 2.62-2.22 (m, 3H). | Intermediate 2 and 4-Fluoro-3-phenoxy-benzaldehyde |

| Cmpd | Structure | Data | Starting Materials |
|---|---|---|---|
| 16 | 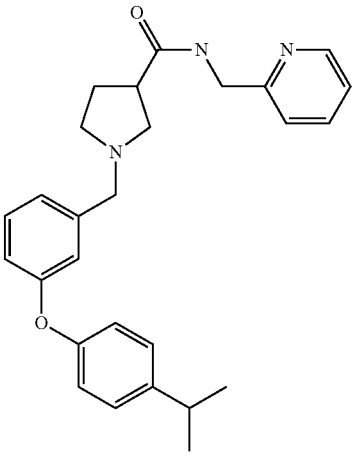 [SMILES: CC(C)c1ccc(Oc2cccc(CN3CCC(C(=O)NCc4ccccn4)C3)c2)cc1]<br>1-[3-(4-Isopropyl-phenoxy)-benzyl]-pyrrolidine-3-carboxylic acid (pyridin-2-ylmethyl)-amide | $^1$H NMR (CD$_3$OD) δ: 8.80-8.79 (m, 1H), 8.63-8.58 (m, 2H), 8.22-8.20 (m, 1H), 8.05 (d, J = 8.00 Hz, 1H), 8.02-7.99 (m, 1H), 7.92 (d, J = 8.96 Hz, 1H), 7.63-7.59 (m, 1H), 7.52-7.49 (m, 2H), 7.34 (dd, J = 8.20, 1.24 Hz, 1H), 4.80-4.71 (m, 2H), 4.54-4.43 (m, 2H), 3.78-3.45 (m, 4H), 2.78 (s, 3H), 2.62-2.22 (m, 3H). | Intermediate 2 and 3-(4-Isopropyl-phenoxy)-benzaldehyde |
| 17 | 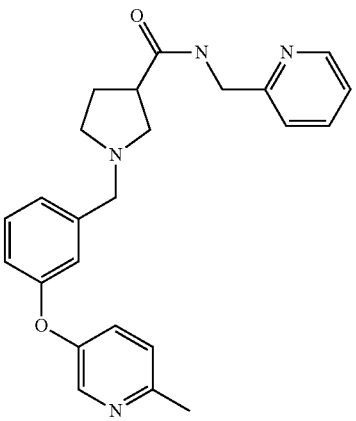 [SMILES: Cc1ccc(Oc2cccc(CN3CCC(C(=O)NCc4ccccn4)C3)c2)cn1]<br>1-(3-p-Tolyloxy-benzyl)-pyrrolidine-3-carboxylic acid (pyridin-2-ylmethyl)-amide | $^1$H NMR (CD$_3$OD) δ: 8.80-8.79 (m, 1H), 8.63-8.58 (m, 2H), 8.22-8.20 (m, 1H), 8.05 (d, J = 8.00 Hz, 1H), 8.02-7.99 (m, 1H), 7.92 (d, J = 8.96 Hz, 1H), 7.63-7.59 (m, 1H), 7.52-7.49 (m, 2H), 7.34 (dd, J = 8.20, 1.24 Hz, 1H), 4.80-4.71 (m, 2H), 4.54-4.43 (m, 2H), 3.78-3.45 (m, 4H), 2.78 (s, 3H), 2.62-2.22 (m, 3H). | Intermediate 2 and 3-p-Tolyloxy-benzaldehyde |
| 18 | 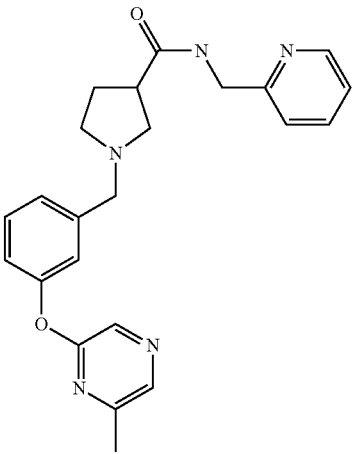 [SMILES: Cc1cncc(Oc2cccc(CN3CCC(C(=O)NCc4ccccn4)C3)c2)n1]<br>1-[3-(6-Methyl-pyrazin-2-yloxy)-benzyl]-pyrrolidine-3-carboxylic acid (pyridin-2-ylmethyl)-amide | $^1$H NMR (CD$_3$OD) δ: 8.49-8.47 (m, 1H), 8.19 (d, J = 4.76 Hz, 2H), 7.83-7.78 (m, 1H), 7.48 (t, J = 7.88 Hz, 1H), 7.37-7.30 (m, 4H), 7.20 (dd, J = 8.14, 1.60 Hz, 1H), 4.49 (s, 2H), 4.12-4.04 (m, 2H), 3.27-3.10 (m, 5H), 2.37 (s, 3H), 2.33-1.97 (m, 2H). | Intermediate 2 and 3-(6-Methyl-pyrazin-2-yloxy)-benzaldehyde |

| Cmpd | Structure | Data | Starting Materials |
|---|---|---|---|
| 19 | 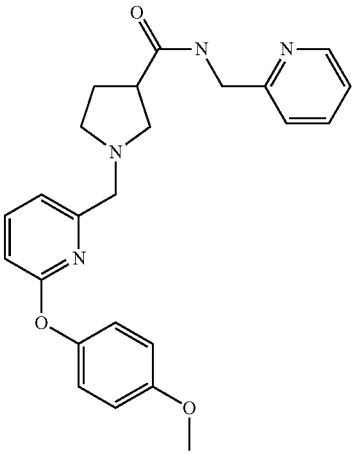<br>1-[6-(4-Methoxy-phenoxy)-pyridin-2-ylmethyl]-pyrrolidine-3-carboxylic acid (pyridin-2-ylmethyl)-amide | $^1$H NMR (CD$_3$OD) δ: 8.57-8.55 (m, 1H), 8.00-7.96 (m, 1H), 7.88-7.84 (m, 1H), 7.52-7.45 (m, 2H), 7.15 (d, J = 7.24 Hz, 1H), 7.08-7.05 (m, 2H), 6.98-6.96 (m, 3H), 4.57 (s, 2H), 4.50-4.40 (m, 2H), 3.80 (s, 3H), 3.70-3.60 (m, 2H), 3.32-3.30 (m, 2H), 2.70-2.00 (m, 3H). | Intermediate 2 and 6-(4-Melhoxy-phenoxy)-pyridine-2-carbaldehyde |
| 20 | 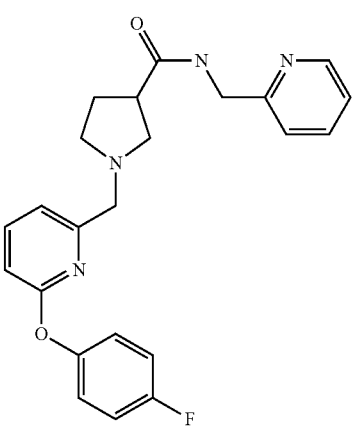 [SMILES: O=C(NCc1ccccn1)C1CCN(Cc2cccc(Oc3ccc(F)cc3)n2)C1]<br>1-[6-(4-Fluoro-phenoxy)-pyridin-2-ylmethyl]-pyrrolidine-3-carboxylic acid (pyridin-2-ylmethyl)-amide | $^1$H NMR (CD$_3$OD) δ: 8.48-8.47 (m, 1H), 7.83-7.75 (m, 2H), 7.35-7.30 (m, 2H), 7.18 (d, J = 7.20 Hz, 1H), 7.15-7.11 (m, 4H), 6.79 (d, J = 8.04 Hz, 1H), 4.48 (s, 2H), 3.75-3.67 (m, 2H), 3.07-2.93 (m, 2H), 2.82-2.66 (m, 3H), 2.15-2.01 (m, 2H). | Intermediate 2 and 6-(4-Fluoro-phenoxy)-pyridine-2-carbaldehyde |

| Cmpd | Structure | Data | Starting Materials |
|---|---|---|---|
| 21 | 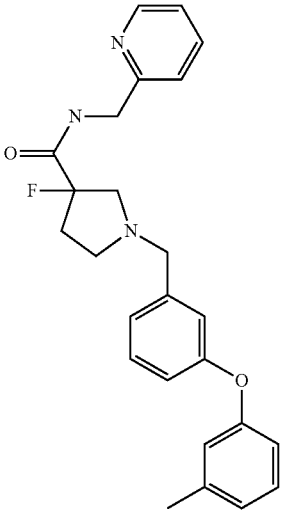 [SMILES: Cc1cccc(Oc2cccc(CN3CCC(F)(C(=O)NCc4ccccn4)C3)c2)c1]<br>3-Fluoro-1-(3-m-tolyloxy-benzyl)-pyrrolidine-3-carboxylic acid (pyridin-2-ylmethyl)-amide | $^1$H NMR (CD$_3$OD) δ: 8.58-8.56 (m, 1H), 8.00-7.98 (m, 1H), 7.55-7.46 (m, 3H), 7.28-7.25 (m, 2H), 7.20-7.19 (m, 1H), 7.11-7.09 (m, 1H), 7.01-6.99 (m, 1H), 6.87 (s, 1H), 6.84-6.81 (m, 1H), 4.69-4.59 (m, 2H), 4.50 (s, 2H), 3.99-3.83 (m, 2H), 3.73-3.60 (m, 2H), 2.78-2.55 (m, 2H), 2.33 (s, 3H). | Intermediate 4 and 3-m-Tolyloxy-benzaldehyde |
| 22 | 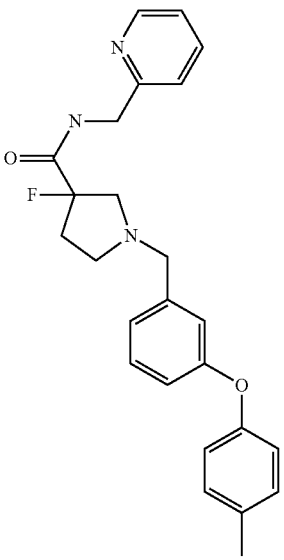 [SMILES: Cc1ccc(Oc2cccc(CN3CCC(F)(C(=O)NCc4ccccn4)C3)c2)cc1]<br>3-Fluoro-1-(3-p-tolyloxy-benzyl)-pyrrolidine-3-carboxylic acid (pyridin-2-ylmethyl)-amide | $^1$H NMR (CD$_3$OD) δ: 8.49-8.47 (m, 1H), 7.83-7.79 (m, 1H), 7.35-7.27 (m, 3H), 7.17-7.15 (m, 2H), 7.08 (d, J = 7.68 Hz, 1H), 7.00-6.99 (m, 1H), 6.90-6.85 (m, 3H), 4.54 (s, 2H), 3.74-3.64 (m, 2H), 3.14-2.88 (m, 3H), 2.66-2.60 (m, 1H), 2.55-2.46 (m, 1H), 2.32 (s, 3H), 2.30-2.15 (m, 1H). | Intermediate 4 and 3-p-Tolyloxy-benzaldehyde |

-continued

| Cmpd | Structure | Data | Starting Materials |
|---|---|---|---|
| 23 | 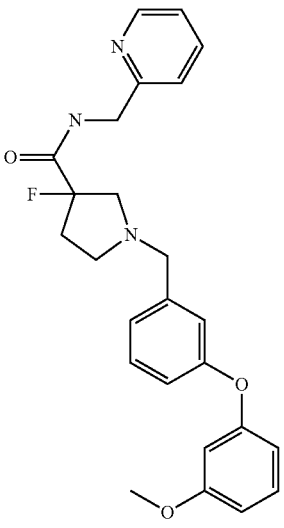 [SMILES: COc1cccc(Oc2cccc(CN3CCC(F)(C(=O)NCc4ccccn4)C3)c2)c1]<br>3-Fluoro-1-[3-(3-methoxy-phenoxy)-benzyl]-pyrrolidine-3-carboxylic acid (pyridin-2-ylmethyl)-amide | $^1$H NMR (DMSO-d$_6$) δ: 8.81-8.81 (m, 1H), 8.48-8.47 (m, 1H), 7.76-7.72 (m, 1H), 7.35-7.19 (m, 4H), 7.09 (d, J = 7.56 Hz, 1H), 6.98 (s, 1H), 6.91-6.88 (m, 1H), 6.72-6.69 (m, 1H), 6.58-6.54 (m, 2H), 4.39 (d, J = 5.96 Hz, 2H), 3.71 (s, 3H), 3.63-3.62 (m, 2H), 3.00-2.73 (m, 3H), 2.44-2.37 (m, 2H), 2.13-2.02 (m, 1H). | Intermediate 4 and 3-(3-Methoxy-phenoxy)-benzaldehyde |
| 24 | 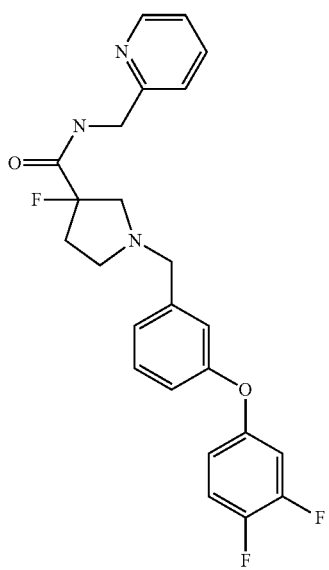 [SMILES: O=C(NCc1ccccn1)C1(F)CCN(Cc2cccc(Oc3ccc(F)c(F)c3)c2)C1]<br>1-[3-(3,4-Difluoro-phenoxy)-benzyl]-3-fluoro-pyrrolidine-3-carboxylic acid (pyridin-2-ylmethyl)-amide | $^1$H NMR (CD$_3$OD) δ: 8.49-8.48 (m, 1H), 7.81-7.79 (m, 1H), 7.37-7.16 (m, 5H), 7.07 (s, 1H), 6.95-6.92 (m, 3H), 4.54 (s, 2H), 3.75-3.66 (m, 2H) 3.11-2.88 (m, 3H), 2.66-2.60 (m, 1H), 2.55-2.42 (m, 1H), 2.30-2.17 (m, 1H). | Intermediate 4 and 3-(3,4-Difluoro-phenoxy)-benzaldehyde |

| Cmpd | Structure | Data | Starting Materials |
|---|---|---|---|
| 25 | 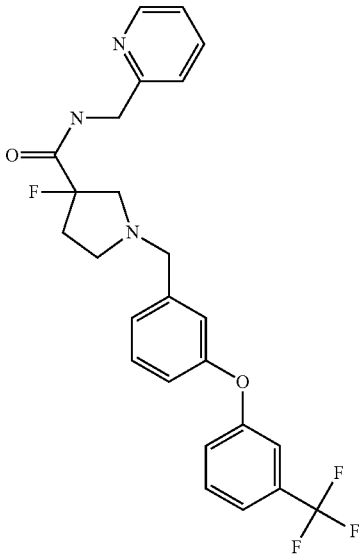 [SMILES: O=C(NCc1ccccn1)C1(F)CCN(Cc2cccc(Oc3cccc(C(F)(F)F)c3)c2)C1]<br>3-Fluoro-1-[3-(3-trifluoromethyl-phenoxy)-benzyl]-pyrrolidine-3-carboxylic acid (pyridin-2-ylmethyl)-amide | $^1$H NMR (CD$_3$OD) δ: 8.49-8.47 (m, 1H), 7.83-7.78 (m, 1H), 7.56-7.52 (m, 1H), 7.41-7.29 (m, 4H), 7.24-7.21 (m, 3H), 7.12-7.11 (m, 1H), 7.00-6.99 (m, 1H), 4.54 (s, 2H), 3.77-3.32 (m, 2H), 3.12-2.89 (m, 3H), 2.64-2.60 (m, 1H), 2.55-2.42 (m, 1H), 2.28-2.17 (m, 1H). | Intermediate 4 and 3-(3-Trifluoromethyl-phenoxy)-benzaldehyde |
| 26 | 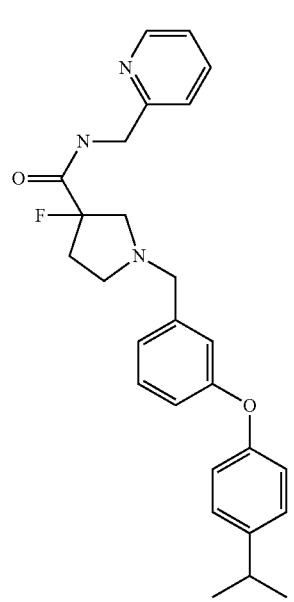 [SMILES: CC(C)c1ccc(Oc2cccc(CN3CCC(F)(C(=O)NCc4ccccn4)C3)c2)cc1]<br>3-Fluoro-1-[3-(4-isopropyl-phenoxy)-benzyl]-pyrrolidine-3-carboxylic acid (pyridin-2-ylmethyl)-amide | $^1$H NMR (CD$_3$OD) δ: 8.49-8.47 (m, 1H), 7.83-7.79 (m, 1H), 7.35-7.21 (m, 5H), 7.08 (d, J = 7.72 Hz, 1H), 7.01-7.00 (m, 1H), 6.93-6.87 (m, 3H), 4.54 (s, 2H), 3.73-3.63 (m, 2H), 3.11-2.87 (m, 4H), 2.63-2.58 (m, 1H), 2.51-2.43 (m, 1H), 2.27-2.16 (m, 1H), 1.25 (d, J = 6.92 Hz, 6H). | Intermediate 4 and 3-(4-Isopropyl-phenoxy)-benzaldehyde |

-continued

| Cmpd | Structure | Data | Starting Materials |
|---|---|---|---|
| 27 | 3-Methyl-1-[3-(pyrimidin-2-yloxy)-benzyl]-pyrolidine-3-carboxylic acid (pyridin-2-ylmethyl)-amide | $^1$H NMR (CD$_3$OD) δ: 8.56 (d, J = 4.84 Hz, 2H), 8.47-8.46 (m, 1H), 7.78-7.74 (m, 1H), 7.39-7.35 (m, 1H), 7.29-7.24 (m, 4H), 7.19 (t, J = 4.84 Hz, 1H), 7.10-7.07 (m, 1H), 4.50-4.41 (m, 2H), 3.77 (s, 2H), 3.22-3.20 (m, 1H), 3.01-2.97 (m, 1H), 2.65-2.63 (m, 1H), 2.41-2.28 (m, 2H), 1.83-1.76 (m, 1H), 1.34 (s, 3H). | Intermediate 6 and 3-(Pyrimidin-2-yloxy)-benzaldehyde |
| 28 | 1-[1-(3-Isobutoxy-benzyl)-pyrrolidin-3-ylmethyl]-1H-imidazole | $^1$H NMR (DMSO-d$_6$): δ 7.48 (s, 1H), 7.22 (t, J = 8.04 Hz, 1H), 7.06 (s, 1H), 6.79-6.89 (m, 4H), 3.88-3.97 (m, 2H), 3.72 (d, J = 6.52 Hz, 2H), 3.54-3.64 (m, 2H), 2.36-2.74 (m, 5H), 1.95-2.13 (m, 2H), 1.49-1.56 (m, 1H), 1.03 (d, J = 6.68 Hz, 6H). | Intermediate 9 and 3-Isobutoxy-benzaldehyde |
| 29 | 1-Biphenyl-3-ylmethyl-pyrrolidine-3-carboxylic acid (pyridin-2-ylmethyl)-amide | $^1$H NMR (DMSO-d$_6$): δ 8.45-8.46 (m, 1H), 8.39 (t, J = 6.00 Hz, 1H), 7.23-7.72 (m, 12H), 4.32 (d, J = 5.88 Hz, 2H), 3.64 (s, 2H), 2.63-2.96 (m, 3H), 2.48-2.51 (m, 2H), 1.93-1.96 (m, 2H). | Intermediate 1 and 3-biphenylcarboxaldehyde |

-continued

| Cmpd | Structure | Data | Starting Materials |
|---|---|---|---|
| 30 | 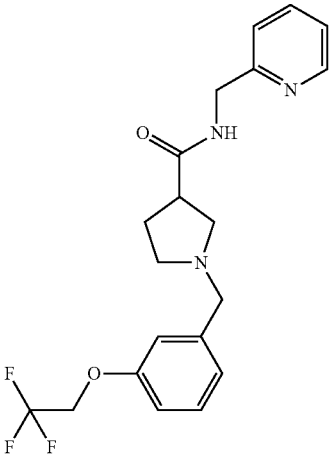 [SMILES: O=C(NCc1ccccn1)C1CCN(Cc2cccc(OCC(F)(F)F)c2)C1]<br>1-[3-(2,2,2-Trifluoro-ethoxy)-benzyl]-pyrrolidine-3-carboxylic acid (pyridin-2-ylmethyl)-amide | $^1$H NMR (DMSO-d$_6$): δ 8.46-8.48 (m, 1H), 8.38-8.41 (m, 1H), 7.71-7.75 (m, 1H), 7.19-7.28 (m, 3H), 6.90-6.99 (m, 3H), 4.69-4.76 (m, 2H), 4.33 (d, J = 5.88 Hz, 2H), 3.54 (s, 2H), 2.40-2.93 (m, 5H), 1.92-1.96 (m, 2H). | Intermediate 1 and 3-(2,2,2-Trifluoro-ethoxy)-benzaldehyde |
| 31 | 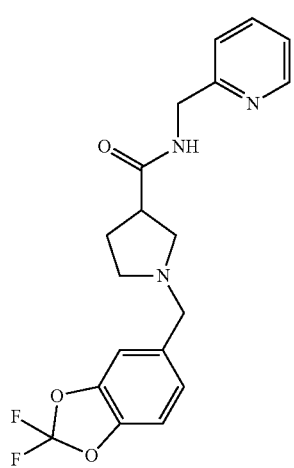 [SMILES: O=C(NCc1ccccn1)C1CCN(Cc2ccc3c(c2)OC(F)(F)O3)C1]<br>1-(2,2-Difluoro-benzo[1,3]dioxol-5-ylmethyl)-pyrrolidine-3-carboxylic acid (pyridin-2-ylmethyl)-amide | $^1$H NMR (DMSO-d$_6$): δ 8.46-8.48 (m, 1H), 8.39 (t, J = 5.84 Hz, 1H), 7.71-7.75 (m, 1H), 7.12-7.34 (m, 5H), 4.33 (d, J = 5.88 Hz, 2H), 3.57 (s, 2H), 2.39-2.95 (m, 5H), 1.90-1.96 (m, 2H). | Intermediate 1 and 2,2-Difluoro-benzo[1,3]dioxole-5-carbaldehyde |

| Cmpd | Structure | Data | Starting Materials |
|---|---|---|---|
| 32 | 1-(2,2-Dimethyl-2,3-dihydro-benzofuran-5-ylmethyl)-pyrrolidine-3-carboxylic acid (pyridin-2-ylmethyl)-amide | $^1$H NMR (CDCl$_3$): δ 8.54 (d, J = 4.64 Hz, 1H), 7.65-7.69 (m, 1H), 7.59 (s, 1H), 7.37 (s, 3H), 7.16-7.27 (m, 3H), 6.67 (d, J = 8.12 Hz, 1H), 4.55 (d, J = 4.88 Hz, 2H), 3.97 (s, 2H), 2.98-3.27 (m, 7H), 2.19-2.46 (m, 6H). | Intermediate 1 and 2,2-Dimethyl-2,3-dihydro-benzofuran-5-carbaldehyde |
| 33 | 1-(2,2-Dimethyl-benzo[1,3]dioxol-5-ylmethyl)-pyrrolidine-3-carboxylic acid (pyridin-2-ylmethyl)-amide | $^1$H NMR (DMSO-d$_6$): δ 8.55 (br s, 1H), 8.48 (d, J = 6.36 Hz, 1H), 7.72-7.76 (m, 1H), 7.22-7.26 (m, 2H), 6.79 (s, 3H), 4.34 (d, J = 5.88 Hz, 2H), 3.85 (br s, 3H), 3.06 (br s, 4H), 2.03 (br s, 2H), 1.62 (s, 6H). | Intermediate 1 and 2,2-Dimethyl-benzo[1,3]dioxole-5-carbaldehyde |
| 34 | 1-[1-(3-Isobutoxy-benzyl)-pyrrolidin-3-ylmethyl]-1H-imidazole | $^1$H NMR (DMSO-d$_6$): δ 8.13 (s, 1H), 7.69 (s, 1H), 7.19 (t, J = 7.44 Hz, 1H), 6.78-6.84 (m, 3H), 4.35 (t, J = 6.72 Hz, 2H), 3.71 (d, J = 6.48 Hz, 2H), 3.21-3.51 (m, 2H), 2.28-2.66 (m, 3H), 1.41-2.02 (m, 3H), 0.94 (d, J = 6.72 Hz, 6H). | Intermediate 16 and Intermediate 22 |

| Cmpd | Structure | Data | Starting Materials |
|---|---|---|---|
| 35 | 2-[1-(3-Isobutoxy-benzyl)-pyrrolidin-3-ylmethoxymethyl]-pyridine | ¹H NMR (CDCl3): δ 8.55 (d, J = 4.28 Hz, 1H), 7.68-7.72 (m, 1H), 7.40 (d, J = 7.84 Hz, 1H), 7.18-7.27 (m, 2H), 6.82-6.99 (m, 3H), 4.63 (s, 2H), 3.73-3.80 (m, 4H), 3.52-3.54 (m, 2H), 2.54-2.95 (m, 5H), 2.03-2.13 (m, 2H), 1.65 (s, 1H), 1.03 (d, J = 6.68 Hz, 6H). | Intermediate 20 and Intermediate 22 |
| 36 | Pyridine-2-carboxylic acid [1-(3-isopropoxymethyl-benzyl)-pyrrolidin-3-ylmethyl]-amide | ¹H NMR (CDCl₃): δ 8.61 (d, J = 4.72 Hz, 1H), 8.50 (s, 1H), 8.19 (d, J = 7.80 Hz, 1H), 7.83-7.87 (m, 1H), 7.42-7.45 (m, 1H), 6.99-7.24 (m, 3H), 6.81 (d, J = 8.04 Hz, 1H), 3.71-3.72 (m, 4H), 3.47-3.56 (m, 2H), 2.82 (bs, 2H), 2.62 (bs, 3H), 2.03-2.11 (m, 2H), 1.67-1.69 (m, 1H), 1.01 (d, J = 6.68 Hz, 6H). | Intermediate 21 and Intermediate 22 |
| 37 | (R)-3-methyl-1-(3-phenoxybenzyl)-N-(pyridin-2-ylmethyl)pyrrolidine-3-carboxamide | ¹H NMR : 400 MHz, DMSO-d₆: δ 8.41-8.42 (m, 2H), 8.21-8.24 (m, 1H), 7.56-7.58 (m, 1H), 7.35-7.39 (m, 2H), 7.27-7.32 (m, 2H), 7.10-7.14 (m, 1H), 7.04 (d, J = 4.80 Hz, 1H), 6.98 (dd, J = 0.96, 1.90 Hz, 2H), 6.93-6.94 (m, 1H), 6.85-6.87 (m, 1H), 4.24-4.26 (m, 2H), 3.50-3.58 (m, 2H), 2.78 (d, J = 9.20 Hz, 1H), 2.53-2.56 (m, 2H), 2.21-2.32 (m, 2H), 1.51-1.56 (m, 1H), 1.21-1.28 (m, 3H). | Intermediate 38 and 2-aminomethyl-2-pyridine |

-continued

| Cmpd | Structure | Data | Starting Materials |
|---|---|---|---|
| 38 | 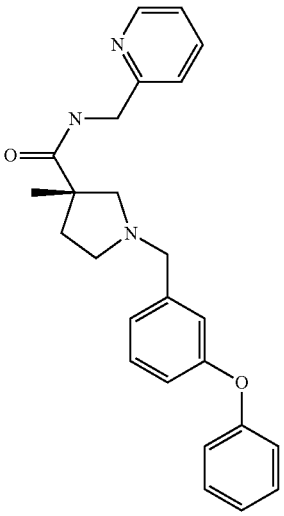 [SMILES: C[C@]1(C(=O)NCc2ccccn2)CCN(Cc2cccc(Oc3ccccc3)c2)C1]<br>(S)-3-methyl-1-(3-phenoxybenzyl)-N-(pyridin-2-ylmethyl)pyrrolidine-3-carboxamide | $^1$H NMR: 400 MHz, DMSO-$d_6$: δ 8.41-8.42 (m, 2H), 8.21-8.24 (m, 1H), 7.56-7.58 (m, 1H), 7.35-7.39 (m, 2H), 7.27-7.32 (m, 2H), 7.10-7.14 (m, 1H), 7.04 (d, J = 4.80 Hz, 1H), 6.98 (dd, J = 0.96, 1.90 Hz, 2H), 6.93-6.94 (m, 1H), 6.85-6.87 (m, 1H), 4.24-4.26 (m, 2H), 3.50-3.58 (m, 2H), 2.78 (d, J = 9.20 Hz, 1H), 2.53-2.56 (m, 2H), 2.21-2.32 (m, 2H), 1.51-1.56 (m, 1H), 1.21-1.28 (m, 3H). | Intermediate 38 and 2-aminomethyl-2-pyridine |
| 39 | 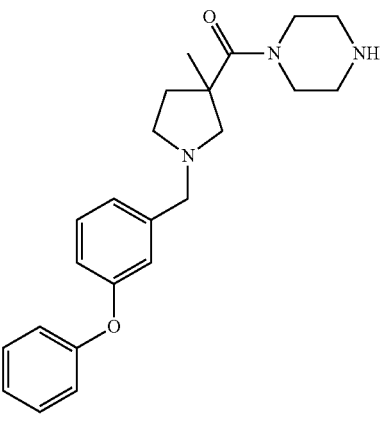 [SMILES: CC1(C(=O)N2CCNCC2)CCN(Cc2cccc(Oc3ccccc3)c2)C1]<br>[3-Methyl-1-(3-phenoxy-benzyl)-pyrrolidin-3-yl]-piperazin-1-yl-methanone | $^1$H NMR: 400 MHz, DMSO-$d_6$: δ 7.36-7.40 (m, 2H), 7.29-7.33 (m, 1H), 7.11-7.15 (m, 1H), 7.04-7.05 (m, 1H), 6.98-7.01 (m, 2H), 6.92-0.00 (m, 1H), 6.86-6.88 (m, 1H), 3.50 (s, 2H), 3.32-3.40 (m, 4H), 3.01-3.12 (m, 1H), 2.85 (d, J = 9.32 Hz, 1H), 2.85-2.63 (m, 4H), 2.30-2.38 (m, 2H), 2.15-2.21 (m, 1H), 1.64-1.70 (m, 1H), 1.22 (s, 4H). LCMS: 380.2 (M + H), Rt. 2.9 min, 96.2% (max), 95.9% (220 nm). | Intermediate 38 and piperizine |
| 40 | 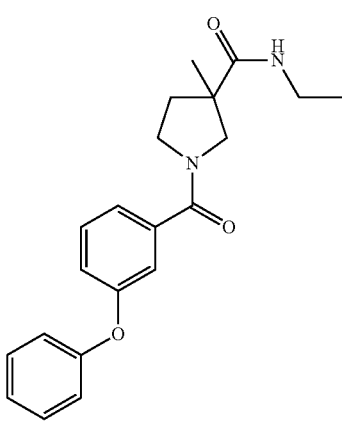 [SMILES: CCNC(=O)C1(C)CCN(C(=O)c2cccc(Oc3ccccc3)c2)C1]<br>3-Methyl-1-(3-phenoxy-benzoyl)-pyrrolidine-3-carboxylic acid ethylamide | $^1$H NMR: 400 MHz, DMSO-$d_6$: δ 7.72-7.73 (m, 1H), 7.39-7.47 (m, 3H), 7.15-7.25 (m, 2H), 7.02-7.10 (m, 4H), 3.72-3.79 (m, 1H), 3.40-3.46 (m, 2H), 3.14-3.27 (m, 1H), 3.02-3.09 (m, 2H), 1.98-2.00 (m, 1H), 1.73-1.78 (m, 1H), 1.23-1.25 (m, 3H), 0.94-1.01 (m, 3H). | Intermediate 40 and ethylamine |

| Cmpd | Structure | Data | Starting Materials |
|---|---|---|---|
| 41 | 3-Methyl-1-(3-trifluoromethoxy-benzyl)-pyrrolidine-3-carboxylic acid ethylamide | ¹H NMR: 400 MHz, DMSO-d₆: δ 7.55-7.58 (m, 1H), 7.43-7.47 (m, 1H), 7.31-7.36 (m, 1H), 7.28-0.00 (m, 1H), 7.21-7.24 (m, 1H), 3.60-0.00 (m, 2H), 3.02-3.08 (m, 2H), 2.75 (d, J = 9.16 Hz, 1H), 2.53-2.57 (m, 2H), 2.19-2.25 (m, 2H), 1.48-1.54 (m, 1H), 1.19-1.54 (m, 3H), 0.96-0.99 (m, 3H). | Intermediate 42 and ethylamine |
| 42 | 1-[3-(2-Methyl-propane-1-sulfinyl)-benzyl]-pyrrolidine-3-carboxylic acid (pyridin-2-ylmethyl)-amide | ¹H NMR: 400 MHz, DMSO-d₆: δ 8.47-8.48 (m, 1H), 8.41 (t, J = 5.84 Hz, 1H), 7.73 (s, 1H), 7.61-0.00 (m, 1H), 7.45-7.53 (m, 3H), 7.19-7.25 (m, 2H), 4.33 (d, J = 5.92 Hz, 2H), 3.65 (s, 2H), 2.60-3.16 (m, 5H), 2.42-2.45 (m, 2H), 1.91-2.07 (m, 3H), 1.07 (d, J = 6.64 Hz, 3H), 0.96-0.97 (m, 3H). LCMS: 400.2 (M + 1), Rt. 2.01 min, 96.8% (max), 97.7% (254 nm). | Intermediate 2 and Intermediate 60 |
| 43 | 1-(3-m-Tolyloxy-benzyl)-pyrrolidine-3-carboxylic acid (pyridin-2-ylmethyl)-amide | 400 MHz, DMSO-d₆: 8.47 (d, J = 4.76 Hz, 1H), 8.40 (t, J = 6.08 Hz, 1H), 7.75-7.70 (m, 1H), 7.32-7.19 (m, 4H), 7.06 (d, J = 7.56 Hz, 1H), 6.95-6.93 (m, 2H), 6.86-6.76 (m, 3H), 4.32 (d, J = 5.84 Hz, 2H), 3.55 (s, 2H), 2.94-2.90 (m, 1H), 2.78 (t, J = 8.24 Hz, 1H), 2.65-2.55 (m, 2H), 2.48-2.30 (m, 1H), 2.27 (s, 3H), 1.95-1.91 (m, 2H). | Intermediate 2 and 3-m-tolyloxy benzaldehyde |

| Cmpd | Structure | Data | Starting Materials |
|---|---|---|---|
| 44 | 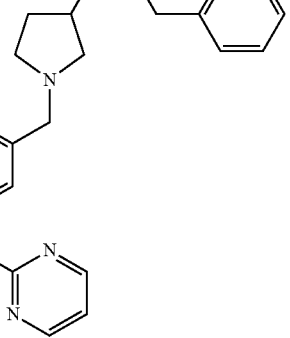<br>1-[3-(Pyrimidin-2-yloxy)-benzyl]-pyrrolidine-3-carboxylic acid (pyridin-2-ylmethyl)-amide | 400 MHz, MeOD: 8.60 (d, J = 4.80 Hz, 2H), 8.49 (d, J = 4.24 Hz, 1H), 7.83-7.79 (m, 1H), 7.52 (t, J = 7.84 Hz, 1H), 7.40-7.30 (m, 4H), 7.27-7.22 (m, 2H), 4.54-4.46 (m, 2H), 4.27-4.19 (m, 2H), 3.32-3.24 (m, 5H), 2.39-2.33 (m, 1H), 2.24-2.19 (m, 1H). | Intermediate 2 and 3-pyrimidin-2yloxy-benzaldehyde |
| 45 | <br>3-Methyl-1-(3-m-tolyloxy-benzyl)-pyrrolidine-3-carboxylic acid (pyridin-2-ylmethyl)-amide | 400 MHz, MeOD: 8.48-8.47 (m, 1H), 7.81-7.76 (m, 1H), 7.39-7.28 (m, 3H), 7.23 (t, J = 7.84 Hz, 1H), 7.16 (d, J = 7.56 Hz, 1H), 7.10 (s, 1H), 6.99-6.95 (m, 2H), 6.82 (s, 1H), 6.78-6.76 (m, 1H), 4.48 (s, 2H), 4.10-3.90 (m, 2H), 3.60-3.50 (m, 1H), 3.05-2.43 (m, 4H), 2.31 (s, 3H), 2.00-1.90 (m, 1H), 1.42 (s, 3H). | Intermediate 6 and 3-m-tolyloxy-benzaldehyde |

Example 2

1-(3-Isobutylsulfanyl-benzyl)-pyrrolidine-3-carboxylic acid pyridin-2-ylmethyl ester (46)

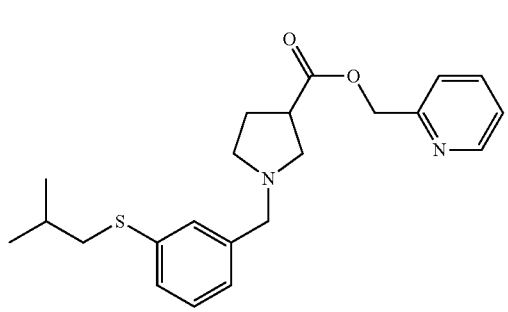 [SMILES: CC(C)CSc1cccc(CN2CCC(C(=O)OCc3ccccn3)C2)c1]

1-Chloromethyl-3-isobutylsulfanyl-benzene (Intermediate 12, 0.23 g, 1.09 mmol) was taken in dry DMF (10 mL) and potassium carbonate (0.45 g, 3017 mmol), and Pyrrolidine-3-carboxylic acid (pyridin-2-ylmethyl)-amide hydrochloride (Intermediate 1, 0.31 g, 1.31 mmol) were added, and the reaction mixture was stirred at room temperature for 12 h. The reaction mixture was filtered through celite and concentrated under reduced pressure to provide the crude product which was purified by column chromatography (pet ether/ethyl acetate 20%). Yield: 15% (65 mg, colorless liquid); $^1$H NMR: 400 MHz, (DMSO-$d_6$): δ 8.40-8.48 (m, 2H), 7.71-7.75 (m, 1H), 7.08-7.25 (m, 6H), 4.33 (d, J=5.88 Hz, 2H), 3.53 (s, 2H), 2.39-2.95 (m, 7H), 1.73-1.96 (m, 3H), 0.96 (d, J=6.64 Hz, 6H).

The following compounds were synthesized according to the procedure in Example 2 from the starting materials indicated in the table.

Example 3

2-{3-[1-(3-Isobutoxy-benzyl)-pyrrolidin-3-yl]-[1,2,4]oxadiazol-5-yl}-pyridine (48)

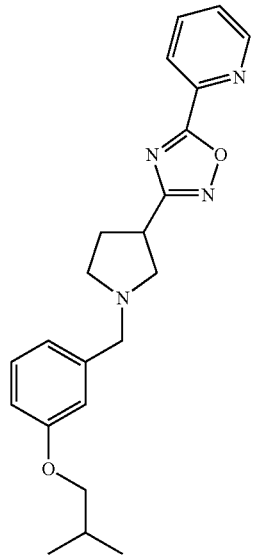 [SMILES: CC(C)COc1cccc(CN2CCC(c3noc(-c4ccccn4)n3)C2)c1]

N-Hydroxy-1-(3-isobutoxy-benzyl)-pyrrolidine-3-carboxamidine (Intermediate 26, 0.2 g, 0.69 mmol) was taken in dry THF (3 mL) and to this was added picolinic acid (0.1 g, 0.83 mmol), triethyl amine (0.29 mL, 2.07 mmol) and 50% solution of T3P in ethyl acetate (0.64 mL, 1.03 mmol). The reaction mixture was heated to reflux at 10 h. The reaction mixture was cooled to room temperature and treated with 10% aqueous solution of sodium bicarbonate, and extracted with ethyl acetate. The organic layer was washed with brine and dried over anhydrous sodium sulphate to get the crude material, which was purified by column chromatography (pet ether/ethyl acetate 20%) to provide the titled compound as a colorless gummy solid (12%, 33 mg). $^1$H NMR: (DMSO-$d_6$): δ 8.80 (s, 1H), 8.22 (d, J=7.88 Hz, 1H), 8.07-8.09 (m, 1H), 7.68-7.71 (m, 1H), 7.20 (t, J=8.00 Hz, 1H), 6.87 (t, J=7.16 Hz, 2H), 6.68-6.78 (m, 1H), 3.55-3.70 (m, 5H), 1.95-2.94 (m, 7H), 0.94 (d, J=6.72 Hz, 6H). LCMS: 379.2 (M+1), Rt. 3.82 min, 91.7% (max), 99.1% (254 nm).

The following Examples were synthesized according to the procedure described for Example 3 from the starting materials listed in the table.

| Cmpd | Structure | Data | Starting Materials |
|---|---|---|---|
| 47 | 1-[3-(2-Methyl-propane-1-sulfonyl)-benzyl]-pyrrolidine-3-carboxylic acid pyridin-2-ylmethyl ester | $^1$H NMR (DMSO-$d_6$): δ 8.47 (d, J = 4.80 Hz, 1H), 8.40-8.41 (m, 1H), 7.83 (s, 1H), 7.57-7.78 (m, 4H), 7.19-7.25 (m, 2H), 4.33 (d, J = 5.88 Hz, 2H), 3.68 (s, 2H), 3.19 (d, J = 6.64 Hz, 2H), 2.49-2.97 (m, 5H), 0.94 (d, J = 6.72 Hz, 6H). | Intermediate 1 and Intermediate 15 |

| Cmpd | Structure | Data | Starting Materials |
|---|---|---|---|
| 49 | 2-{3-[1-(3-Isobutoxy-benzyl)-pyrrolidin-3-yl]-[1,2,4]oxadiazol-5-yl}-3-methoxy-pyridine | $^1$H NMR: (DMSO-d$_6$): δ 8.34-8.35 (m, 1H), 7.61-7.81 (m, 2H), 7.17-7.21 (m, 1H), 6.77-6.87 (m, 3H), 3.93 (s, 3H), 3.54-3.70 (m, 5H), 2.62-2.96 (m, 3H), 1.95-2.31 (m, 3H), 0.94 (d, J = 6.68 Hz, 6H). LCMS: 409.2 (M + 1), Rt. 3.82 min, 98.4% (max), 98.4% (220 nm). | Intermediate 26 and 2-hydroxy-picolinc acid |
| 50 | 3-Fluoro-2-{3-[1-(3-isobutoxy-benzyl)-pyrrolidin-3-yl]-[1,2,4]oxadiazol-5-yl}-pyridine | $^1$H NMR: (DMSO-d$_6$): δ 8.67-8.68 (m, 1H), 8.04-8.09 (m, 1H), 7.81-7.85 (m, 1H), 7.20 (t, J = 7.96 Hz, 1H), 6.86-6.88 (m, 2H), 6.77-6.79 (m, 1H), 3.55-3.70 (m, 5H), 2.92-2.97 (m, 1H), 2.64-2.75 (m, 3H), 2.25-2.29 (m, 1H), 1.93-2.15 (m, 2H), 0.94 (d, J = 6.68 Hz, 6H). LCMS: 397.2 (M + 1), Rt. 3.84 min, 92.8% (max). | Intermediate 26 and 2-fluoro-picolinic acid |

| Cmpd | Structure | Data | Starting Materials |
|---|---|---|---|
| 51 | 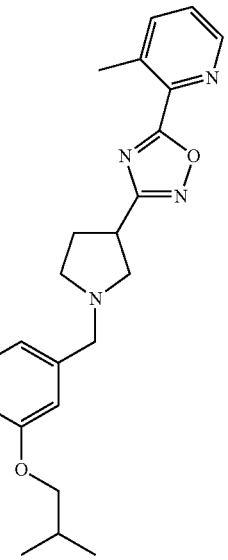<br>2-{3-[1-(3-Isobutoxy-benzyl)-pyrrolidin-3-yl]-[1,2,4]oxadiazol-5-yl}-3-methyl-pyridine | $^1$H NMR: (DMSO-$d_6$): δ 8.62-8.63 (m, 1H), 7.91-7.93 (m, 1H), 7.57-7.60 (m, 1H), 7.17-7.21 (m, 1H), 6.86-6.88 (m, 3H), 3.54-3.70 (m, 5H), 1.94-2.94 (m, 9H), 0.94 (d, J = 6.68 Hz, 6H). LCMS: 393.0 (M + 1), Rt. 4.01 min, 96.2% (max), 95.6% (220 nm). | Intermediate 26 and 2-methyl-picolinic acid |
| 52 | 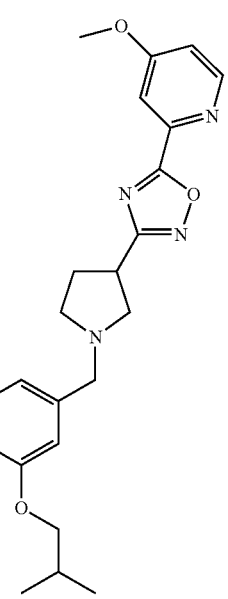<br>2-{3-[1-(3-Isobutoxy-benzyl)-pyrrolidin-3-yl]-[1,2,4]oxadiazol-5-yl}-4-methoxy-pyridine | $^1$H NMR: (DMSO-$d_6$): δ 8.59 (s, 1H), 7.69-7.70 (m, 1H), 7.18-7.28 (m, 2H), 6.77-6.88 (m, 3H), 3.94 (s, 3H), 3.55-3.70 (m, 5H), 2.92-2.96 (m, 1H), 2.59-2.74 (m, 3H), 1.95-2.48 (m, 3H), 0.94 (d, J = 6.68 Hz, 6H). | Intermediate 26 and 4-methoxy-picolinic acid |

| Cmpd | Structure | Data | Starting Materials |
|---|---|---|---|
| 53 | 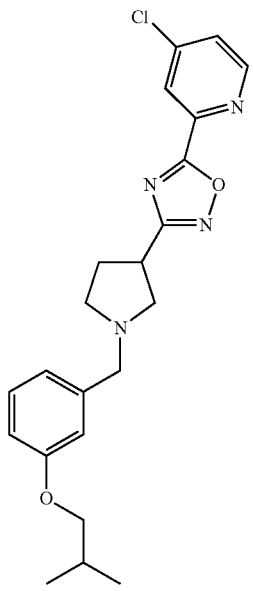 [SMILES: CC(C)COc1cccc(CN2CCC(c3noc(-c4cc(Cl)ccn4)n3)C2)c1]<br>4-Chloro-2-{3-[1-(3-isobutoxy-benzyl)-pyrrolidin-3-yl]-[1,2,4]oxadiazol-5-yl}-pyridine | ¹H NMR: (DMSO-d₆): δ 8.78 (d, J = 5.28 Hz, 1H), 8.27 (d, J = 2.00 Hz, 1H), 7.87-7.88 (m, 1H), 7.18-7.21 (m, 1H), 6.86-6.87 (m, 2H), 6.77-6.80 (m, 1H), 3.55-3.70 (m, 5H), 2.92-2.96 (m, 1H), 2.62-2.74 (m, 3H), 2.10-2.31 (m, 2H), 1.95-1.98 (m, 1H), 0.94 (d, J = 6.68 Hz, 6H). | Intermediate 26 and 4-chloro-picolinic acid |
| 54 | 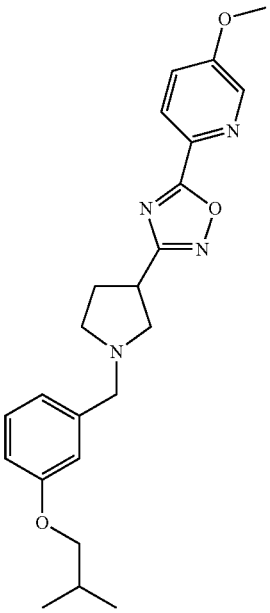 [SMILES: COc1ccc(-c2nc(C3CCN(Cc4cccc(OCC(C)C)c4)C3)no2)nc1]<br>2-{3-[1-(3-Isobutoxy-benzyl)-pyrrolidin-3-yl]-[1,2,4]oxadiazol-5-yl}-5-methoxy-pyridine | ¹H NMR: (DMSO-d₆): δ 8.18-8.48 (m, 2H), 7.59-7.62 (m, 1H), 7.17-7.21 (m, 1H), 6.77-6.87 (m, 3H), 3.93 (s, 3H), 3.62-3.86 (m, 5H), 1.95-2.96 (m, 5H), 0.94 (d, J = 6.68 Hz, 6H). | Intermediate 26 and 5-methoxy-picolinic acid |

| Cmpd | Structure | Data | Starting Materials |
|---|---|---|---|
| 55 | 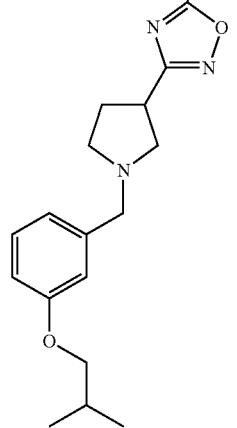<br>2-{3-[1-(3-Isobutoxy-benzyl)-pyrrolidin-3-yl]-[1,2,4]oxadiazol-5-yl}-5-methyl-pyridine | $^1$H NMR: (DMSO-d$_6$): δ 8.65 (s, 1H), 8.12 (d, J = 7.96 Hz, 1H), 7.88 (d, J = 8.36 Hz, 1H), 7.20 (t, J = 7.16 Hz, 1H), 6.77-6.87 (m, 3H), 3.58-3.70 (m, 5H), 2.71-2.96 (m, 1H), 1.93-2.66 (m, 7H), 0.94 (d, J = 6.68 Hz, 6H). | Intermediate 26 and 5-methyl-picolinic acid |
| 56 | 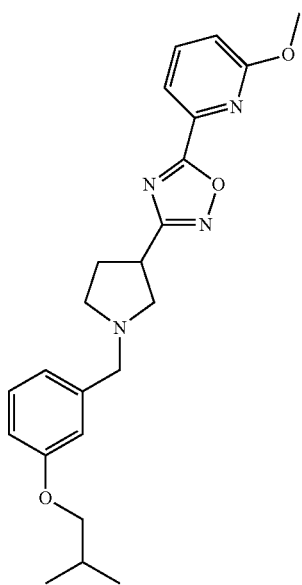 [SMILES: COc1cccc(-c2nc(C3CCN(Cc4cccc(OCC(C)C)c4)C3)no2)n1]<br>2-{3-[1-(3-Isobutoxy-benzyl)-pyrrolidin-3-yl]-[1,2,4]oxadiazol-5-yl}-6-methoxy-pyridine | $^1$H NMR: (DMSO-d$_6$): δ 7.93-7.97 (m, 1H), 7.84 (d, J = 6.76 Hz, 1H), 7.13-7.22 (m, 2H), 6.86-6.87 (m, 2H), 6.77-6.79 (m, 1H), 3.95 (s, 3H), 3.54-3.70 (m, 5H), 2.91-2.95 (m, 1H), 2.62-2.75 (m, 3H), 2.24-2.28 (m, 1H), 1.93-2.12 (m, 2H), 0.94 (d, J = 6.68 Hz, 6H). | Intermediate 26 and 6-methoxy-picolinic acid |

-continued

| Cmpd | Structure | Data | Starting Materials |
|---|---|---|---|
| 57 | 2-{3-[1-(3-Isobutoxy-benzyl)-pyrrolidin-3-yl]-[1,2,4]oxadiazol-5-ylmethyl}-pyridine | $^1$H NMR: (DMSO-d$_6$): δ 8.48-8.49 (m, 1H), 7.78-7.82 (m, 1H), 7.16-7.45 (m, 3H), 6.77-6.85 (m, 3H), 4.47 (s, 2H), 3.33-3.71 (m, 5H), 2.88 (t, J = 8.84 Hz, 1H), 2.54-2.66 (m, 3H), 2.15-2.21 (m, 1H), 1.93-2.01 (m, 2H), 0.95-0.97 (m, 6H). LCMS: 393.2 (M + 1), Rt. 3.29 min, 93.1% (max), 93.3% (220 nm). | Intermediate 26 and 3-pyridyl-benzoic acid |
| 58 | 4-Bromo-2-{3-[1-(3-isobutoxy-benzyl)-pyrrolidin-3-yl]-[1,2,4]oxadiazol-5-yl}-pyridine | $^1$H NMR: 400 MHz, DMSO-d$_6$: δ 8.69 (d, J = 5.04 Hz, 1H), 8.38 (d, J = 1.68 Hz, 1H), 8.00-8.02 (m, 1H), 7.18-7.22 (m, 1H), 6.86-6.87 (m, 2H), 6.77-6.80 (m, 1H), 3.55-3.70 (m, 5H), 2.92-2.96 (m, 1H), 2.66-2.74 (m, 3H), 2.24-2.28 (m, 1H), 1.93-2.13 (m, 2H), 0.94 (d, J = 6.68 Hz, 6H). LCMS: 457.0 (M + 1), Rt. 4.23 min, 90.8% (max), 94.2% (254 nm). | Intermediate 26 and 4-bromo-picolinic acid |

| Cmpd | Structure | Data | Starting Materials |
|---|---|---|---|
| 59 | 5-Fluoro-2-{3-[1-(3-isobutoxy-benzyl)-pyrrolidin-3-yl]-[1,2,4]oxadiazol-5-yl}-pyridine | $^1$H NMR: 400 MHz, DMSO-$d_6$: δ 8.83 (s, 1H), 8.30-8.33 (m, 1H), 7.99-8.03 (m, 1H), 7.18-7.22 (m, 1H), 6.77-6.87 (m, 3H), 3.55-3.70 (m, 5H), 2.94 (s, 1H), 2.61-2.74 (m, 3H), 1.95-2.31 (m, 3H), 0.94 (d, J = 6.68 Hz, 6H). | Intermediate 26 and 5-fluoro-picolinic acid |

Example 4

2-{1-[1-(3-Isobutoxy-benzyl)-pyrrolidin-3-yl]-1H-[1,2,3]triazol-4-yl}-pyridine (60)

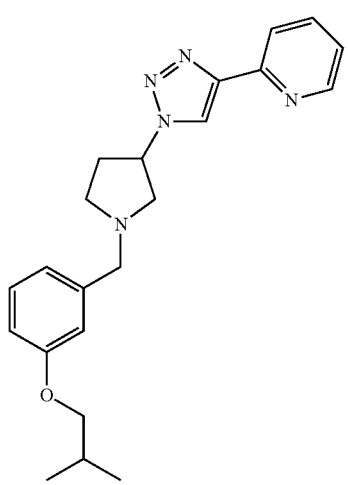 [SMILES: CC(C)COc1cccc(CN2CCC(n3cc(-c4ccccn4)nn3)C2)c1]

3-Azido-1-(3-isobutoxy-benzyl)-pyrrolidine (Intermediate 27, 0.4 g, 1.46 mmol) was taken in a mixture of solvents: t-butanol (4 mL) and water (1 mL). To this was added copper sulphate pentahydrate (0.01 g, 0.07 mmol), sodium ascorbate (0.03 g, 0.17 mmol), and 2-Ethynyl-pyridine (0.15 g, 1.46 mmol) and stirred at room temperature for 15 h. The reaction mixture was concentrated under reduced pressure and the titled compound was obtained by purification by column chromatography (pet ether/ethyl acetate 20%) to give the desired product (4%, 20 mg, colorless liquid). $^1$H NMR: (DMSO-$d_6$): δ 8.62 (s, 1H), 8.58-8.59 (m, 1H), 8.02 (d, J=7.92 Hz, 1H), 7.86-7.91 (m, 1H), 7.32-7.35 (m, 1H), 7.18-7.22 (m, 1H), 6.77-6.88 (m, 3H), 5.28 (s, 1H), 3.59-3.70 (m, 4H), 2.81-3.00 (m, 3H), 2.17-2.50 (m, 3H), 1.90-1.97 (m, 1H), 0.91 (d, J=6.72 Hz, 6H). LCMS: (Method B) 378.3 (M+1), Rt. 6.54 min, 90.3% (max), 85.0% (220 nm).

The following Examples were synthesized according to the procedure described for Example 4 from the starting materials listed in the table.

| Cmpd | Structure | Data | Starting Materials |
|---|---|---|---|
| 61 | 2-{1-[1-(3-Isobutoxy-benzyl)-pyrrolidin-3-yl]-1H-[1,2,3]triazol-4-yl}-6-methyl-pyridine | $^1$H NMR: (DMSO-d$_6$): δ 8.56 (s, 1H), 7.74-7.83 (m, 2H), 7.18-7.22 (m, 2H), 6.77-6.88 (m, 3H), 5.28 (d, J = 6.28 Hz, 2H), 3.63-3.70 (m, 4H), 2.84-2.98 (m, 3H), 1.91-2.17 (m, 2H), 0.91 (d, J = 6.68 Hz, 6H). LCMS: 392.2 (M + 1), Rt. 3.11 min, 95.3% (max), 94.2% (220 nm). | Intermediate 27 and 6-methyl-2-ethynyl-pyridine |
| 62 | 2-{1-[1-(3-Isobutoxy-benzyl)-pyrrolidin-3-yl]-1H-[1,2,3]triazol-4-yl}-6-methoxy-pyridine | $^1$H NMR: (DMSO-d$_6$): δ 8.57 (s, 1H), 7.76-7.80 (m, 1H), 7.60 (d, J = 7.36 Hz, 1H), 7.19 (t, J = 8.04 Hz, 1H), 6.88-6.90 (m, 2H), 6.75-6.80 (m, 2H), 5.28 (d, J = 2.52 Hz, 1H), 3.93 (s, 3H), 3.58-3.71 (m, 4H), 2.81-2.99 (m, 3H), 2.14-2.18 (m, 1H), 1.90-1.95 (m, 1H), 0.91 (d, J = 6.68 Hz, 6H). | Intermediate 27 and 6-methoxy-2-ethynyl-pyridine |
| 63 | 2-Bromo-6-{1-[1-(3-isobutoxy-benzyl)-pyrrolidin-3-yl]-1H-[1,2,3]triazol-4-yl}-pyridine | $^1$H NMR: (DMSO-d$_6$): δ 8.66 (s, 1H), 8.04 (d, J = 7.56 Hz, 1H), 7.84 (t, J = 7.80 Hz, 1H), 7.59 (d, J = 7.80 Hz, 1H), 7.20 (t, J = 8.00 Hz, 1H), 6.86-6.87 (m, 2H), 6.76-6.79 (m, 1H), 5.28 (d, J = 6.32 Hz, 1H), 3.59-3.70 (m, 4H), 2.84-2.99 (m, 3H), 1.92-2.21 (m, 2H), 0.90 (d, J = 6.68 Hz, 6H). | Intermediate 27 and 6-bromo-2-ethynyl-pyridine |

Example 5

{5-[1-(3-Isobutoxy-benzyl)-pyrrolidin-3-yl]-[1,3,4]oxadiazol-2-yl}-methanol (64)

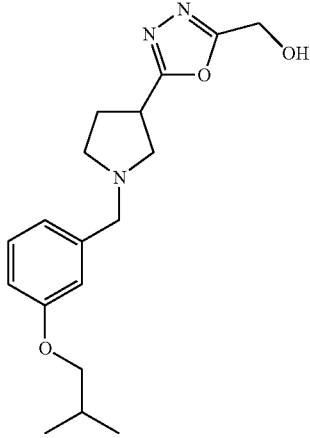 [SMILES: CC(C)COc1cccc(CN2CCC(c3nnc(CO)o3)C2)c1]

Acetic acid 5-[1-(3-isobutoxy-benzyl)-pyrrolidin-3-yl]-[1,3,4]oxadiazol-2-ylmethyl ester (Intermediate 31, 0.1 g, 0.27 mmol) was taken in methanol (3 mL) and water (1 mL) and to this was added potassium carbonate (0.05 g, 0.40 mmol) and stirred for 2 h at room temperature. The reaction mixture was concentrated under reduced pressure and the resulting crude mass was diluted with ethyl acetate, washed with water, brine, dried over sodium sulfate, and concentrated under reduced pressure to provide the crude product. Purification by column chromatography (pet ether/ethyl acetate 35%) provided the titled compound as a colorless oil (45%, 40 mg). $^1$H NMR: (DMSO-$d_6$): δ 7.17-7.21 (m, 1H), 6.84-6.86 (m, 2H), 6.77-6.80 (m, 1H), 5.83 (t, J=6.20 Hz, 1H), 4.58 (d, J=6.20 Hz, 2H), 3.53-3.70 (m, 5H), 2.86-2.90 (m, 1H), 2.69-2.73 (m, 1H), 2.58-2.62 (m, 2H), 2.21-2.25 (m, 1H), 1.95-2.08 (m, 2H), 0.96 (d, J=6.72 Hz, 6H). LCMS: 332.3 (M+1), Rt. 3.04 min, 93.9% (max), 93.9% (220 nm).

Example 6

The following compounds were synthesized according to one of the general procedure below from the starting materials listed in the table below.

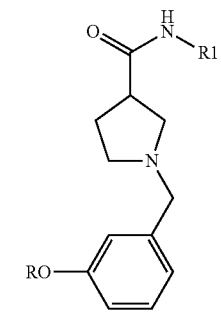

R = Ph or CH2CF3

To a 10 ml microwave vial with stir bar was added amine (0.270 g, 1.5 equiv) and DABAL-Me3 (0.540 mg, 1.2 equiv). Reagents were suspended in THF (4 ml) and run in microwave reactor at 130° C. for 20 min. The reaction mixture was cooled to room temperature and to it was added the appropriate Intermediate (0.500 g. 1 equiv). The reaction mixture was irradiated in microwave reactor at 130° C. for 20 min. After allowing to cool down to room temperature the reaction mixture was quenched by the addition of 2M HCl. The reaction mixture was extracted with ethyl acetate. The combined organic layer was washed with water (20 ml) and brine solution then dried over anhydrous sodium sulfate and evaporated under reduced pressure. The crude residue was purified by column chromatography using petroleum ether-ethyl acetate as eluents to get the pure amide.

A solution of amine (1 equiv) in 10 mL of dichloromethane was mixed with Intermediate 34 or 35 (1.2 equiv) and $Et_3N$ (3 equiv). T3P (3 equiv) was added to the reaction mixture at 0 OC. The reaction mixture was stirred at room temperature for 12 h. The reaction mixture was diluted with dichloromethane (20 mL) and washed with 10% NaHCO3 solution (1×20 mL), water (1×20 mL), followed by brine solution (lx 20 mL), then dried over anhydrous sodium sulphate, filtered and evaporated. The residue was purified by column chromatography on silica gel to get the amide product.

| Cmpd | Structure | Data | Starting Materials |
|---|---|---|---|
| 65 | 1-(3-Phenoxy-benzyl)-pyrrolidine-3-carboxylic acid 2-methoxy-benzylamide | $^1$H NMR (400 MHz, DMSO-$d_6$): δ 7.37-7.26 (m, 5H), 7.24-7.22 (m, 1H), 7.15-7.12 (m, 1H), 7.07 (br s, 1H), 7.02-7.00 (m, 2H), 6.97-6.88 (m, 3H), 6.75 (br s, 1H), 4.40 (d, J = 5.76 Hz, 2H), 3.97 (br s, 2H), 3.82 (br s, 3H), 3.09-2.96 (m, 5H), 2.37 (br s, 1H), 2.11 (br s, 1H). LCMS: 417.3 (m + 1), RT(4.12) min, 95.30% (Max), 95.28% (220 nm). | Intermediate 32 and 2-methoxybenzyl amine |

| Cmpd | Structure | Data | Starting Materials |
|---|---|---|---|
| 66 | 1-(3-Phenoxy-benzyl)-pyrrolidine-3-carboxylic acid 4-methoxy-benzylamide | ¹H NMR (400 MHz, DMSO-d₆): δ 8.22 (br s, 1H), 7.40-7.35 (m, 2H), 7.31 (t, J = 7.84 Hz, 1H), 7.14-7.11 (m, 3H), 7.07-7.05 (m, 1H), 7.00-6.98 (m, 2H), 6.94 (br s, 1H), 6.87-6.83 (m, 3H), 4.16 (d, J = 5.84 Hz, 2H), 3.71 (s, 3H), 3.54 (brs, 2H), 2.87-2.76 (m, 2H), 2.67-2.60 (m, 1H), 2.39 (br s, 2H), 1.91-1.87 (m, 2H). | Intermediate 32 and 4-methoxybenzylamine |
| 67 | 1-(3-Phenoxy-benzyl)-pyrrolidine-3-carboxylic acid 4-trifluoromethoxy-benzylamide | ¹H NMR (400 MHz, DMSO-d₆): δ 10.75-10.30 (m, 1H), 8.77 (s, 1H), 7.45-7.30 (m, 8H), 7.16 (t, J = 7.40 Hz, 1H), 7.05-7.03 (m, 3H), 4.38-4.29 (m, 3H), 3.60-3.49 (m, 1H), 3.18 (br s, 2H), 2.46-2.38 (m, 3H), 2.17 (br s, 1H), 2.11-1.89 (m, 1H). | Intermediate 32 and 4-trifluoromethoxy benzylamine |
| 68 | 1-(3-Phenoxy-benzyl)-pyrrolidine-3-carboxylic acid 4-chloro-benzylamide | ¹H NMR (400 MHz, DMSO-d₆): δ 10.92 (brs, 1H), 8.71 (brs, 1H), 7.47-7.36 (m, 5H), 7.26-7.24 (m, 3H), 7.17-7.13 (m, 1H), 7.03-7.02 (m, 3H), 4.64-4.24 (m, 3H), 3.61-3.49 (m, 2H), 3.14-2.98 (m, 2H), 2.29-1.92 (m, 4H). LCMS: 421.0 (m + 1), RT(4.47) min, 98.13% (Max), 98.22%(220 nm). | Intermediate 32 and 4-chlorobenzyl-amine |

| Cmpd | Structure | Data | Starting Materials |
|---|---|---|---|
| 69 | 1-(3-Phenoxy-benzyl)-pyrrolidine-3-carboxylic acid 3-chloro-benzylamide | $^1$H NMR (400 MHz, CD$_3$OD): δ 7.45-7.36 (m, 3H), 7.33-7.25 (m, 3H), 7.22-7.20 (m, 2H), 7.18-7.14 (m, 2H), 7.05-7.00 (m, 3H), 4.36 (s, 2H), 4.23-4.14 (m, 2H), 3.35-3.31 (m, 2H), 3.23-3.20 (m, 3H), 2.37-2.31 (m, 1H), 2.19-2.13 (m, 1H). | Intermediate 32 and 3-chlorobenzyl-amine |
| 70 | 1-(3-Phenoxy-benzyl)-pyrrolidine-3-carboxylic acid 3-trifluoromethyl-benzylamide | $^1$H NMR (400 MHz, CD$_3$OD): δ 7.58-7.52 (m, 4H), 7.39-7.34 (m, 3H), 7.16-7.11 (m, 2H), 7.07 (br s, 1H), 7.01-6.96 (m, 3H), 4.47-4.40 (m, 2H), 3.94-3.91 (m, 2H), 3.14-3.12 (m, 2H), 2.99-2.79 (m, 3H), 2.22-2.20 (m, 1H), 2.12-2.08 (m, 1H). | Intermediate 32 and 3-trifluoromethyl benzylamine |
| 71 | 1-(3-Phenoxy-benzyl)-pyrrolidine-3-carboxylic acid 4-trifluoromethyl-benzylamide | $^1$H NMR (400 MHz, CD$_3$OD): δ 7.62 (d, J = 8.12 Hz, 2H), 7.44 (d, J = 8.08 Hz, 2H), 7.37-7.29 (m, 3H), 7.13-7.09 (m, 2H), 7.02-6.96 (m, 3H), 6.92-6.89 (m, 1H), 4.43 (s, 2H), 3.72-3.63 (m, 2H), 3.02-2.92 (m, 2H), 2.81-2.76 (m, 1H), 2.69-2.59 (m, 2H), 2.13-2.09 (m, 2H). | Intermediate 32 and 4-trifluoromethyl benzylamine |

| Cmpd | Structure | Data | Starting Materials |
|---|---|---|---|
| 72 | 1-(3-Phenoxy-benzyl)-pyrrolidine-3-carboxylic acid 2-trifluoromethyl-benzylamide | ¹H NMR (400 MHz, CD₃OD): δ 7.71 (d, J = 7.80 Hz, 1H), 7.61 (t, J = 7.40 Hz, 1H), 7.52 (d, J = 7.76 Hz, 1H), 7.48-7.36 (m, 4H), 7.23 (d, J = 7.64 Hz, 1H), 7.18-7.13 (m, 2H), 7.06-7.01 (m, 3H), 4.62-4.54 (m, 2H), 4.27-4.18 (m, 2H), 3.38-3.36 (m, 2H), 3.31-3.24 (m, 3H), 2.42-2.32 (m, 1H), 2.23-2.14 (m, 1H). LCMS: 455.3 (m + 1), RT(4.45) min, 96.28% (Max), 96.25%(220 nm). | Intermediate 32 and 2-trifluoromethyl benzylanine |
| 73 | 1-(3-Phenoxy-benzyl)-pyrrolidine-3-carboxylic acid 2-fluoro-benzylamide | ¹H NMR (400 MHz, CD₃OD): δ 7.71 (d, J = 7.80 Hz, 1H), 7.61 (t, J = 7.40 Hz, 1H), 7.52 (d, J = 7.76 Hz, 1H), 7.48-7.36 (m, 4H), 7.23 (d, J = 7.64 Hz, 1H), 7.18-7.13 (m, 2H), 7.06-7.01 (m, 3H), 4.62-4.54 (m, 2H), 4.27-4.18 (m, 2H), 3.38-3.36 (m, 2H), 3.31-3.24 (m, 3H), 2.42-2.32 (m, 1H), 2.23-2.14 (m, 1H). | Intermediate 32 and 2-fluorobenzyl-amine |
| 74 | 1-(3-Phenoxy-benzyl)-pyrrolidine-3-carboxylic acid 3-fluoro-benzylamide | ¹H NMR (400 MHz, CD₃OD): δ 7.38-7.30 (m, 4H), 7.15-7.13 (m, 2H), 7.11-7.06 (m, 2H), 7.02-6.97 (m, 5H), 4.36 (s, 2H), 3.92-3.83 (m, 2H), 3.12-3.07 (m, 2H), 2.99-2.93 (m, 2H), 2.92-2.84 (m, 1H), 2.23-2.18 (m, 1H), 2.12-2.11 (m, 1H). | Intermediate 32 and 3-fluorobenzyl-amine |

| Cmpd | Structure | Data | Starting Materials |
|---|---|---|---|
| 75 | 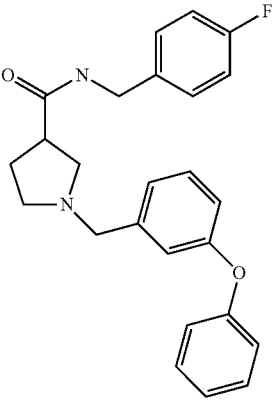 [SMILES: O=C(NCc1ccc(F)cc1)C1CCN(Cc2cccc(Oc3ccccc3)c2)C1]<br>1-(3-Phenoxy-benzyl)-pyrrolidine-3-carboxylic acid 4-fluoro-benzylamide | $^1$H NMR (400 MHz, CD$_3$OD): δ 7.36-7.25 (m, 5H), 7.13-6.96 (m, 7H), 6.91-6.88 (m, 1H), 4.91 (s, 2H), 3.67-3.59 (m, 2H), 2.99-2.95 (m, 1H), 2.93-2.87 (m, 1H), 2.78-2.72 (m, 1H), 2.62-2.54 (m, 2H), 2.11-2.09 (m, 2H). LCMS: 405.3 (m + 1), RT(4.18) min, 99.46% (Max), 99.46%(220 nm). | Intermediate 32 and 4-fluorobenzylamine |
| 76 | 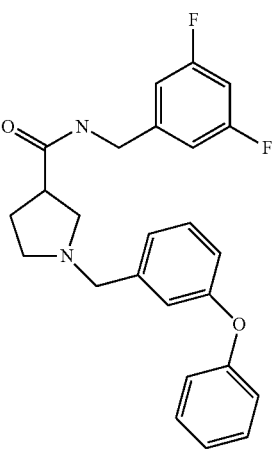 [SMILES: O=C(NCc1cc(F)cc(F)c1)C1CCN(Cc2cccc(Oc3ccccc3)c2)C1]<br>1-(3-Phenoxy-benzyl)-pyrrolidine-3-carboxylic acid 3,5-difluoro-benzylamide | $^1$H NMR (400 MHz, CD$_3$OD): δ 7.37-7.29 (m, 3H), 7.13-7.09 (m, 2H), 7.01-6.96 (m, 3H), 6.91-6.80 (m, 4H), 4.35 (s, 2H), 3.69-3.60 (m, 2H), 3.02-2.90 (m, 2H), 2.79-2.73 (m, 1H), 2.64-2.55 (m, 2H), 2.13-2.02 (m, 2H). | Intermediate 32 and 3,5-difluorobenzylamine |
| 77 | 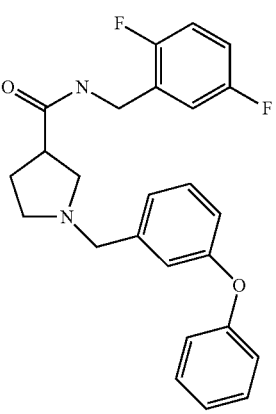 [SMILES: O=C(NCc1cc(F)ccc1F)C1CCN(Cc2cccc(Oc3ccccc3)c2)C1]<br>1-(3-Phenoxy-benzyl)-pyrrolidine-3-carboxylic acid 2,5-difluoro-benzylamide | $^1$H NMR (400 MHz, DMSO-d$_6$): δ 8.18 (t, J = 5.00 Hz, 1H), 7.41-7.35 (m, 3H), 7.33-7.28 (m, 1H), 7.14-7.11 (m, 1H), 7.10-7.04 (m, 3H), 7.00-6.98 (m, 2H), 6.93 (s, 1H), 6.87-6.85 (m, 1H), 4.28 (d, J = 5.24 Hz, 2H), 3.54 (s, 2H), 2.82-2.76 (m, 2H), 2.61-2.60 (m, 1H), 2.37-2.32 (m, 2H), 1.87-1.84 (m, 2H). | Intermediate 32 and 2,5-difluorobenzylamine |

| Cmpd | Structure | Data | Starting Materials |
|---|---|---|---|
| 78 | 1-(3-Phenoxy-benzyl)-pyrrolidine-3-carboxylic acid 2,4-difluoro-benzylamide | $^1$H NMR (400 MHz, CD$_3$OD): δ 7.42-7.33 (m, 4H), 7.20-7.10 (m, 3H), 7.03-7.00 (m, 3H), 6.98-6.90 (m, 2H), 4.42-4.34 (m, 2H), 4.17-4.03 (m, 2H), 3.24-3.07 (m, 5H), 2.32-2.23 (m, 1H), 2.15-2.07 (m, 1H). LCMS: 423.0 (m + 1), RT(4.15) min, 98.85% (Max), 98.70%(220 nm). | Intermediate 32 and 2,4-difluorobenzylamine |
| 79 | 1-(3-Phenoxy-benzyl)-pyrrolidine-3-carboxylic acid 2,6-difluoro-benzylamide | $^1$H NMR (400 MHz, CD$_3$OD): δ 7.43-7.32 (m, 4H), 7.20-7.11 (m, 3H), 7.03-6.96 (m, 5H), 4.51-4.43 (m, 2H), 4.15-4.07 (m, 2H), 3.25-3.12 (m, 5H), 2.28-2.23 (m, 1H), 2.13-2.06 (m, 1H). | Intermediate 32 and 2,6-difluorobenzylamine |
| 80 | 1-(3-Phenoxy-benzyl)-pyrrolidine-3-carboxylic acid 3,4-difluoro-benzylamide | $^1$H NMR (400 MHz, CD$_3$OD): δ 7.36-7.29 (m, 3H), 7.23-7.04 (m, 5H), 7.00-6.96 (m, 3H), 6.91-6.88 (m, 1H), 4.31 (s, 2H), 3.68-3.60 (m, 2H), 3.31-2.88 (m, 2H), 2.78-2.73 (m, 1H), 2.63-2.55 (m, 2H), 2.12-1.99 (m, 2H). | Intermediate 32 and 3,4-difluorobenzylamine |

| Cmpd | Structure | Data | Starting Materials |
|---|---|---|---|
| 81 | 1-(3-Phenoxy-benzyl)-pyrrolidine-3-carboxylic acid 4-tert-butyl-benzylamide | ¹H NMR (400 MHz, CD₃OD): δ 7.36-7.28 (m, 5H), 7.19-7.17 (m, 2H), 7.12-7.07 (m, 2H), 6.99-6.96 (m, 3H), 6.90-6.88 (m, 1H), 4.30 (s, 2H), 3.67-3.58 (m, 2H), 2.98-2.87 (m, 2H), 2.75-2.71 (m, 1H), 2.63-2.54 (m, 2H), 2.08-2.02 (m, 2H), 1.30 (s, 9H). | Intermediate 32 and 4-tert-butylbenzyl-amine |
| 82 | 1-(3-Phenoxy-benzyl)-pyrrolidine-3-carboxylic acid 3-methyl-benzylamide | ¹H NMR (400 MHz, DMSO-d₆): δ 8.26 (t, J = 5.04 Hz, 1H), 7.40-7.36 (m, 2H), 7.33-7.29 (m, 1H), 7.19-7.11 (m, 2H), 7.07-6.98 (m, 6H), 6.94 (s, 1H), 6.88-6.86 (m, 1H), 4.19 (d, J = 5.88 Hz, 2H), 3.55 (s, 2H), 2.89-2.85 (m, 1H), 2.80-2.76 (m, 1H), 2.66-2.56 (m, 1H), 2.47-2.32 (m, 2H), 2.26 (s, 3H), 1.92-1.89 (m, 2H). | Intermediate 34 and 3-methylbenzyl-amine |
| 83 | 1-(3-Phenoxy-benzyl)-pyrrolidine-3-carboxylic acid 4-methyl-benzylamide | ¹H NMR (400 MHz, CD₃OD): δ 7.36-7.28 (m, 3H), 7.13-7.07 (m, 6H), 6.99-6.97 (m, 3H), 6.91-6.89 (m, 1H), 4.29 (s, 2H), 3.68-3.59 (m, 2H), 2.98-2.87 (m, 2H), 2.78-2.72 (m, 1H), 2.63-2.54 (m, 2H), 2.31 (s, 3H), 2.10-2.02 (m, 2H). LCMS: 401.3(m + 1), RT(4.25) min, 94.65% (Max), 94.48%(220 nm). | Intermediate 34 and 4-methylbenzyl-amine |

| Cmpd | Structure | Data | Starting Materials |
|---|---|---|---|
| 84 | 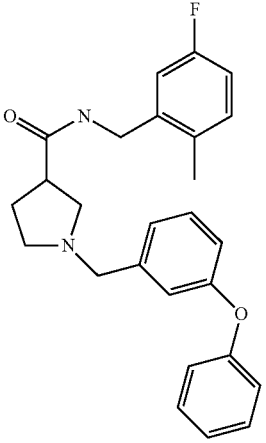 [SMILES: Cc1ccc(F)cc1CNC(=O)C1CCN(Cc2cccc(Oc3ccccc3)c2)C1]<br>1-(3-Phenoxy-benzyl)-pyrrolidine-3-carboxylic acid 5-fluoro-2-methyl-benzylamide | $^1$H NMR (400 MHz, CD$_3$OD): δ 7.36-7.29 (m, 3H), 7.17-7.08 (m, 3H), 7.01-6.85 (m, 6H), 4.32 (s, 2H), 3.75-3.67 (m, 2H), 3.06-2.95 (m, 2H), 2.84-2.79 (m, 1H), 2.74-2.63 (m, 2H), 2.26 (s, 3H), 2.16-2.14 (m, 2H). | Intermediate 32 and 5-fluoro-2-methylbenzyl-amine |
| 85 | 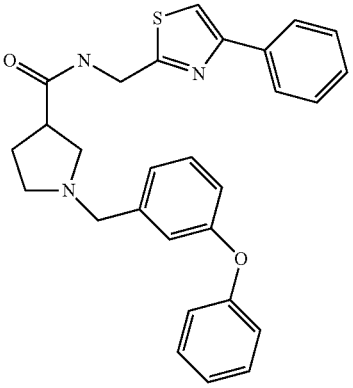 [SMILES: O=C(NCc1nc(-c2ccccc2)cs1)C1CCN(Cc2cccc(Oc3ccccc3)c2)C1]<br>1-(3-Phenoxy-benzyl)-pyrrolidine-3-carboxylic acid (4-phenyl-thiaz-1-2-ylmethyl)-amide | $^1$H NMR (400 MHz, CD$_3$OD): δ 7.90-7.88 (m, 2H), 7.69 (s, 1H), 7.43-7.39 (m, 2H), 7.35-7.28 (m, 4H), 7.11-7.08 (m, 2H), 7.02 (s, 1H), 6.98-6.96 (m, 2H), 6.90-6.88 (m, 1H), 4.70 (d, J = 1.44 Hz, 2H), 3.70-3.61 (m, 2H), 3.06-3.02 (m, 1H), 2.95-2.90 (m, 1H), 2.78-2.70 (m, 1H), 2.68-2.58 (m, 2H), 2.15-2.10 (m, 2H). LCMS: 470.0(m + 1), RT(4.42) min, 99.19% (Max), 98.81% (254 nm). | Intermediate 34 and 4-phenyl-2-thiazolylmethyl amine |
| 86 | 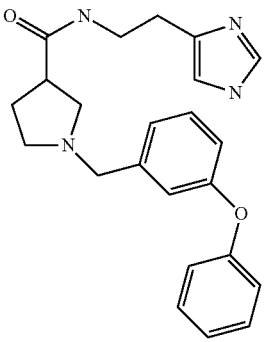 [SMILES: O=C(NCCc1c[nH]cn1)C1CCN(Cc2cccc(Oc3ccccc3)c2)C1]<br>1-(3-Phenoxy-benzyl)-pyrrolidine-3-carboxylic acid [2-(1H-imidazol-4-yl)-ethyl]-amide | $^1$H NMR (400 MHz, CD$_3$OD): δ 7.59 (s, 1H), 7.37-7.31 (m, 3H), 7.13-7.08 (m, 2H), 7.01-6.97 (m, 3H), 6.93-6.90 (m, 1H), 6.82 (s, 1H), 3.68-3.68 (m, 2H), 3.43-3.35 (m, 2H), 2.93-2.87 (m, 2H), 2.80-2.74 (m, 3H), 2.64-2.58 (m, 2H), 2.09-2.01 (m, 1H), 2.00-1.98 (m, 1H). | Intermediate 34 and 2-(1H-imidazol-4-yl)-ethylamine |

| Cmpd | Structure | Data | Starting Materials |
|---|---|---|---|
| 87 | 1-(3-Phenoxy-benzyl)-pyrrolidine-3-carboxylic acid (tetrahydro-furan-2-ylmethyl)-amide | ¹H NMR (400 MHz, DMSO-d₆): δ 7.85-7.84 (m, 1H), 7.40-7.35 (m, 2H), 7.33-7.29 (m, 1H), 7.14-7.10 (m, 1H), 7.07-7.05 (m, 1H), 7.00-6.98 (m, 2H), 6.94 (s, 1H), 6.87-6.85 (m, 1H), 3.77-3.70 (m, 2H), 3.58-3.53 (m, 3H), 3.10-3.06 (m, 2H), 2.82-2.80 (m, 1H), 2.74-2.69 (m, 1H), 2.59-2.57 (m, 1H), 2.37-2.33 (m, 2H), 1.88-1.73 (m, 5H), 1.43-1.41 (m, 1H). | Intermediate 34 and tetrahydronfuran-2ylmethyl amine |
| 88 | 1-(3-Phenoxy-benzyl)-pyrrolidine-3-carboxylic acid (thiophen-2-ylmethyl)-amide | ¹H NMR (400 MHz, DMSO-d₆): δ 8.42 (s, 1H), 7.40-7.29 (m, 4H), 7.15-7.11 (m, 1H), 7.08-7.06 (m, 1H), 7.00-6.98 (m, 2H), 6.95-6.92 (m, 3H), 6.88-6.86 (m, 1H), 4.39 (d, J = 5.80 Hz, 2H), 3.57 (s, 2H), 2.82-2.76 (m, 2H), 2.63 (brs, 1H), 2.32 (brs, 2H), 1.89 (d, J = 7.08 Hz, 2H). | Intermediate 34 and thiophene2-ylmethyl amine |
| 89 | 1-[3-(2,2,2-Trifluoro-ethoxy)-benzyl]-pyrrolidine-3-carboxylic acid (5-methyl-pyrazin-2-ylmethyl)-amide | ¹H NMR (400 MHz, CD₃OD): δ 8.46-8.42 (m, 2H), 7.26-7.28 (m, 1H), 7.04-7.02 (m, 2H), 6.94-6.91 (m, 1H), 4.56-4.48 (m, 4H), 3.66 (d, J = 2.04 Hz, 2H), 3.05-3.01 (m, 1H), 2.92-2.88 (m, 1H), 2.76-2.72 (m, 1H), 2.67-2.61 (m, 2H), 2.54 (s, 3H), 2.14-2.09 (m, 2H). LCMS: 409.3(m + 1), RT(3.01) min, 98.34% (Max), 97.45% (254 nm). | Intermediate 33 and 5-methyl-pyrazin-2-ylmethyl amine |

-continued

| Cmpd | Structure | Data | Starting Materials |
|---|---|---|---|
| 90 | 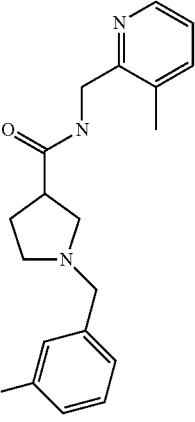<br>1-[3-(2,2,2-Trifluoro-ethoxy)-benzyl]-pyrrolidine-3-carboxylic acid (3-methyl-pyridin-2-ylmethyl)-amide | $^1$H NMR (400 MHz, CD$_3$OD): δ 8.34 (dd, J = 4.88, 1.00 Hz, 1H), 7.63-7.61 (m, 1H), 7.29-7.23 (m, 2H), 7.06-7.02 (m, 2H), 6.93-6.91 (m, 1H), 4.54-4.48 (m, 4H), 3.67 (s, 2H), 3.06-3.00 (m, 1H), 2.90-2.85 (m, 1H), 2.72-2.65 (m, 3H), 2.34 (s, 3H), 2.18-2.06 (m, 2H). | Intermediate 35 and 3-methyl-pyridin-2-ylmethyl amine |
| 91 | 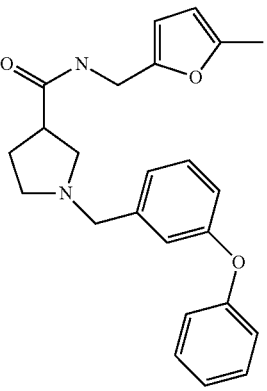 [SMILES: Cc1ccc(CNC(=O)C2CCN(Cc3cccc(Oc4ccccc4)c3)C2)o1]<br>1-(3-Phenoxy-benzyl)-pyrrolidine-3-carboxylic acid (5-methyl-furan-2-ylmethyl)-amide | $^1$H NMR (400 MHz, CD$_3$OD): δ 7.35-7.29 (m, 3H), 7.13-7.08 (m, 2H), 7.01-6.97 (m, 3H), 6.91-6.89 (m, 1H), 6.07 (d, J = 2.96 Hz, 1H), 5.91 (dd, J = 2.94, 0.92 Hz, 1H), 4.27 (s, 2H), 3.69-3.61 (m, 2H), 2.97-2.88 (m, 2H), 2.79-2.73 (m, 1H), 2.63-2.56 (m, 2H), 2.23 (s, 3H), 2.10-2.04 (m, 2H). | Intermediate 34 and 5-methyl-furan-2-ylmethyl amine |
| 92 | 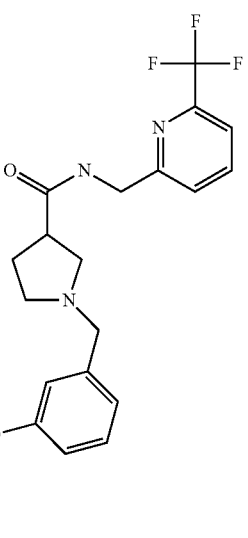<br>1-[3-(2,2,2-Trifluoro-ethoxy)-benzyl]-pyrrolidine-3-carboxylic acid (6-trifluoromethyl-pyridin-2-ylmethyl)-amide | $^1$H NMR (400 MHz, CD$_3$OD): δ 8.00-7.96 (m, 1H), 7.69-7.67 (m, 1H), 7.55-7.53 (m, 1H), 7.30-7.26 (m, 1H), 7.04-7.02 (m, 2H), 6.94-6.91 (m, 1H), 4.54-4.48 (m, 4H), 3.71-3.63 (m, 2H), 3.09-3.03 (m, 1H), 2.95-2.91 (m, 1H), 2.79-2.71 (m, 1H), 2.69-2.60 (m, 2H), 2.16-2.08 (m, 2H). | Intermediate 35 and 6-trifluoromethyl-pyridin-2-ylmethyl amine |

| Cmpd | Structure | Data | Starting Materials |
|---|---|---|---|
| 93 | 3-hydroxy-1-(phenyloxy-benzyl)-pyrrolidine-3-carboxylic acid (pyridin-2-ylmethyl)-amide | NMR 400 MHz, DMSO-$d_6$: δ 8.47-8.49 (m, 1H), 8.41-8.42 (m, 1H), 7.71-7.76 (m, 2H), 7.35-7.39 (m, 2H), 7.29-7.33 (m, 1H), 7.08-7.25 (m, 1H), 6.85-7.00 (m, 6H), 5.74 (s, 1H), 4.37-4.38 (m, 2H), 3.59 (s, 2H), 2.75-2.82 (m, 2H), 2.62-2.65 (m, 1H), 2.43-2.47 (m, 1H), 2.20-2.25 (m, 1H), 1.18-1.80 (m, 1H). | Intermediate 45 and 2-pyridinylmethyl amine |
| 94 | 3-Hydroxy-2-oxo-1-(3-phenoxy-benzyl)-pyrrolidine-3-carboxylic acid (pyridin-2-ylmethyl)-amide | $^1$H NMR : 400 MHz, DMSO-$d_6$: δ 8.48-8.50 (m, 2H), 7.73-7.74 (m, 1H), 7.30-7.37 (m, 5H), 6.87-7.14 (m, 6H), 6.60 (s, 1H), 4.38-4.46 (m, 4H), 3.28-3.30 (m, 2H), 2.48-2.50 (m, 1H), 1.98-1.99 (m, 1H). LCMS: 418.2 (M + H), Rt. 3.4 min, 97.5% (max), 97.9% (254 nm). | Intermediate 56 and pyridine-2-ylmethyl amine |
| 95 | 3-Chloro-2-oxo-1-(3-phenoxy-benzyl)-pyrrolidine-3-carboxylic acid (pyridin-2-ylmethyl)-amide | $^1$H NMR: 400 MHz, DMSO-$d_6$: δ 8.95-9.08 (m, 1H), 8.50 (d, J = 4.20 Hz, 1H), 7.75-7.75 (m, 1H), 7.30-7.40 (m, 3H), 7.26 (d, J = 1.88 Hz, 1H), 6.89-7.15 (m, 7H), 4.36-4.58 (m, 4H), 3.35-3.38 (m, 2H), 2.81-2.89 (m, 1H), 2.48-2.50 (m, 1H). | Intermediate 57 and pyridine-2-ylmethyl amine |

| Cmpd | Structure | Data | Starting Materials |
|---|---|---|---|
| 96 | 1-(3-Phenoxy-benzyl)-pyrrolidine-3-carboxylic acid 4-difluoromethoxy-benzylamide | $^1$H NMR (400 MHz, CD$_3$OD): δ 8.53 (s, 1H), 7.44-7.39 (m, 3H), 7.37-7.31 (m, 2H), 7.22-7.10 (m, 5H), 7.07-7.02 (m, 3H), 6.99-6.62 (m, 1H), 4.40-4.33 (m, 2H), 4.17-4.08 (m, 2H), 3.30-3.22 (m, 1H), 3.20-3.12 (m, 4H), 2.34-2.25 (m, 1H), 2.19-2.10 (m, 1H). LCMS: 453.2 (m + 1), RT(4.38) min, 99.57% (Max), 99.40%(220nm). | Intermediate 34 and 4-difluoro methoxy-benzyl amine |
| 97 | 1-[3-(2,2,2-Trifluoro-ethoxy)-benzyl]-pyrrolidine-3-carboxylic acid (5-methyl-pyridin-2-ylmethyl)-amide | $^1$H NMR (400 MHz, CD$_3$OD): δ 8.31-8.31 (m, 1H), 7.64-7.61 (m, 1H), 7.30-7.26 (m, 1H), 7.24-7.22 (m, 1H), 7.04-7.02 (m, 2H), 6.94-6.91 (m, 1H), 4.55-4.50 (m, 2H), 4.48-4.43 (m, 2H), 3.66-3.62 (m, 2H), 3.06-3.02 (m, 1H), 2.93-2.88 (m, 1H), 2.76-2.72 (m, 1H), 2.68-2.58 (m, 2H), 2.34 (s, 3H), 2.14-2.03 (m, 2H). | Intermediate 35 and 5-methyl-pyridin-2-ylmethyl amine |
| 98 | 1-[3-(2,2,2-Trifluoro-ethoxy)-benzyl]-pyrrolidine-3-carboxylic acid (3-fluoro-pyridin-2-ylmethyl)-amide | $^1$H NMR (400 MHz, CD$_3$OD): δ 8.35 (s, 1H), 7.61-7.59 (m, 1H), 7.49-7.45 (m, 1H), 7.40 (s, 1H), 7.21-7.16 (m, 3H), 4.64-4.57 (m, 4H), 4.46-4.32 (m, 2H), 3.69-3.54 (m, 3H), 3.32-3.31 (m, 2H), 2.54-2.20 (m, 2H). LCMS: 412.3(m + 1), RT(3.19) min, 97.96% (Max), 98.12% (220 nm). | Intermediate 35 and 3-fluoro-pyridin-2-ylmethyl amine |

| Cmpd | Structure | Data | Starting Materials |
|---|---|---|---|
| 99 | 3-Methyl-1-(2-phenyl-oxazol-4-ylmethyl)-pyrrolidine-3-carboxylic acid (pyridin-2-ylmethyl)-amide | $^1$H NMR (CDCl$_3$) δ: 8.57-8.30 (m, 2H), 8.03-7.82 (m, 2H), 7.68 (s, 1H), 7.47 (td, J = 7.5, 1.8 Hz, 1H), 7.41-7.29 (m, 3H), 7.16-7.07 (m, 1H), 7.07-6.96 (m, 1H), 4.72-4.35 (m, 2H), 3.82-3.43 (m, 2H), 3.28-3.00 (m, 2H), 2.49 (s, 1H), 2.28-2.01 (m, 1H), 1.80-1.58 (m, 1H), 1.26 (s, 3H). | Intermediate 61 and 2-pyridylbenzylamine |
| 100 | 4-(3-Phenoxy-benzyl)-morpholine-2-carboxylic acid ethylamide | $^1$H NMR (CDCl$_3$) δ: 7.35-7.12 (m, 3H), 7.10-6.88 (m, 5H), 6.87-6.73 (m, 1H), 6.45 (t, J = 5.5 Hz, 1H), 3.95 (dd, J = 7.8, 2.7 Hz, 1H), 3.87-3.77 (m, 1H), 3.61 (td, J = 11.4, 2.7 Hz, 1H), 3.43 (dd, J = 13.2, 7.8 Hz, 2H), 3.31-3.12 (m, 3H), 2.70-2.48 (m, 1H), 2.07 (td, J = 11.4, 3.3 Hz, 1H), 1.91 (t, J = 11.1 Hz, 1H), 1.08 (t, J = 7.3 Hz, 3H) | Intermediate 63 and ethylamine |
| 101 | 3-Methyl-1-(3-phenoxy-benzyl)-pyrrolidine-3-carboxylic acid (1-methyl-1H-imidazol-2-ylmethyl)-amide | $^1$H NMR (300 MHz, DMSO-d$_6$) d: 8.27-8.08 (t, J = 5.2 Hz, 1H), 7.43-7.26 (m, 3H), 7.17-6.95 (m, 6H), 6.90-6.82 (ddd, J = 8.1, 2.5, 1.0 Hz, 1H), 6.80-6.71 (d, J = 1.2 Hz, 1H), 4.39-4.18 (m, 2H), 3.67-3.43 (m, 5H), 2.91-2.75 (d, J = 9.3 Hz, 1H), 2.65-2.53 (td, J = 8.7, 5.2 Hz, 1H), 2.49-2.37 (m, 1H), 2.30-2.13 (m, 2H), 1.64-1.46 (ddd, J = 13.2, 8.4, 5.4 Hz, 1H), 1.23-1.14 (s, 3H). | Intermediate 40 and C-(1-Methyl-1H-imidazol-2-yl)-methylamine |

| Cmpd | Structure | Data | Starting Materials |
|---|---|---|---|
| 102 | 3-Methyl-1-(2-phenyl-thiazol-5-ylmethyl)-pyrrolidine-3-carboxylic acid (pyridin-2-ylmethyl)-amide | $^1$H NMR (300 MHz, DMSO-$d_6$) δ: 8.48 (ddd, J = 4.8, 1.8, 1.0 Hz, 1H), 8.28 (t, J = 5.8 Hz, 1H), 7.94-7.80 (m, 2H), 7.79-7.66 (m, 2H), 7.54-7.40 (m, 3H), 7.29-7.15 (m, 2H), 4.36 (dd, J = 5.9, 2.3 Hz, 2H), 3.86 (t, J = 1.3 Hz, 2H), 2.99 (d, J = 9.2 Hz, 1H), 2.67 (dtd, J = 23.7, 8.6, 5.7 Hz, 2H), 2.43-2.23 (m, 2H), 1.60 (ddd, J = 13.2, 8.2, 5.5 Hz, 1H), 1.28 (s, 3H). | Intermediate 64 and 2-pyridylbenzyl-amine |
| 103 | 3-Methyl-1-(3-phenoxy-benzyl)-pyrrolidine-3-carboxylic acid (1-pyridin-3-yl-propyl)-amide | $^1$H NMR (300 MHz, DMSO-$d_6$) d: 8.49-8.38 (m, 1H), 8.05 (d, J = 7.9 Hz, 1H), 7.68-7.53 (m, 1H), 7.43-7.26 (m, 3H), 7.17-7.03 (m, 2H), 7.03-6.93 (dt, J = 7.5, 3.2 Hz, 3H), 6.88 (d, J = 8.1 Hz, 1H), 4.74-4.59 (m, 1H), 3.63-3.50 (m, 2H), 2.82 (dd, J = 9.1, 4.7 Hz, 1H), 2.70-2.56 (m, 1H), 2.34-2.11 (m, 2H), 1.67 (t, J = 7.3 Hz, 2H), 1.61-1.49 (m, 1H), 1.19 (d, J = 6.2 Hz, 3H), 0.81 (q, J = 7.0 Hz, 3H). | Intermediate 40 and 1-Pyridin-3-yl-propylamine |
| 104 | 1-Methyl-4-[1-(3-phenoxy-benzyl)-pyrrolidine-3-carbonyl]-piperazin-2-one | $^1$H NMR (CDCl$_3$) δ: 7.35-7.24 (m, 3), 7.11-6.98 (m, 5), 6.92-6.87 (m, 1), 4.28-4.22 (m, 1), 4.13-4.07 (m, 1), 3.88-3.68 (m, 2), 3.61 (s, 2), 3.39-3.10 (br m, 3), 2.99 (s, 3), 2.93-2.75 (m, 2), 2.63-2.44 (m, 2), 2.12-2.03 (m, 2) | Intermediate 40 and 1-Methyl-piperazin-2-one hydrochloride |

| Cmpd | Structure | Data | Starting Materials |
|---|---|---|---|
| 105 | 4-(3-Phenoxy-benzyl)-morpholine-2-carboxylic acid (pyridin-2-ylmethyl)-amide | ¹H NMR (300 MHz, CDCl₃) δ 8.55 (ddd, J = 4.9, 1.8, 1.0 Hz, 1H), 7.64 (td, J = 7.7, 1.8 Hz, 1H), 7.61-7.51 (m, 1H), 7.39-7.14 (m, 5H), 7.13-6.93 (m, 5H), 6.86 (ddd, J = 8.1, 2.5, 1.1 Hz, 1H), 4.69-4.41 (m, 2H), 4.10 (dd, J = 10.5, 2.7 Hz, 1H), 3.93 (ddd, J = 11.2, 3.3, 1.6 Hz, 1H), 3.69 (td, J = 11.3, 2.5 Hz, 1H), 3.59-3.38 (m, 2H), 3.23 (dt, J = 11.4, 2.3 Hz, 1H), 2.65 (dd, J = 11.6, 2.0 Hz, 1H), 2.16 (d, J = 3.3 Hz, 1H), 2.04 (dd, J = 11.4, 10.5 Hz, 1H). | Intermediate 63 and 2-pyridylbenzyl amine |
| 106 | Morpholin-4-yl-[4-(3-phenoxy-benzyl)-morpholin-2-yl]-methanone | ¹H NMR (300 MHz, CDCl₃) δ 7.41-7.22 (m, 3H), 7.16-6.96 (m, 5H), 6.89 (ddd, J = 8.2, 2.5, 1.1 Hz, 1H), 4.21 (dd, J = 10.1, 2.5 Hz, 1H), 3.92 (ddd, J = 11.2, 3.4, 1.5 Hz, 1H), 3.81-3.36 (m, 11H), 2.91 (dt, J = 11.9, 2.1 Hz, 1H), 2.69 (dq, J = 11.6, 2.0 Hz, 1H), 2.40 (dd, J = 11.9, 10.1 Hz, 1H), 2.26 (td, J = 11.5, 3.4 Hz, 1H). | Intermediate 63 and morpholine |
| 107 | 4-(3-Phenoxy-benzyl)-morpholine-2-carboxylic acid (2-methoxy-ethyl)-amide | ¹H NMR (300 MHz, CDCl₃) δ 7.42-7.22 (m, 3H), 7.16-6.97 (m, 5H), 6.93-6.82 (m, 2H), 4.05 (dd, J = 10.6, 2.7 Hz, 1H), 3.92 (ddd, J = 11.2, 3.3, 1.5 Hz, 1H), 3.69 (td, J = 11.3, 2.5 Hz, 1H), 3.59-3.34 (m, 9H), 3.22 (dt, J = 11.4, 2.3 Hz, 1H), 2.67 (dq, J = 11.7, 2.1 Hz, 1H), 2.16 (td, J = 11.5, 3.3 Hz, 1H), 2.05-1.92 (m, 1H). | Intermediate 63 and 2-meethoxyethyl amine |

| Cmpd | Structure | Data | Starting Materials |
|---|---|---|---|
| 108 | (1,3-Dihydro-pyrrolo[3,4-c]pyridin-2-yl)-[3-methyl-1-(3-phenoxy-benzyl)-pyrrolidin-3-yl]-methanone | LCMS: 414.5 (m + 1), RT(1.61) min, 91.5% (220nm). | Intermediate 40 and 2,3-Dihydro-1H-pyrrolo[3,4-c]pyridine |
| 109 | 1-(3-Trifluoromethoxy-benzyl)-pyrrolidine-3-carboxylic acid (pyridin-2-ylmethyl)-amide hydrochloride | $^1$H NMR (D$_2$O) δ 8.73 (d, J = 5.5 Hz, 1H), 8.57 (t, J = 7.8 Hz, 1H), 8.06-7.92 (m, 2H), 7.65 (t, J = 7.4 Hz, 1H), 7.55 (d, J = 11.6 Hz, 3H), 4.53 (s, 2H), 3.95-3.23 (m, 6H), 2.82-2.01 (m, 3H). LCMS: 380 (M + 1), Rt. 2.33 min. HPLC: 95.8% (254 nm), Rt. 2.46 min. | Intermediate 35 and 2-pyridyl benzylamine |

Example 7

3-Methyl-2-oxo-1-(3-phenoxy-benzyl)-piperidine-3-carboxylic acid (pyridin-2-ylmethyl)-amide (110)

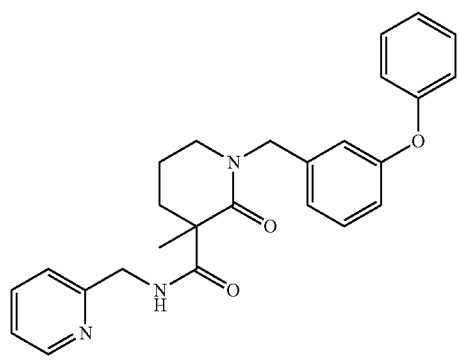 [SMILES: CC1(C(=O)NCc2ccccn2)CCCN(Cc2cccc(Oc3ccccc3)c2)C1=O]

3-Methyl-2-oxo-1-(3-phenoxy-benzyl)-piperidine-3-carboxylic acid (Intermediate 51, 0.1 g, 0.29 mmol) was taken in anhydrous dichloromethane (5 mL) along with 2-aminomethyl pyridine (0.045 mL, 0.44 mmol) and triethylamine (0.16 mL, 1.17 mmol). The reaction mixture was cooled to 0° C. and propane phosphonic acid anhydride (T3P) (0.28 g, 0.88 mmol) was added dropwise. The reaction mixture was stirred for 3 h at ambient temperature. The organic phase was washed with water (2×20 mL), dried over anhydrous sodium sulfate and concentrated under reduced pressure to get a crude mass, which was purified by column chromatography to provide the titled compound as an off white gum (63%, 80 mg). LCMS: 430.3 (M+H), Rt. 3.8 min, 97.8% (max), 97.6% (220 nm). NMR: 400 MHz, DMSO-d$_6$: δ 8.46-8.48 (m, 1H), 8.27 (s, 1H), 7.71-7.72 (m, 1H), 7.35-7.39 (m, 2H), 7.27-7.31 (m, 1H), 7.21-7.24 (m, 2H), 7.13-7.15 (m, 1H), 6.97-7.02 (m, 3H), 6.85-6.88 (m, 2H), 0.00 (s, 2H), 0.00 (d, J=5.72 Hz, 2H), 3.19-3.22 (m, 2H), 2.29-2.34 (m, 1H), 1.65-1.70 (m, 2H), 1.54-1.60 (m, 1H), 1.35 (s, 3H).

Example 8

1-[3-(Pyrrolidine-1-sulfonyl)-benzyl]-pyrrolidine-3-carboxylic acid (4,6-dimethyl-pyridin-2-ylmethyl)-amide hydrochloride (111)

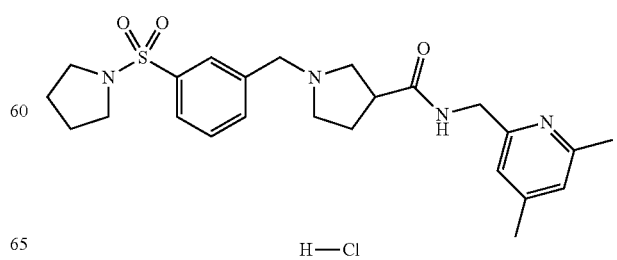

A solution of bis(trimethylaluminum)-1,4-diazabicyclo[2.2.2]octane adduct (65.5 mg; 0.26 mmol; 1.50 eq.) and (4,6-dimethylpyridin-2-yl)methanamine (34.5 μl; 0.26 mmol; 1.50 eq.) in anhydrous THF (2.00 ml) was irradiated in the microwave at 130° C. for 20 min. A solution of 1-[3-(pyrrolidine-1-sulfonyl)-benzyl]-pyrrolidine-3-carboxylic acid methyl ester (intermediate 68; 60.00 mg; 0.17 mmol; 1.00 eq.) in anhydrous THF (0.5 ml) was added to the reaction mixture and the purple solution was irradiated in the microwave at 130° C. for 40 min. To the reaction mixture was added methanol (0.5 ml), stirred an additional 10 min at room temperature and concentrated under reduced pressure. The residue was purified by column chromatography (dichloromethane/methanol 0-10%). The pure fractions were concentrated under reduced pressure, dissolved in methanol (2 ml), aqueous 1N hydrochloric acid (168 μl) and water were added, and lyophilized to give the titled compound as a yellow glassy solid (74 mg, 87%). $^1$H NMR (MeOD-$d_4$) δ 8.08 (s, 1H), 7.96 (d, J=7.9 Hz, 1H), 7.89 (d, J=7.7 Hz, 1H), 7.74 (t, J=7.8 Hz, 1H), 7.63 (d, J=6.3 Hz, 2H), 4.75-4.46 (m, 4H), 3.81-3.34 (m, 5H), 3.27 (ddd, J=6.8, 4.3, 2.7 Hz, 4H), 2.74 (s, 3H), 2.60 (s, 3H), 2.32 (ddd, J=86.5, 22.6, 14.0 Hz, 2H), 1.76 (t, J=6.6 Hz, 4H). LCMS: 457 (M+1), Rt. 1.97 min. HPLC: 98.8% (254 nm), Rt. 2.26 min.

Example 9

Compound Plate Preparation

Supplied compounds were sent as Assay Ready Plates, with 2 μL per well of compound in DMSO at 300× the final assay concentrations as described above and in the project proposal. All assay plates are stored at in a −80° C. freezer.

On the day of the assay, 198 μL of external solution was added to the appropriate assay plate and mixed thoroughly. This provided a 1:100 dilution. A further 1:3 dilution occurred upon addition to the cells in the IonWorks, giving a 1:300 dilution in total.

On each assay plate, at least 8 wells were reserved for vehicle control (0.3% DMSO) and at least 8 wells for each positive control specific to the cell line tested. The positive controls were tested in an 8-point dose response with 3-fold dilutions to determine an $IC_{50}$ value for each run. The positive control compounds are outlined below.

Ion Channel Positive Control & Concentrations
Nav1.6/1.2 Lidocaine: 8, 3-fold dilutions starting at 100 μM
Electrophysiological Recording Solutions
The solutions for recording currents were are follows:

| External Recording Solution | | Internal Recording Solution | |
|---|---|---|---|
| NaCl | 137 mM | CsF | 90 mM |
| KCl | 4 mM | CsCl | 45 mM |
| $MgCl_2$ | 1 mM | HEPES | 10 mM |
| $CaCl_2$ | 1.8 mM | EGTA | 10 mM |
| HEPES | 10 mM | pH 7.3 (titrated with 1M CsOH) | |
| Glucose | 10 mM | | |
| p.H 7.3 (titrated with 10M NaOH) | | | |

Amphotericin B was used to obtain electrical access to the cell interior at a final concentration of 200 μg/ml in internal recording solution.
Experimental Protocols & Data Analysis
Nav Two-Pulse Protocol Nav currents were evoked by stepping from a holding potential of −120 mV to 0 mV for 2.5 s (pulse 1), followed by a 5 ms inter-pulse interval, and stepping from a holding potential of −120 mV to 0 mV for 20 ms (pulse 2). The voltage protocol was applied (Pre), compounds added, incubated for 300 seconds, and the voltage protocol was applied a final time (Post) on the IonWorks Quattro.

| Experiment Step | Step Duration |
|---|---|
| Start | 0 m, 18 s |
| Prime Plate | 4 m, 36 s |
| Add Cells | 1 m, 45 s |
| Seal Test | 8 m, 50 s |
|   Min: −130 mV, Max: −120 mV, | |
|   Period: 160 ms | |
|   Wait 480 s before running the test | |
| Obtain Access | 12 m, 11 s |
|   1. Pause for 1 s | |
|   2. Introduce Agent for 70 s | |
|   3. Circulate fluid for 600 s | |
|   4. Pause for 60 s | |
| Measure Currents | 34 m, 34 s |
|   Apply signal once with no repetitions | |
|   Command Voltage time = 11.7876 s | |
|   Pre/Post Holding time = 30/1 s; | |
|   Sample interval = 0.1 ms | |
|   Offset-voltage correction (mV): | |
|   Pre = 0, Post = 0 | |
|   Draw compounds from Plate 1: | |
|     Nunc 384 clear polystyrene | |
|     Cat. No. 262160 | |
|     *Use entire 384 wells | |
|     mix cycles: 4, wash cycles: 20 | |
| Compound Incubation Time = 300 s | |
| Use a "Half-at-Once" scan | |
| Pipettor Prewetting: Duration = 30 s | |
|   Expel to waste | |
| Solvent Wash at Plate 2:20 wash cycles | |
|   Nunc 384 clear polystyrene, | |
|   Cat. No. 262160 | |
| Clean Up | 2 m, 29 s |
| | Estimated Experiment Time = 64 m, 43 s |

Nav Data Analysis

The parameters measured were the maximum inward current evoked on stepping to 0 mV from the $1^{st}$ and $2^{nd}$ pulse. All data were filtered for seal quality, seal drop, and current amplitude. The peak current amplitude (Peak) was calculated before (Pre) and after (Post) compound addition to the amount of block was assessed by dividing the Post-compound current amplitude by the Pre-compound current amplitude. These procedures were implemented for the $1^{st}$ and $2^{nd}$ pulse.

The data is interpreted according to the following:

| Nav1.6 inac | | Nav1.6 Tonic | |
|---|---|---|---|
| + | >5 μM; | + | >20 μM; |
| ++ | 1-5 μM; | ++ | 10-20 μM; |
| +++ | <1 μM. | +++ | <10 μM. |

| Compound number | Nav1.6 inac | Nav1.6 Tonic |
|---|---|---|
| 1 | +++ | + |
| 2 | ++ | + |
| 3 | ++ | + |
| 4 | +++ | ++ |
| 5 | +++ | + |
| 6 | + | + |
| 7 | +++ | + |
| 8 | +++ | + |
| 9 | +++ | + |
| 10 | ++ | ++ |
| 11 | +++ | ++ |
| 12 | ++ | + |
| 13 | +++ | + |

-continued

| Nav1.6 inac | | Nav1.6 Tonic |
|---|---|---|
| 14 | + | + |
| 15 | + | + |
| 16 | | |
| 17 | ++ | ++ |
| 18 | + | + |
| 19 | ++ | + |
| 20 | + | + |
| 21 | ++ | + |
| 22 | ++ | + |
| 23 | ++ | + |
| 24 | ++ | + |
| 25 | ++ | + |
| 26 | ++ | + |
| 27 | + | + |
| 28 | +++ | + |
| 29 | ++ | ++ |
| 30 | +++ | + |
| 31 | ++ | + |
| 32 | ++ | + |
| 33 | ++ | + |
| 34 | ++ | + |
| 35 | ++ | + |
| 36 | +++ | + |
| 37 | ++ | + |
| 38 | + | + |
| 39 | ++ | + |
| 40 | +++ | ++ |
| 41 | +++ | ++ |
| 42 | + | + |
| 43 | + | + |
| 44 | + | + |
| 45 | + | + |
| 46 | ++ | + |
| 47 | ++ | + |
| 48 | ++ | + |
| 49 | ++ | + |
| 50 | + | + |
| 51 | ++ | + |
| 52 | ++ | + |
| 53 | ++ | + |
| 54 | ++ | + |
| 55 | ++ | + |
| 56 | ++ | + |
| 57 | ++ | + |
| 58 | + | + |
| 59 | + | + |
| 60 | ++ | + |
| 61 | + | + |
| 62 | ++ | + |
| 63 | + | + |
| 64 | ++ | + |
| 65 | +++ | + |
| 66 | +++ | ++ |
| 67 | +++ | ++ |
| 68 | ++ | ++ |
| 69 | +++ | + |
| 70 | ++ | ++ |
| 71 | ++ | ++ |
| 72 | ++ | ++ |
| 73 | ++ | ++ |
| 74 | ++ | ++ |
| 75 | ++ | ++ |
| 76 | +++ | ++ |
| 77 | +++ | ++ |
| 78 | ++ | ++ |
| 79 | +++ | ++ |
| 80 | +++ | ++ |
| 81 | +++ | ++ |
| 82 | +++ | ++ |
| 83 | ++ | + |
| 84 | +++ | ++ |
| 85 | ++ | + |
| 86 | + | |
| 87 | +++ | +++ |
| 88 | +++ | + |
| 89 | ++ | + |
| 90 | ++ | + |
| 91 | + | + |
| 92 | ++ | + |
| 93 | ++ | + |
| 94 | ++ | + |
| 95 | + | + |
| 96 | + | + |
| 97 | + | + |
| 98 | + | + |
| 99 | ++ | + |
| 100 | ++ | ++ |
| 101 | ++ | + |
| 102 | ++ | + |
| 103 | + | + |
| 104 | ++ | + |
| 105 | ++ | + |
| 106 | + | + |
| 107 | ++ | + |
| 108 | ++ | + |
| 109 | +++ | ++ |
| 110 | +++ | ++ |
| 111 | ++ | + |

Example 10

Pharmaceutical Preparations (A) Injection vials: A solution of 100 g of an active ingredient according to the invention and 5 g of disodium hydrogen phosphate in 3 l of bidistilled water is adjusted to pH 6.5 using 2 N hydrochloric acid, sterile filtered, transferred into injection vials, is lyophilized under sterile conditions and is sealed under sterile conditions. Each injection vial contains 5 mg of active ingredient.

(B) Suppositories: A mixture of 20 g of an active ingredient according to the invention is melted with 100 g of soy lecithin and 1400 g of cocoa butter, is poured into moulds and is allowed to cool. Each suppository contains 20 mg of active ingredient.

(C) Solution: A solution is prepared from 1 g of an active ingredient according to the invention, 9.38 g of $NaH_2PO_4.2 H_2O$, 28.48 g of $Na_2HPO_4.12 H_2O$ and 0.1 g of benzalkonium chloride in 940 ml of bidistilled water. The pH is adjusted to 6.8, and the solution is made up to 1 l and sterilized by irradiation. This solution could be used in the form of eye drops.

(D) Ointment: 500 mg of an active ingredient according to the invention is mixed with 99.5 g of Vaseline under aseptic conditions.

(E) Tablets: A mixture of 1 kg of an active ingredient according to the invention, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

(F) Coated tablets: Tablets are pressed analogously to Example E and subsequently are coated in a conventional manner with a coating of sucrose, potato starch, talc, tragacanth and dye.

(G) Capsules: 2 kg of an active ingredient according to the invention are introduced into hard gelatin capsules in a conventional manner in such a way that each capsule contains 20 mg of the active ingredient.

(H) Ampoules: A solution of 1 kg of an active ingredient according to the invention in 60 l of bidistilled water is sterile filtered, transferred into ampoules, is lyophilized under sterile conditions and is sealed under sterile conditions. Each ampoule contains 10 mg of active ingredient.

(I) Inhalation spray: 14 g of an active ingredient according to the invention are dissolved in 10 l of isotonic NaCl solution, and the solution is transferred into commercially available spray containers with a pump mechanism. The solution could be sprayed into the mouth or nose. One spray shot (about 0.1 ml) corresponds to a dose of about 0.14 mg.

While a number of embodiments of this invention are described herein, it is apparent that the basic examples may be altered to provide other embodiments that utilize the compounds and methods of this invention. Therefore, it will be appreciated that the scope of this invention is to be defined by the appended claims rather than by the specific embodiments that have been represented by way of example.

We claim:
1. A compound of formula VI,

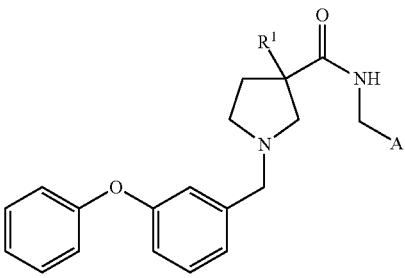

VI or a pharmaceutically acceptable salt thereof, wherein:
A is selected from the following:

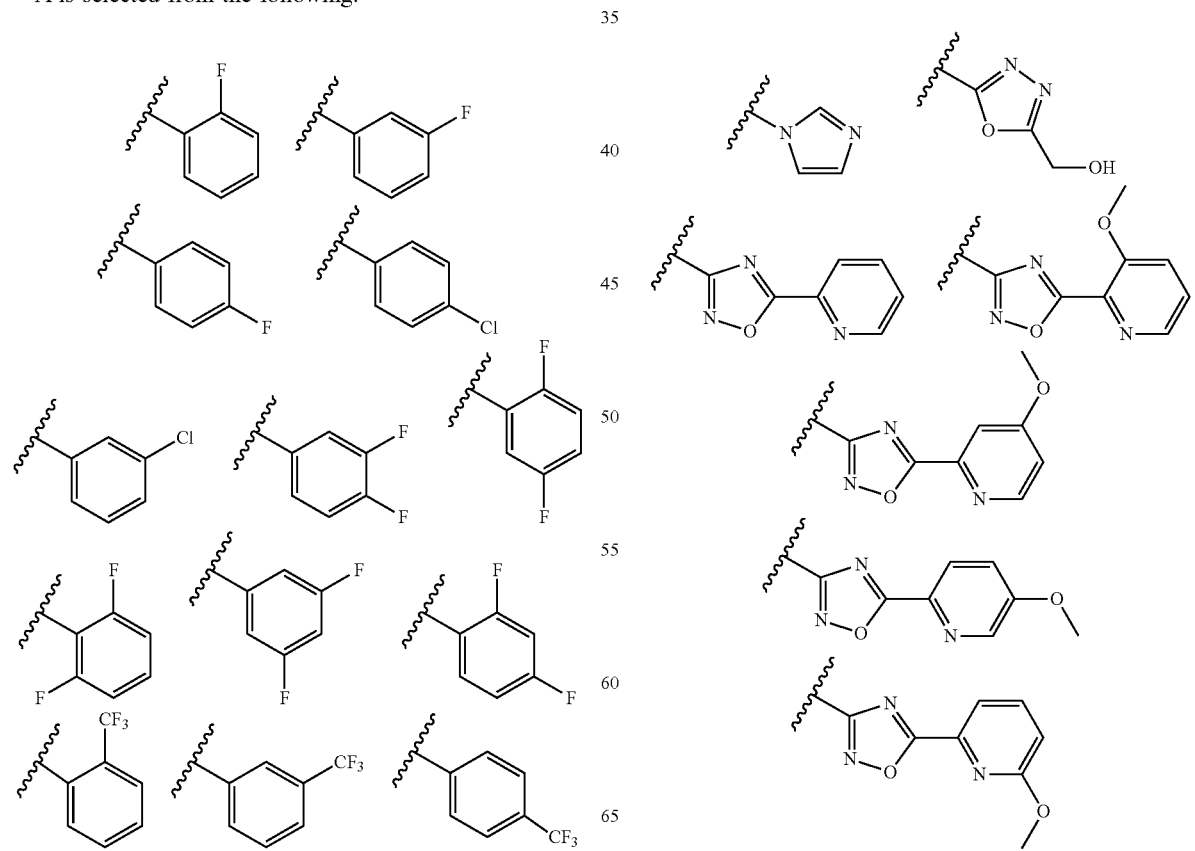

-continued

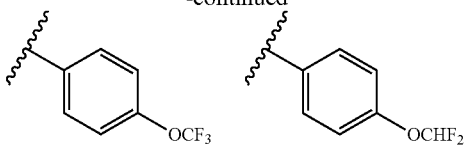

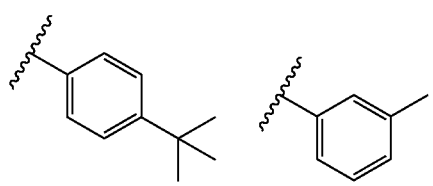

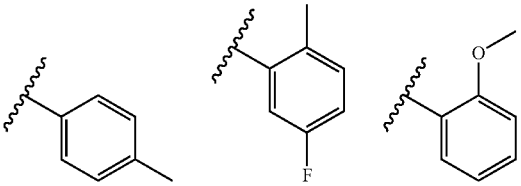

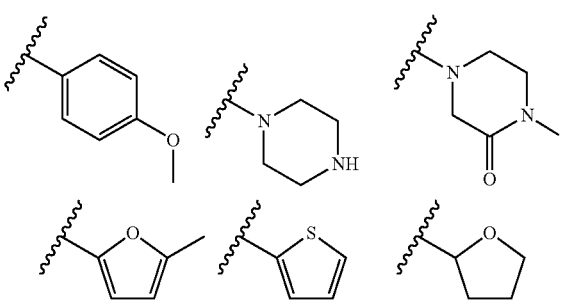

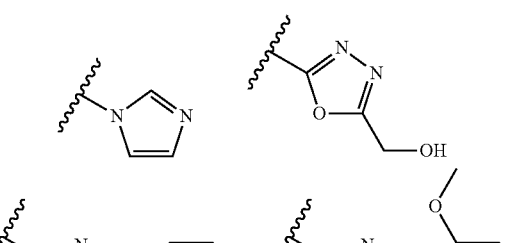

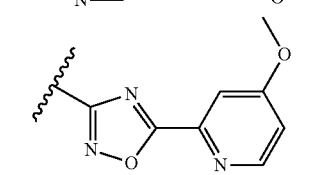

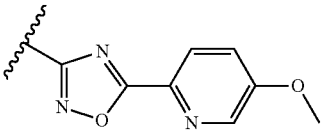

-continued
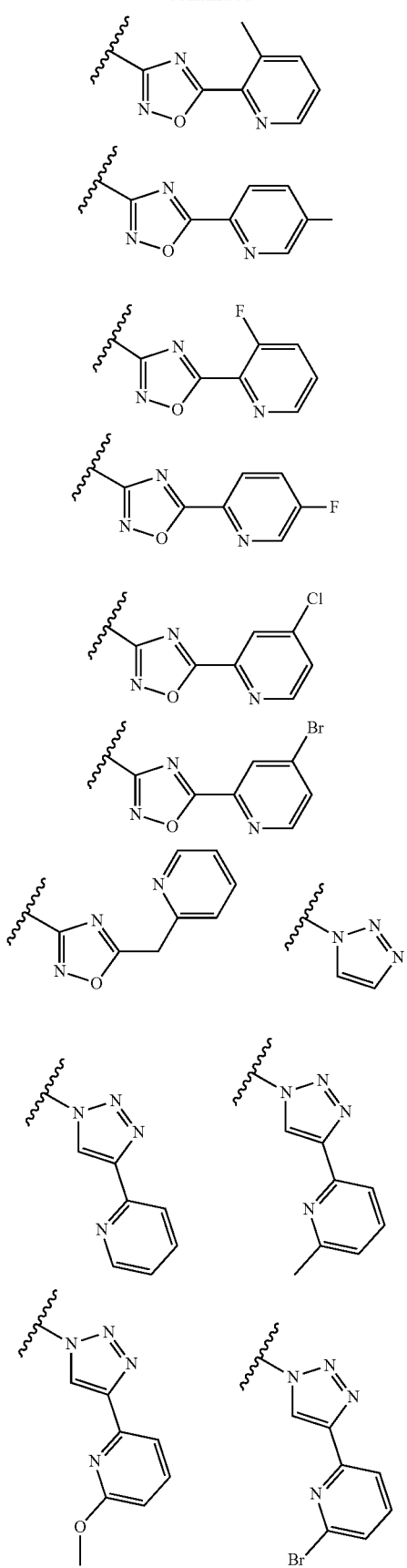
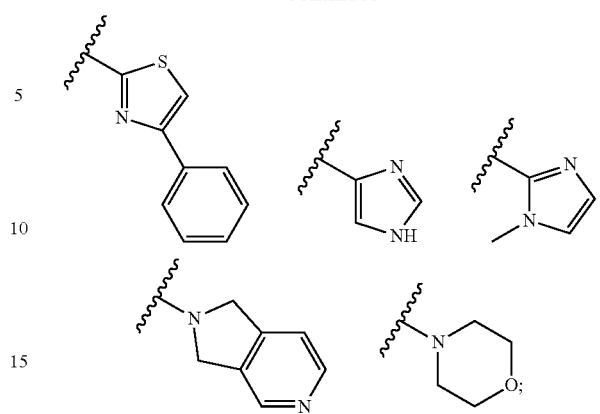
and
R$^1$ is —H, halogen, -haloalkyl, or —OH.
2. The compound of claim 1, wherein R$^1$ is H.
3. The compound of claim 1, wherein R$^1$ is F, Cl, or OH.
4. The compound of claim 1, selected from
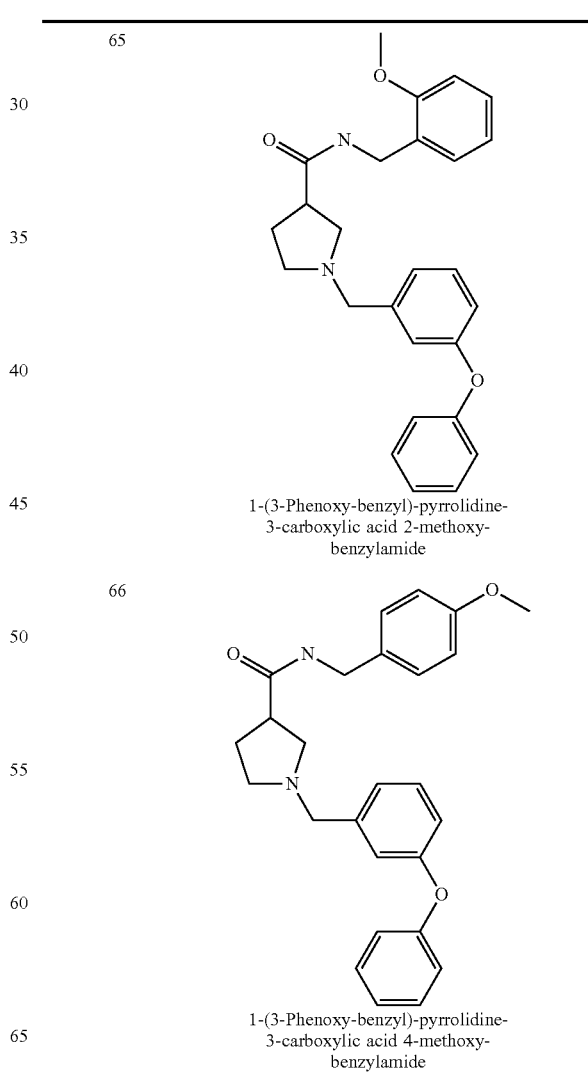
65
1-(3-Phenoxy-benzyl)-pyrrolidine-3-carboxylic acid 2-methoxy-benzylamide
66
1-(3-Phenoxy-benzyl)-pyrrolidine-3-carboxylic acid 4-methoxy-benzylamide

| | |
|---|---|
| 67 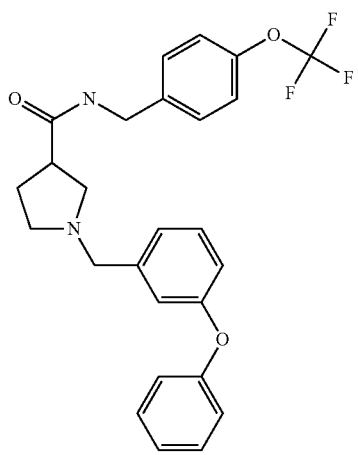 [SMILES: O=C(NCc1ccc(OC(F)(F)F)cc1)C1CCN(Cc2cccc(Oc3ccccc3)c2)C1]<br>1-(3-Phenoxy-benzyl)-pyrrolidine-3-carboxylic acid 4-trifluoromethoxy-benzylamide | 70 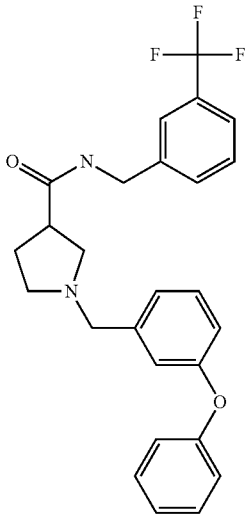<br>1-(3-Phenoxy-benzyl)-pyrrolidine-3-carboxylic acid 3-trifluoromethyl-benzylamide |
| 68 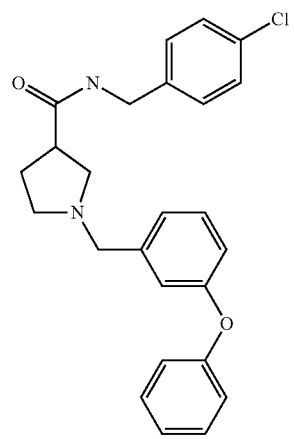 [SMILES: O=C(NCc1ccc(Cl)cc1)C1CCN(Cc2cccc(Oc3ccccc3)c2)C1]<br>1-(3-Phenoxy-benzyl)-pyrrolidine-3-carboxylic acid 4-chloro-benzylamide | 71 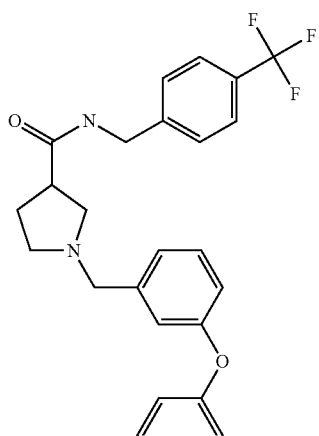<br>1-(3-Phenoxy-benzyl)-pyrrolidine-3-carboxylic acid 4-trifluoromethyl-benzylamide |
| 69 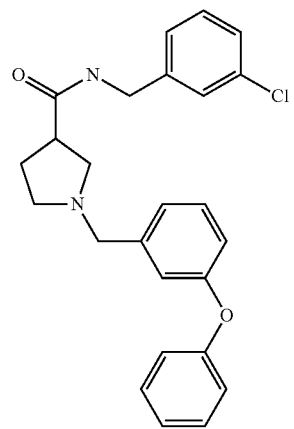 [SMILES: O=C(NCc1cccc(Cl)c1)C1CCN(Cc2cccc(Oc3ccccc3)c2)C1]<br>1-(3-Phenoxy-benzyl)-pyrrolidine-3-carboxylic acid 3-chloro-benzylamide | 72 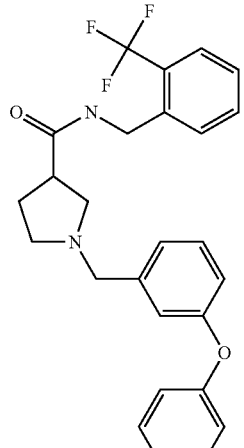<br>1-(3-Phenoxy-benzyl)-pyrrolidine-3-carboxylic acid 2-trifluoromethyl-benzylamide |

-continued

73

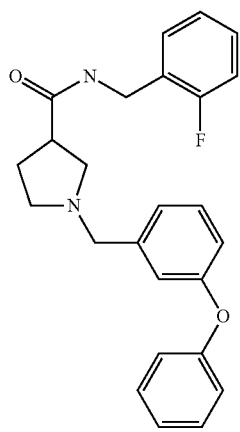 [SMILES: O=C(NCc1ccccc1F)C1CCN(Cc2cccc(Oc3ccccc3)c2)C1]

1-(3-Phenoxy-benzyl)-pyrrolidine-
3-carboxylic acid 2-fluoro-
benzylamide

74

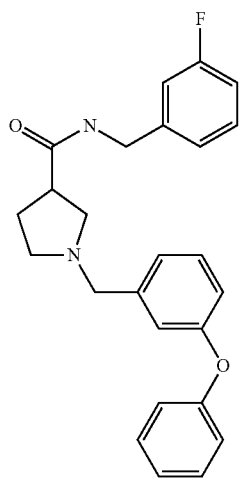 [SMILES: O=C(NCc1cccc(F)c1)C1CCN(Cc2cccc(Oc3ccccc3)c2)C1]

1-(3-Phenoxy-benzyl)-pyrrolidine-
3-carboxylic acid 3-fluoro-
benzylamide

75

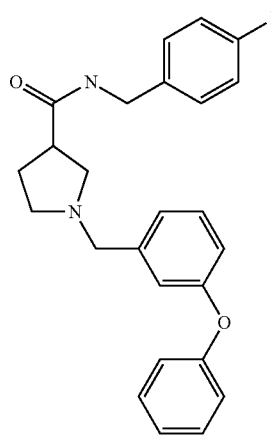

1-(3-Phenoxy-benzyl)-pyrrolidine-
3-carboxylic acid 4-fluoro-
benzylamide

-continued

76

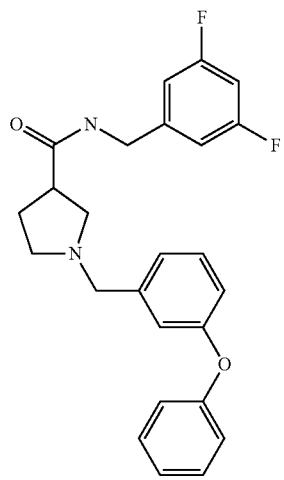 [SMILES: O=C(NCc1cc(F)cc(F)c1)C1CCN(Cc2cccc(Oc3ccccc3)c2)C1]

1-(3-Phenoxy-benzyl)-pyrrolidine-
3-carboxylic acid 3,5-difluoro-
benzylamide

77

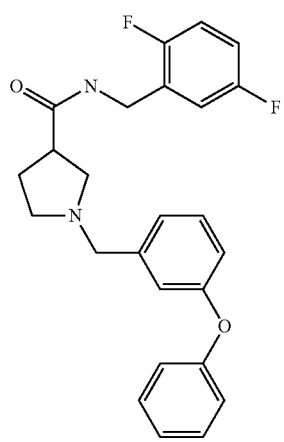 [SMILES: O=C(NCc1cc(F)ccc1F)C1CCN(Cc2cccc(Oc3ccccc3)c2)C1]

1-(3-Phenoxy-benzyl)-pyrrolidine-
3-carboxylic acid 2,5-difluoro-
benzylamide

78

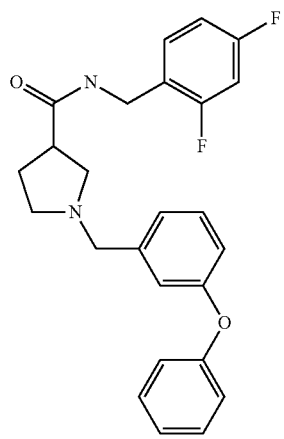 [SMILES: O=C(NCc1ccc(F)cc1F)C1CCN(Cc2cccc(Oc3ccccc3)c2)C1]

1-(3-Phenoxy-benzyl)-pyrrolidine-
3-carboxylic acid 2,4-difluoro-
benzylamide

| 79 | 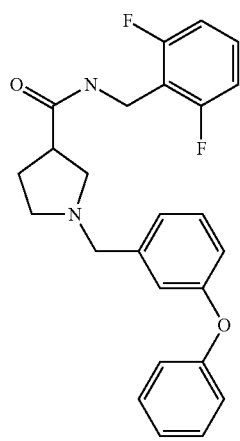 [SMILES: O=C(NCc1c(F)cccc1F)C1CCN(Cc2cccc(Oc3ccccc3)c2)C1] 1-(3-Phenoxy-benzyl)-pyrrolidine-3-carboxylic acid 2,6-difluoro-benzylamide | 82 | 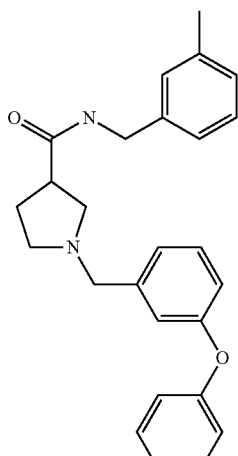 1-(3-Phenoxy-benzyl)-pyrrolidine-3-carboxylic acid 3-methyl-benzylamide |
|---|---|---|---|
| 80 | 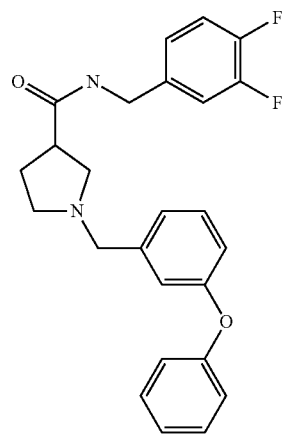 [SMILES: O=C(NCc1ccc(F)c(F)c1)C1CCN(Cc2cccc(Oc3ccccc3)c2)C1] 1-(3-Phenoxy-benzyl)-pyrrolidine-3-carboxylic acid 3,4-difluoro-benzylamide | 83 | 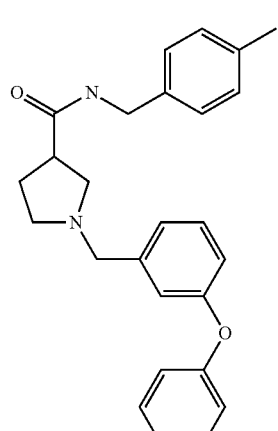 1-(3-Phenoxy-benzyl)-pyrrolidine-3-carboxylic acid 4-methyl-benzylamide |
| 81 | 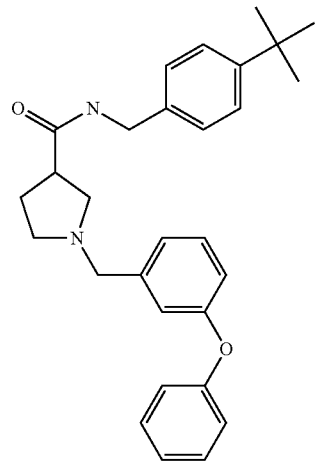 [SMILES: CC(C)(C)c1ccc(CNC(=O)C2CCN(Cc3cccc(Oc4ccccc4)c3)C2)cc1] 1-(3-Phenoxy-benzyl)-pyrrolidine-3-carboxylic acid 4-tert-butyl-benzylamide | 84 | 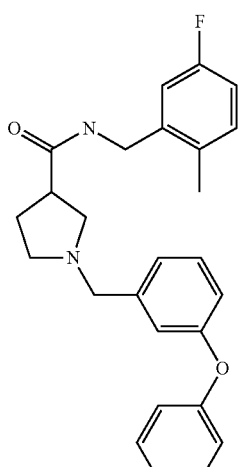 1-(3-Phenoxy-benzyl)-pyrrolidine-3-carboxylic acid 5-fluoro-2-methyl-benzylamide |

| | |
|---|---|
| 85 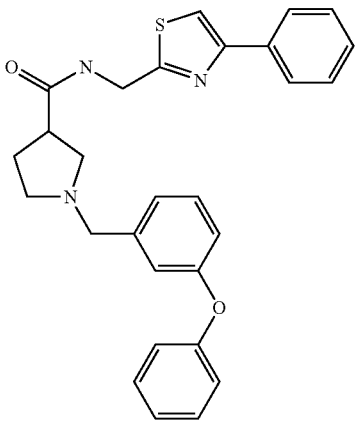 [SMILES: O=C(NCc1nc(-c2ccccc2)cs1)C1CCN(Cc2cccc(Oc3ccccc3)c2)C1]<br>1-(3-Phenoxy-benzyl)-pyrrolidine-<br>3-carboxylic acid (4-phenyl-thiazol-2-<br>ylmethyl)-amide | 88 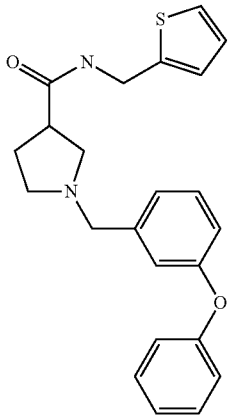<br>1-(3-Phenoxy-benzyl)-pyrrolidine-<br>3-carboxylic acid (thiophen-2-<br>ylmethyl)-amide |
| 86 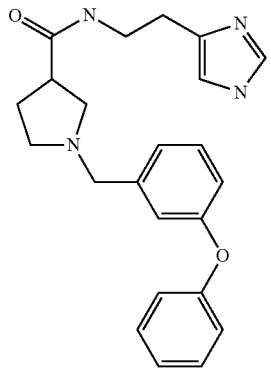 [SMILES: O=C(NCCc1c[nH]cn1)C1CCN(Cc2cccc(Oc3ccccc3)c2)C1]<br>1-(3-Phenoxy-benzyl)-pyrrolidine-<br>3-carboxylic acid [2-(1H-imidazol-4-<br>yl)-ethyl]-amide | 91 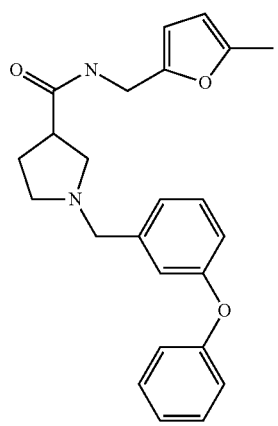<br>1-(3-Phenoxy-benzyl)-pyrrolidine-<br>3-carboxylic acid (5-methyl-furan-2-<br>ylmethyl)-amide |
| 87 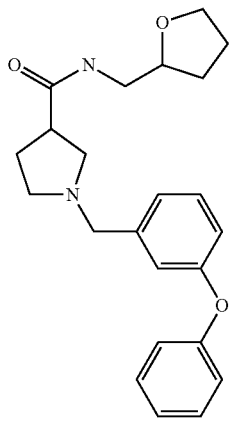 [SMILES: O=C(NCC1CCCO1)C1CCN(Cc2cccc(Oc3ccccc3)c2)C1]<br>1-(3-Phenoxy-benzyl)-pyrrolidine-<br>3-carboxylic acid (tetrahydro-furan-2-<br>ylmethyl)-amide | 96 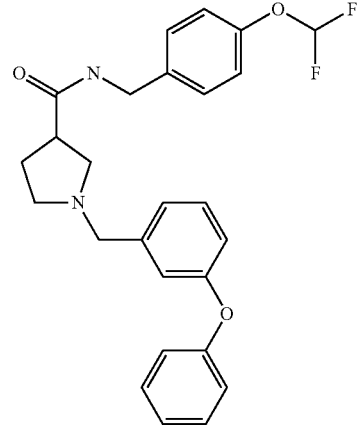 [SMILES: O=C(NCc1ccc(OC(F)F)cc1)C1CCN(Cc2cccc(Oc3ccccc3)c2)C1]<br>1-(3-Phenoxy-benzyl)-pyrrolidine-<br>3-carboxylic acid 4-difluoromethoxy-<br>benzylamide; and |

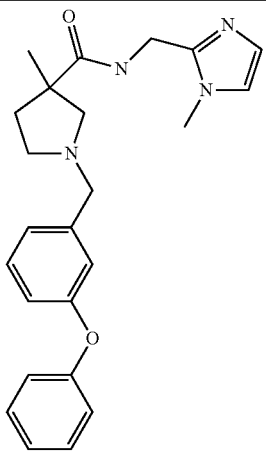
101 3-Methyl-1-(3-phenoxy-benzyl)-pyrrolidine-3-carboxylic acid (1-methyl-1H-imidazol-2-ylmethyl)-amide.
5. A pharmaceutical composition comprising a compound of claim 1, and a pharmaceutically acceptable adjuvant, carrier, or vehicle.
* * * * *